(12) United States Patent
Baumann et al.

(10) Patent No.: US 7,910,740 B2
(45) Date of Patent: Mar. 22, 2011

(54) MODULATORS OF AMYLOID BETA

(75) Inventors: Karlheinz Baumann, Efringen-Kirchen (DE); Alexander Flohr, Reinach (CH); Helmut Jacobsen, Schopfheim (DE); Synese Jolidon, Blauen (CH); Thomas Luebbers, Loerrach (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 274 days.

(21) Appl. No.: 12/114,852

(22) Filed: May 5, 2008

(65) Prior Publication Data
US 2008/0280948 A1 Nov. 13, 2008

(30) Foreign Application Priority Data
May 11, 2007 (EP) .................... 07108004

(51) Int. Cl.
*C07D 513/04* (2006.01)
*C07D 277/60* (2006.01)
*C07D 277/42* (2006.01)
*A61K 31/427* (2006.01)
*A61K 31/428* (2006.01)
*A61K 31/429* (2006.01)

(52) U.S. Cl. ........ 546/114; 548/161; 548/184; 514/301; 514/367; 514/370

(58) Field of Classification Search .................. 546/114; 548/181, 190, 198, 161, 184; 514/301, 367, 514/370
See application file for complete search history.

(56) References Cited

U.S. PATENT DOCUMENTS
| | | | |
|---|---|---|---|
| 2003/0176454 A1* | 9/2003 | Yamada et al. | 514/284 |
| 2006/0004013 A1 | 1/2006 | Kimura et al. | |
| 2007/0117798 A1 | 5/2007 | Kimura et al. | |
| 2007/0117839 A1 | 5/2007 | Kimura et al. | |
| 2007/0219181 A1 | 9/2007 | Kimura et al. | |

FOREIGN PATENT DOCUMENTS
| | | |
|---|---|---|
| EP | 1950211 | 7/2008 |
| WO | WO 99/65884 | 12/1999 |
| WO | WO 01/87845 A2 * | 11/2001 |
| WO | WO 2004/110350 | 12/2004 |
| WO | WO 2005/115990 | 12/2005 |
| WO | WO 2006/058905 | 6/2006 |
| WO | WO 2006/112551 | 10/2006 |
| WO | WO 2007/058304 | 5/2007 |
| WO | WO 2007/058305 | 5/2007 |
| WO | WO 2007/102580 | 9/2007 |

OTHER PUBLICATIONS
Weggen, et al., Nature vol. 414, pp. 212-216 (2001).
Morihara et al., J. Neurochem. vol. 83, pp. 1009-1012 (2002).
Jantzen et al., J. Neuroscience, vol. 22, pp. 226-254 (2002).
Takahashi et al., J. Biol. Chem. vol. 278 pp. 18644-18670 (2003).
Beher et al., J. Biol. Chem. vol. 279 pp. 43419-43426 (2004).
Lleo et al., Nature Med. vol. 10, pp. 1065-1066 (2004).
Kukar et al., Nature Med. vol. 11 pp. 545-550 (2005).
Perretto et al., J. Med. Chem. vol. 48 pp. 5705-5720 (2005).
Clarke et al., J. Biol. Chem. vol. 281 pp. 31279-31289 (2006).
Stock et al., Bioorg. Med. Chem. Lett. vol. 16, pp. 2219-2223 (2006).
Narlawar et al., J. Med. Chem. vol. 49 pp. 7588-7591 (2006).
McPhee et al. J. Med. Chem. Soc. vol. 66 p. 1132 (1944).
Yang et al., J. Org. Chem. vol. 67(21) p. 7429 (2002).

\* cited by examiner

*Primary Examiner* — Rita J Desai
*Assistant Examiner* — David K O'Dell
(74) *Attorney, Agent, or Firm* — George W. Johnston; Patricia S. Rocha-Tramaloni; Kimberly J. Prior

(57) ABSTRACT

The invention relates to compounds of formula

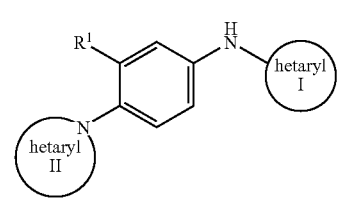

I wherein hetaryl I, hetaryl II, and $R^1$ are as described herein. Compounds of formula I are modulators for amyloid beta and thus, they may be useful for the treatment or prevention of a disease associated with the deposition of β-amyloid in the brain, in particular Alzheimer's disease.

19 Claims, No Drawings

MODULATORS OF AMYLOID BETA

PRIORITY TO RELATED APPLICATION(S)

This application claims the benefit of European Patent Application No. 07108004.8, filed May 11, 2007, which is hereby incorporated by reference in its entirety.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has loose substrate specificity and may cleave further membrane proteins unrelated to APP and Notch.

The γ-secretase activity is absolutely required for the production of Aβ peptides. This has been shown both by genetic means, i.e., ablation of the presenilin genes and by low-molecular-weight inhibitory compounds. Since according to the amyloid hypothesis for AD the production and deposition of Aβ is the ultimate cause for the disease, it is thought that selective and potent inhibitors of γ-secretase will be useful for the prevention and treatment of AD.

An alternative mode of treatment is the modulation of the γ-secretase activity which results in a selective reduction of the Aβ42 production. This will result in to an increase of shorter Aβ isoforms, such as Aβ38, Aβ37 or others, which have reduced capability for aggregation and plaque formation, and hence less neurotoxic. Compounds which show this effect on modulating γ-secretase activity include certain non-steroidal anti-inflammatory drugs (NSAIDs) and related analogues (Weggen et al. Nature, 414 (2001) 212-16).

Numerous documents describe the current knowledge on γ-secretase modulation, for example the following publications:

Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91

SUMMARY OF THE INVENTION

The invention provides compounds of formula I

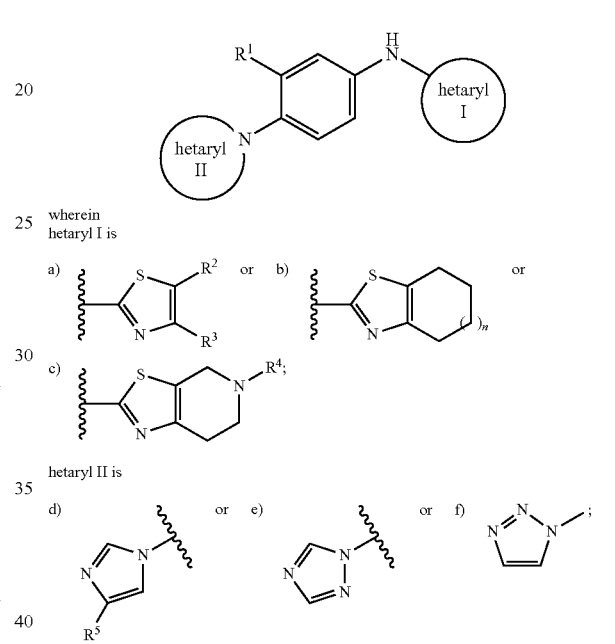

wherein
hetaryl I is a) or b) or c)

hetaryl II is d) or e) or f)

$R^1$ is hydrogen, lower alkoxy or cyano;
$R^2$ and $R^3$ are each independently
  hydrogen,
  lower alkyl,
  lower alkyl substituted by halogen,
  CHO,
  phenyl or —CRR'-phenyl, wherein phenyl rings are unsubstituted or substituted by one or more halogen, cyano, lower alkyl, lower alkyl substituted by halogen, lower alkoxy substituted by halogen or lower alkoxy,
  —C(O)O-lower alkyl,
  —CH₂—C(O)O-lower alkyl,
  —CH₂—C(O)-piperidin-1-yl,
  —CH₂—C(O)NH-lower alkyl,
  —CH₂—C(O)NH-phenyl optionally substituted by halogen,
  —CHR—NHC(O)O-lower alkyl,
  —CHR—NH₂,
  —CHR—NH—CH₂-phenyl optionally substituted by halogen,
  —CHR—NH—(CH₂)₂-phenyl optionally substituted by halogen,
  —CHR—NH-phenyl optionally substituted by halogen,
  —CHR—NH-cycloalkyl, —CHR—NHC(O)—CH$_2$-phenyl optionally substituted by halogen,
—CHR—NHC(O)—CH$_2$O-lower alkyl,
—CHR—NHC(O)-lower alkyl,
—CHR—NHC(O)O-lower alkyl substituted by halogen,
—CHR—NHC(O)-phenyl optionally substituted by halogen,
—CHR—NHCH$_2$CH$_2$O-lower alkyl,
—CHR—NH—S(O)$_2$-phenyl optionally substituted by halogen or lower alkyl,
—CHR—NH—S(O)$_2$—CH$_2$-phenyl optionally substituted by halogen,
—CHR—NH—S(O)$_2$-lower alkyl,
CH$_2$-piperidin-1-yl,
CH$_2$-morpholinyl or
-indole-2-carboxylic acid-(3,4-difluoro-phenyl)amide;
R and R' are each independently hydrogen, lower alkyl, benzyl or hydroxy;
R$^4$ is hydrogen,
—C(O)O-lower alkyl,
—C(O)-phenyl optionally substituted by halogen,
—C(O)-lower alkyl substituted by halogen,
—C(O)-lower alkyl,
—S(O)$_2$-phenyl optionally substituted by halogen,
—S(O)$_2$-lower alkyl,
—S(O)$_2$—CH$_2$-phenyl,
-benzyl optionally substituted by halogen,
—CH$_2$—CH$_2$-phenyl,
—C(O)—CH$_2$-phenyl optionally substituted by halogen or
—C(O)—CH$_2$-lower alkoxy;
R$^5$ is hydrogen, halogen, lower alkyl substituted by hydroxy, or is lower alkyl; and
n is 0 or 1;
or pharmaceutically active acid addition salts.

The invention includes all forms of optically pure enantiomers, racemates or diastereomeric mixtures for compounds of formula I.

The invention also provides pharmaceutical compositions containing compounds of the invention and processes for the preparation of compounds of formula I and compositions containing them.

Compounds of formula I are modulators for amyloid beta and thus, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by hydroxy" denotes an alkyl group as defined above, wherein at least one hydrogen atom is replaced by hydroxy, for example CH$_2$OH, CH$_2$CH$_2$OH, CH$_2$CH$_2$CH$_2$OH, CH(CH$_2$)CH$_2$OH, and the like.

The term "halogen" denotes chlorine, iodine, fluorine and bromine.

As used herein, the term "lower alkyl substituted by halogen" denotes an alkyl group as defined above, wherein at least one hydrogen atom is replaced by halogen, for example CF$_3$, CHF$_2$, CH$_2$F, CH$_2$CF$_3$, CH$_2$CH$_2$CF$_3$, CF$_2$CHF$_2$, CH$_2$CF$_2$CF$_3$ and the like.

As used herein, the term "lower alkoxy" denotes a group wherein the alkyl residue is as defined above and which is attached via an oxygen atom.

As used herein, the term "lower alkoxy substituted by halogen" denotes an alkoxy group as defined above, wherein at least one hydrogen atom is replaced by halogen, for example OCF$_3$, OCHF$_2$, OCH$_2$F, OCH$_2$CF$_3$, OCH$_2$CH$_2$CF$_3$, OCF$_2$CHF$_2$, OCH$_2$CF$_2$CF$_3$ and the like.

The term "cycloalkyl" denotes an alicyclic carbon ring having 3 to 6 carbon atoms as ring members and includes, but is not limited to, cyclopropyl, cyclobutyl, cyclopentyl, cyclohexyl, as well as those groups specifically illustrated by the examples herein below.

The term "pharmaceutically acceptable" such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

Preferred compounds of formula I are compounds of formula I-A-1

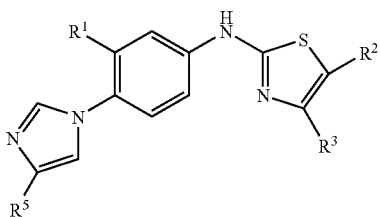

I-A-1 wherein
R$^1$ is hydrogen, lower alkoxy or cyano;
R$^2$ and R$^3$ are each independently
hydrogen,
lower alkyl,
lower alkyl substituted by halogen,
CHO,
phenyl or —CRR'-phenyl, wherein the phenyl rings are unsubstituted or substituted by one or more halogen, cyano, lower alkyl, lower alkyl substituted by halogen, lower alkoxy substituted by halogen or lower alkoxy,
—C(O)O-lower alkyl,
—CH$_2$—C(O)O-lower alkyl,
—CH$_2$—C(O)-piperidin-1-yl,
—CH$_2$—C(O)NH-lower alkyl, —CH$_2$—C(O)NH-phenyl optionally substituted by halogen,
—CHR—NHC(O)O-lower alkyl,
—CHR—NH$_2$,
—CHR—NH—CH$_2$-phenyl optionally substituted by halogen,
—CHR—NH—(CH$_2$)$_2$-phenyl optionally substituted by halogen,
—CHR—NH-phenyl optionally substituted by halogen,
—CHR—NH-cycloalkyl,
—CHR—NHC(O)—CH$_2$-phenyl optionally substituted by halogen,
—CHR—NHC(O)—CH$_2$O-lower alkyl,
—CHR—NHC(O)-lower alkyl,
—CHR—NHC(O)O-lower alkyl substituted by halogen,
—CHR—NHC(O)-phenyl optionally substituted by halogen,
—CHR—NHCH$_2$CH$_2$O-lower alkyl,
—CHR—NH—S(O)$_2$-phenyl optionally substituted by halogen or lower alkyl,
—CHR—NH—S(O)$_2$—CH$_2$-phenyl optionally substituted by halogen,
—CHR—NH—S(O)$_2$-lower alkyl,
—CH$_2$-piperidin-1-yl,
—CH$_2$-morpholinyl or
-indole-2-carboxylic acid-(3,4-difluoro-phenyl) amide;
R and R' are each independently hydrogen, lower alkyl, benzyl or hydroxy; and
$R^5$ is hydrogen, halogen, lower alkyl substituted by hydroxy, or is lower alkyl;
or pharmaceutically active acid addition salts.

Especially preferred compounds of formula I-A-1 are those, wherein
$R^1$ is hydrogen, lower alkoxy or cyano;
$R^1$ and $R^3$ are each independently
hydrogen,
lower alkyl,
lower alkyl substituted by halogen,
—CRR'-phenyl, which is unsubstituted or substituted by one or more halogen, lower alkyl, lower alkyl substituted by halogen, lower alkoxy substituted by halogen, or lower alkoxy,
—CH$_2$—C(O)NH-phenyl optionally substituted by halogen,
—CHR—NHC(O)O-lower alkyl,
—CHR—NHC(O)O-lower alkyl substituted by halogen,
—CHR—NHC(O)—CH$_2$-phenyl optionally substituted by halogen,
—CHR—NHC(O)-phenyl optionally substituted by halogen,
—CHR—NH—S(O)$_2$-phenyl optionally substituted by halogen or lower alkyl,
—CHR—NH—S(O)$_2$—CH$_2$-phenyl optionally substituted by halogen, or
—CHR—NH—S(O)$_2$-lower alkyl;
R and R' are each independently hydrogen, lower alkyl, benzyl or hydroxyl, wherein at least one of R and R' is other than hydrogen; and
$R^5$ is hydrogen or lower alkyl;
or pharmaceutically active acid addition salts, for example the following compounds:
[5-(3-chloro-benzyl)-4-methyl-thiazol-2-yl]-[3-methoxy-4-(4-methyl-imidazol-1-yl)-phenyl]-amine,
[5-(4-chloro-benzyl)-4-methyl-thiazol-2-yl]-[3-methoxy-4-(4-methyl-imidazol-1-yl)-phenyl]-amine,
5-[5-(3-chloro-benzyl)-4-methyl-thiazol-2-ylamino]-2-(4-methyl-imidazol-1-yl)-benzonitrile,
[4-(5-bromo-2-methoxy-phenyl)-thiazol-2-yl]-[3-methoxy-4-(4-methyl-imidazol-1-yl)-phenyl]-amine,
[4-(5-bromo-2-methoxy-phenyl)-thiazol-2-yl]-[4-(4-methyl-imidazol-1-yl)-phenyl]-amine,
[4-(5-bromo-2-methoxy-phenyl)-thiazol-2-yl]-(4-imidazol-1-yl-3-methoxy-phenyl)-amine,
N-(4-fluoro-phenyl)-2-{2-[3-methoxy-4-(4-methyl-imidazol-1-yl)-phenylamino]-thiazol-4-yl}-acetamide,
((S)-1-{2-[3-methoxy-4-(4-methyl-imidazol-1-yl)-phenylamino]-thiazol-4-yl}-3-methyl-butyl)-carbamic acid tert-butyl ester,
2-(4-fluoro-phenyl)-N—((S)-1-{2-[3-methoxy-4-(4-methyl-imidazol-1-yl)-phenylamino]-thiazol-4-yl}-3-methyl-butyl)-acetamide,
4-fluoro-N—((S)-1-{2-[3-methoxy-4-(4-methyl-imidazol-1-yl)-phenylamino]-thiazol-4-yl}-3-methyl-butyl)-benzamide,
3,3,3-trifluoro-N—((S)-1-{2-[3-methoxy-4-(4-methyl-imidazol-1-yl)-phenylamino]-thiazol-4-yl}-3-methyl-butyl)-propionamide,
4-fluoro-N—((S)-1-{2-[3-methoxy-4-(4-methyl-imidazol-1-yl)-phenylamino]-thiazol-4-yl}-3-methyl-butyl)-benzenesulfonamide,
N—((S)-1-{2-[3-methoxy-4-(4-methyl-imidazol-1-yl)-phenylamino]-thiazol-4-yl}-3-methyl-butyl)-C-phenyl-methanesulfonamide,
N—((S)-1-{2-[3-methoxy-4-(4-methyl-imidazol-1-yl)-phenylamino]-thiazol-4-yl}-3-methyl-butyl)-methanesulfonamide,
2-[3-methoxy-4-(4-methyl-imidazol-1-yl)-phenylamino]-4-trifluoromethyl-thiazole-5-carboxylic acid ethyl ester,
N—((S)-1-{2-[3-methoxy-4-(4-methyl-imidazol-1-yl)-phenylamino]-thiazol-4-yl}-2-phenyl-ethyl)-4-methyl-benzenesulfonamide
{2-[3-methoxy-4-(4-methyl-imidazol-1-yl)-phenylamino]-thiazol-5-yl}-phenyl-methanol (4-chloro-phenyl)-{2-[3-methoxy-4-(4-methyl-imidazol-1-yl)-phenylamino]-thiazol-5-yl}-methanol
{4-[1-(4-chloro-phenyl)-1-methyl-ethyl]-thiazol-2-yl}-[3-methoxy-4-(4-methyl-imidazol-1-yl)-phenyl]-amine and
[3-methoxy-4-(4-methyl-imidazol-1-yl)-phenyl]-{4-[1-methyl-1-(3,4,5-trifluoro-phenyl)-ethyl]-thiazol-2-yl}-amine.

Preferred compounds of formula I-A-1 are further those, wherein
$R^1$ is hydrogen or lower alkoxy;
$R^2$ and $R^3$ are each independently lower alkyl or benzyl which is unsubstituted or substituted by one or more halogen, cyano, lower alkyl, lower alkyl substituted by halogen or lower alkoxy substituted by halogen and
$R^5$ is lower alkyl;
or pharmaceutically active acid addition salts, for example
4-{2-[3-methoxy-4-(4-methyl-imidazol-1-yl)-phenylamino]-4-methyl-thiazol-5-ylmethyl}-benzonitrile,
[5-(2-chloro-benzyl)-4-methyl-thiazol-2-yl]-[3-methoxy-4-(4-methyl-imidazol-1-yl)-phenyl]-amine,
[5-(4-tert-butyl-benzyl)-4-methyl-thiazol-2-yl]-[3-methoxy-4-(4-methyl-imidazol-1-yl)-phenyl]-amine
[3-methoxy-4-(4-methyl-imidazol-1-yl)-phenyl]-[4-methyl-5-(3-trifluoromethyl-benzyl)-thiazol-2-yl]-amine
[5-(4-chloro-3-trifluoromethyl-benzyl)-4-methyl-thiazol-2-yl]-[3-methoxy-4-(4-methyl-imidazol-1-yl)-phenyl]-amine
[3-methoxy-4-(4-methyl-imidazol-1-yl)-phenyl]-{4-methyl-5-[3-(1,1,2,2-tetrafluoro-ethoxy)-benzyl]-thiazol-2-yl}-amine

[5-(3-chloro-4-methyl-benzyl)-4-methyl-thiazol-2-yl]-[3-methoxy-4-(4-methyl-imidazol-1-yl)-phenyl]-amine and
[5-(3,4-dichloro-benzyl)-4-methyl-thiazol-2-yl]-[3-methoxy-4-(4-methyl-imidazol-1-yl)-phenyl]-amine.

Further preferred are compounds of formula I-A-2

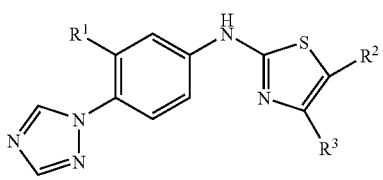

I-A-2 wherein
$R^1$ is hydrogen, lower alkoxy or cyano;
$R^2$ and $R^3$ are each independently hydrogen,
  lower alkyl,
  lower alkyl substituted by halogen,
  CHO,
  phenyl or —CRR'-phenyl, wherein the phenyl rings are unsubstituted or substituted by one or more halogen, cyano, lower alkyl, lower alkyl substituted by halogen, lower alkoxy substituted by halogen or lower alkoxy,
  —C(O)O-lower alkyl,
  —CH$_2$—C(O)O-lower alkyl,
  —CH$_2$—C(O)-piperidin-1-yl,
  —CH$_2$—C(O)NH-lower alkyl,
  —CH$_2$—C(O)NH-phenyl optionally substituted by halogen,
  —CHR—NHC(O)O-lower alkyl,
  —CHR—NH$_2$,
  —CHR—NH—CH$_2$-phenyl optionally substituted by halogen,
  —CHR—NH—(CH$_2$)$_2$-phenyl optionally substituted by halogen,
  —CHR—NH-phenyl optionally substituted by halogen,
  —CHR—NH-cycloalkyl,
  —CHR—NHC(O)—CH$_2$-phenyl optionally substituted by halogen,
  —CHR—NHC(O)—CH$_2$O-lower alkyl,
  —CHR—NHC(O)-lower alkyl,
  —CHR—NHC(O)O-lower alkyl substituted by halogen,
  —CHR—NHC(O)-phenyl optionally substituted by halogen,
  —CHR—NHCH$_2$CH$_2$O-lower alkyl,
  —CHR—NH—S(O)$_2$-phenyl optionally substituted by halogen or lower alkyl,
  —CHR—NH—S(O)$_2$—CH$_2$-phenyl optionally substituted by halogen,
  —CHR—NH—S(O)$_2$-lower alkyl,
  —CH$_2$-piperidin-1-yl,
  —CH$_2$-morpholinyl or
  -indole-2-carboxylic acid-(3,4-difluoro-phenyl)amide; and
R and R' are each independently hydrogen, lower alkyl, benzyl or hydroxy;
or pharmaceutically active acid addition salts.

Preferred are further compounds of formula

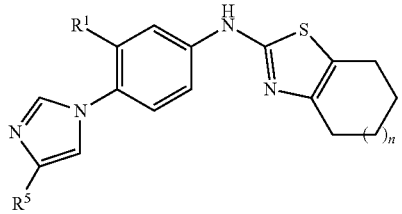

I-B-1

$R^1$ is hydrogen, lower alkoxy or cyano;
$R^5$ is hydrogen or lower alkyl; and
n is 0 or 1;
or pharmaceutically active acid addition salts Especially preferred are compounds of formula I-B-1, wherein $R^1$ is lower alkoxy, $R^5$ is lower alkyl and n is 0 or 1, for example the following compounds
[3-methoxy-4-(4-methyl-imidazol-1-yl)-phenyl]-(4,5,6,7-tetrahydro-benzothiazol-2-yl)-amine and
(5,6-dihydro-4H-cyclopentathiazol-2-yl)-[3-methoxy-4-(4-methyl-imidazol-1-yl)-phenyl]-amine.

Preferred are further compounds of formula I-C-1

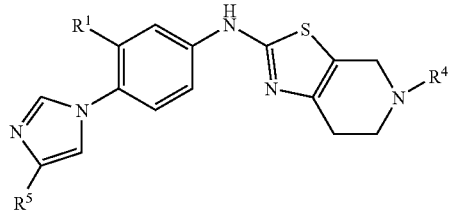

I-C-1 wherein
$R^1$ is lower alkoxy;
$R^4$ is hydrogen,
  —C(O)O-lower alkyl,
  —C(O)-phenyl optionally substituted by halogen,
  —C(O)-lower alkyl substituted by halogen,
  —C(O)-lower alkyl,
  —S(O)$_2$-phenyl optionally substituted by halogen,
  —S(O)$_2$-lower alkyl,
  —S(O)$_2$—CH$_2$-phenyl,
  benzyl optionally substituted by halogen,
  —CH$_2$—CH$_2$-phenyl,
  —C(O)—CH$_2$-phenyl optionally substituted by halogen or
  —C(O)—CH$_2$-lower alkoxy; and
$R^5$ is hydrogen or lower alkyl;
or pharmaceutically active acid addition salts, for example
2-[3-mthoxy-4-(4-methyl-imidazol-1-yl)-phenylamino]-6,7-dihydro-4H-thiazolo[5,4-c]pyridine-5-carboxylic acid tert-butyl ester,
[3-mthoxy-4-(4-methyl-imidazol-1-yl)-phenyl]-(4,5,6,7-tetrahydro-thiazolo[5,4-c]pyridin-2-yl)-amine trihydrochloride,
(4-fluoro-phenyl)-{2-[3-methoxy-4-(4-methyl-imidazol-1-yl)-phenylamino]-6,7-dihydro-4H-thiazolo[5,4-c]pyridin-5-yl}-methanone,
3,3,3-trifluoro-1-{2-[3-methoxy-4-(4-methyl-imidazol-1-yl)-phenylamino]-6,7-dihydro-4H-thiazolo[5,4-c]pyridin-5-yl}-propan-1-one,
1-{2-[3-methoxy-4-(4-methyl-imidazol-1-yl)-phenylamino]-6,7-dihydro-4H-thiazolo[5,4-c]pyridin-5-yl}-2,2-dimethyl-propan-1-one,

[5-(4-fluoro-benzenesulfonyl)-4,5,6,7-tetrahydro-thiazolo [5,4-c]pyridin-2-yl]-[3-methoxy-4-(4-methyl-imidazol-1-yl)-phenyl]-amine, (5-methanesulfonyl-4,5,6,7-tetrahydro-thiazolo[5,4-c]pyridin-2-yl)-[3-methoxy-4-(4-methyl-imidazol-1-yl)-phenyl]-amine,

[3-methoxy-4-(4-methyl-imidazol-1-yl)-phenyl]-(5-phenyl-methanesulfonyl-4,5,6,7-tetrahydro-thiazolo[5,4-c]pyridin-2-yl)-amine,

[5-(4-fluoro-benzyl)-4,5,6,7-tetrahydro-thiazolo[5,4-c]pyridin-2-yl]-[3-methoxy-4-(4-methyl-imidazol-1-yl)-phenyl]-amine,

[3-methoxy-4-(4-methyl-imidazol-1-yl)-phenyl]-(5-phenethyl-4,5,6,7-tetrahydro-thiazolo[5,4-c]pyridin-2-yl)-amine, 2-(4-fluoro-phenyl)-1-{2-[3-methoxy-4-(4-methyl-imidazol-1-yl)-phenylamino]-6,7-dihydro-4H-thiazolo[5,4-c]pyridin-5-yl}-ethanone and 2-methoxy-1-{2-[3-methoxy-4-(4-methyl-imidazol-1-yl)-phenylamino]-6,7-dihydro-4H-thiazolo[5,4-c]pyridin-5-yl}-ethanone.

The present compounds of formula I and their pharmaceutically acceptable salts can be prepared by methods known in the art, for example, by processes described below, which processes comprise a) reacting a compound of formula

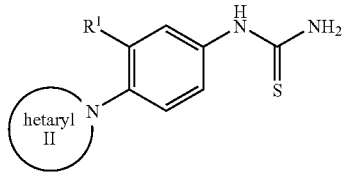

II with a compound of formula

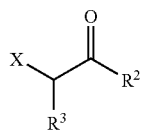

III to obtain a compound of formula

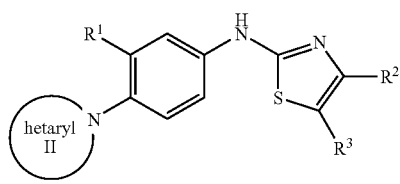

I-A wherein the substituents have the meaning as described above and, if desired, converting the compounds obtained into pharmaceutically acceptable acid addition salts;

or b) reacting a compound of formula

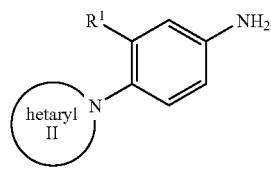

IV with a compound of formula

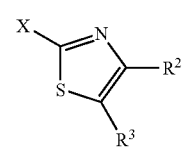

V to obtain a compound of formula

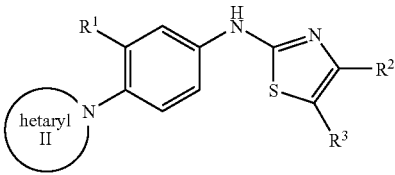

I-A wherein the substituents have the meaning as described above and X is halogen, and, if desired converting the compounds obtained into pharmaceutically acceptable acid addition salts; or c) reacting a compound of formula

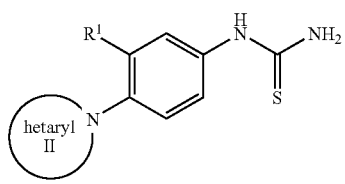

II with a compound of formula

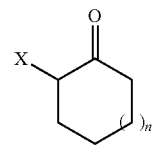

VI to obtain a compound of formula

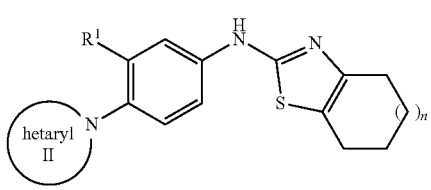

I-B wherein the substituents have the meaning as described above and, if desired, converting the compounds obtained into pharmaceutically acceptable acid addition salts; or d) reacting a compound of formula

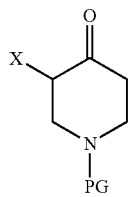

II with a compound of formula

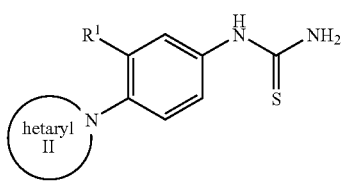

VII to obtain a compound of formula

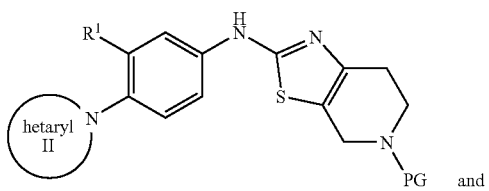

I-a and deprotecting a compound of formula I-a and, if desired, aminating, alkylating, acylating or sulfonylating a compound of formula

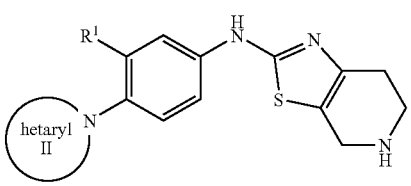

to obtain a compound of formula

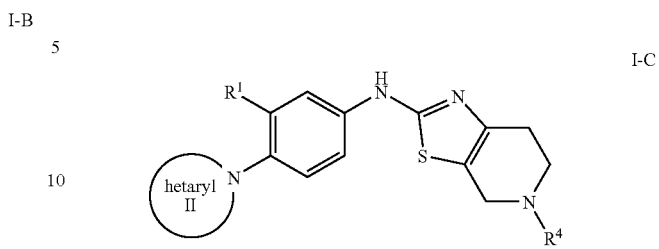

I-C wherein the substituents have the meaning as described above and, if desired, converting the compounds obtained into pharmaceutically acceptable acid addition salts;

The detailed description can be found below and in Examples 1-63. The aniline IV respectively the thiourea II, which can be used as starting materials for the preparation of compound I, can be prepared as described in Scheme 1. Nucleophilic substitution at room temperature or elevated temperature (e.g reflux or under pressure using a microwave oven) under neutral or basic conditions in the presence of a base (like e.g. potassium carbonate etc.) neat or in a polar solvent (like e.g. THF or DMSO etc.) of a substituted 4-nitrophenyl halide II with a 5-membered heteroaromatic ring (like e.g. imidazol preferred 5-methyl imidazol) yields the nitro derivative X which is reduced either under catalytic conditions (like e.g. 10% carbon on palladium) with hydrogen in a solvent (like e.g. ethanol or ethyl acetate) or with a metal (like e.g. iron) or metal salt (like e.g. stannous chloride) in a polar solvent (like e.g. acetic acid or tetrahydrofurane) to the aniline derivative IV. Alternatively aniline IV can be prepared from the corresponding N-protected 4-halo-aniline XI and the 5-membered heteroaromatic ring IX under catalytic conditions (like e.g. palladium(0) or copper(II) catalysis) after subsequent deprotection. The aniline IV can be converted to the thiourea II either by treatment with a thiophosgene derivative (like e.g. 1,1'-thiocarbonyldi-2(1H)-pyridone) and subsequent aminolysis or by treatment with an acyl isothiocyanate (like e.g. benzoyl isothiocyanate) and subsequent hydrolysis.

Scheme 1

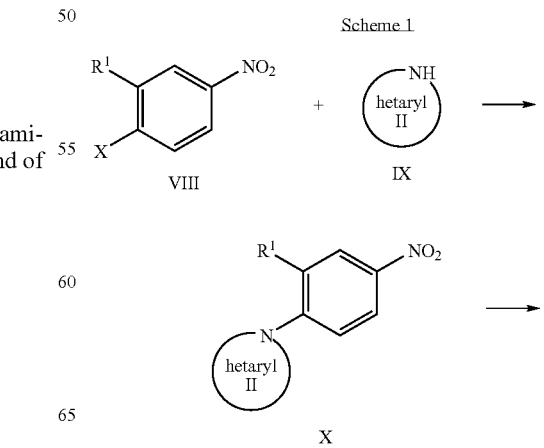

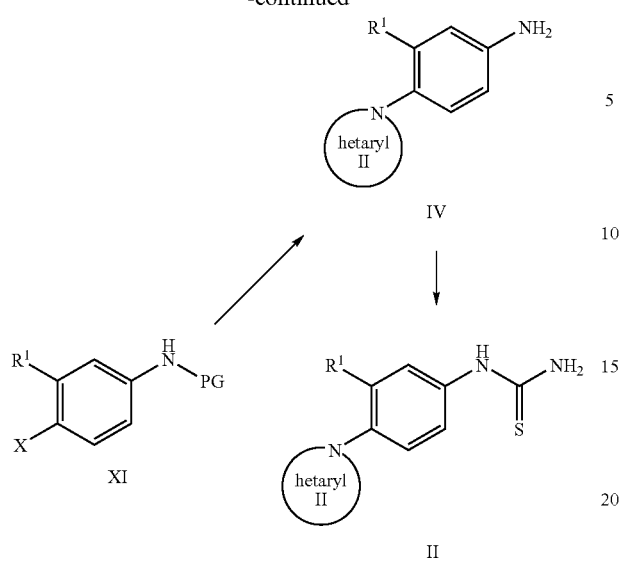

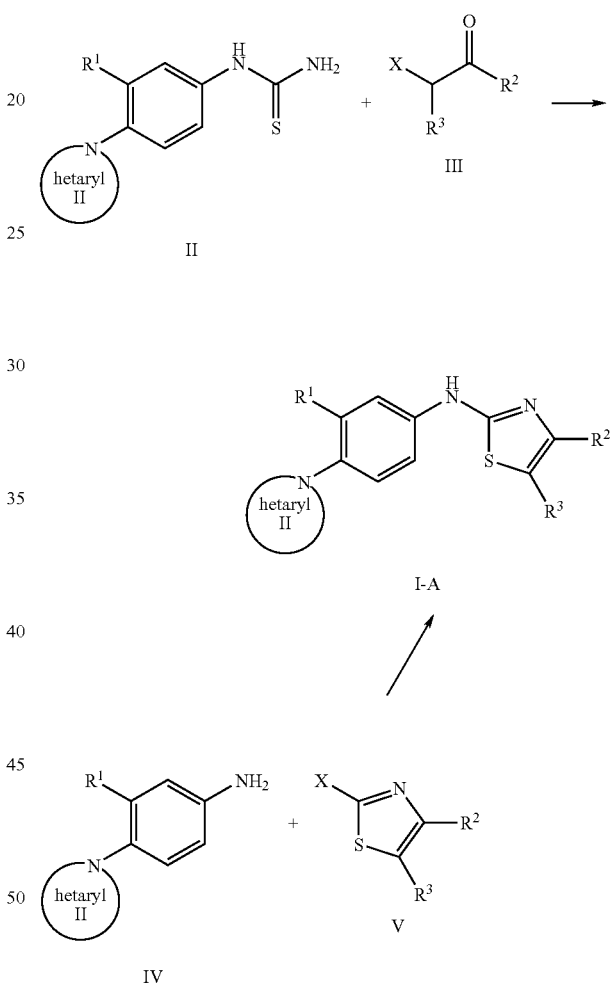

Alpha-halo-ketones III can be prepared from the corresponding ketones XII through halogenation with either elemental halogen or a halide transferring agent (like e.g. NXS etc.). Treatment of the carboxylic ester XIII (R=e.g. alkyl preferable methyl) with lithiated bromomethane at low temperature in an inert solvent (like e.g. tetrahydrofurane) yields the alpha-bromo-ketone III (X=Br). Alternatively the alpha-bromo-ketone III (X=Br) can be prepared from the acid XIII (X=H) through activation to the corresponding acid chloride or anhydride (e.g. with iPrOCO), treatment with diazomethane or trimethylsilyldiazomethane and subsequent decomposition with HBr in an inert solvent.

The alpha-chloroketone XV can be prepared in one pot from the corresponding aniline and the alpha,beta-unsaturated ketone via the Meerwein reaction through diazotation with a diazotation reagent (like e.g. tBuONO) and treatment with copper(II) chloride in an inert solvent (like e.g. acetonitrile) at low or elevated temperatures. Alternatively alpha-chloroketone XV can be prepared from the corresponding 2-benzyl-betaketoester through alpha chlorination with a chlorination agent (like NCS or sulfuryl chloride) and subsequent acidic keton cleavage (as described in Mcphee, W. D.; Klingsberg, E. J. Am Chem. Soc. (1944) 66, 1132 and Yang D., Yan Y. L., Lui B. J. Org. Cem. 67 (21) 7429 (2002).).

Scheme 2

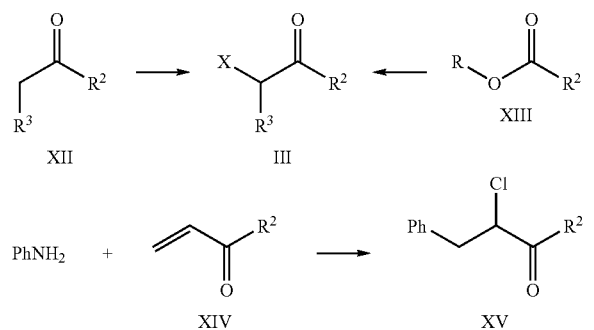

Ph may be substituted as described in the definitions for $R^2/R^3$.

Condensation of the thiourea II with the alpha-halo- or alpha-sulfoxy-ketones III or XV in an inert solvent (like e.g. ethanol) at room temperature or elevated temperature in the presence or absence of a base (like e.g. potassium carbonate or Hütnigs base) yields the aminothiazoles I as outlined in Scheme 3. Alternatively compounds of structure I can also be prepared through direct amination of a suitable 2-halo-thiazole V with the aniline IV in the presence of a catalyst and a ligand (like e.g. palladium(0) and a phosphine ligand or copper(II) and a phenanthrene ligand).

Scheme 3

Annulated aminothiazol derivatives I-B or I-C can be obtained by the condensation of the thiourea II with the corresponding cyclic alpha-halo- or alpha-sulfoxy-ketones VI in an inert solvent (like e.g. ethanol) at room temperature or elevated temperature in the presence or absence of a base (like e.g. potassium carbonate or Hütnigs base) as outlined in Scheme 4. When using the corresponding piperidine derivative the amino group has to be protected (for example with the tert.-butyloxycarbonyl group) prior to the condensation. After successful condensation the protective group (PG) can be removed and replaced by other substituents through reductive amination, alkylation, acylation or sulfonylation.

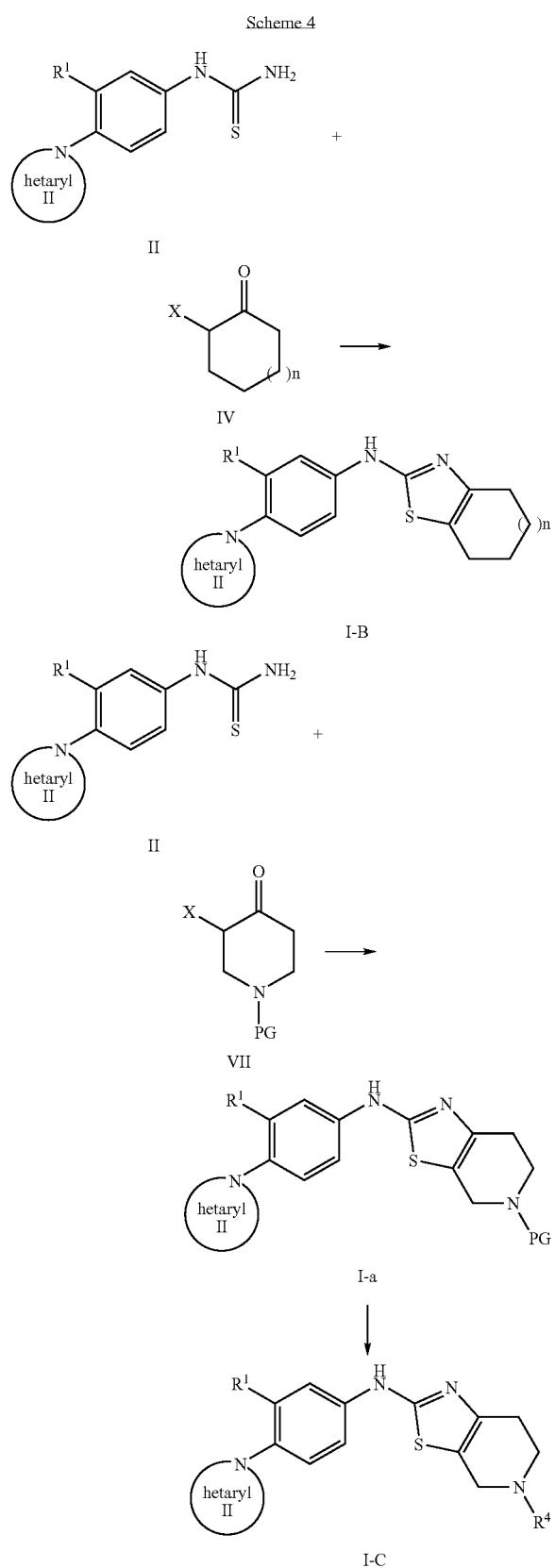

Scheme 4

The compounds were investigated in accordance with the test given hereinafter.

Description of γ-Secretase Assay

Cellular γ-Secretase Assay

Human neuroglioma H4 cells overexpressing human APP were plated at 30,000 cells/well/200 µl in 96-well plates in IMDM media containing 10% FCS, 0.2 mg/l Hygromycin B and incubated for 2 h at 37° C., 5% CO2 prior to adding test compounds.

Compounds for testing were dissolved in 100% $Me_2SO$ yielding in a 10 mM stock solution.

Typically 12 µl of these solutions were further diluted in 1000 µl of IMDM media (w/o FCS,). Sub sequential 1:1 dilutions gave a ten point dose response curve. 100 µl of each dilution was added to the cells in 96-well plates. Appropriate controls using vehicle only and reference compound were applied to this assay. The final concentration of $Me_2SO$ was 0.4%.

After incubation for 22 hrs at 37° C., 5% $CO_2$, 50 µl supernatant was transferred into round-bottom 96-well polypropylene plates for detection of Aβ42. 50 µl assay buffer (50 mM Tris/Cl, pH 7.4, 60 mM NaCl, 0.5% BSA, 1% TWEEN 20) was added to the wells followed by the addition of 100 µl of detection antibody (ruthenylated BAP15 0.0625 µg/ml in assay buffer). 50 µl of a premix of capture antibody (biotinylated 6E10 antibody, 1 µg/ml) and Steptavidin-coated magnetic beads (Dynal M-280, 0.125 mg/ml) were preincubated for 1 hr at room temperature before adding the assay plates. Assay plates were incubated on a shaker for 3 hrs at room temperature and finally read in the Bioveris M8 Analyser according to the manufacturer's instructions (Bioveris).

Toxicity of compounds was monitored by a cell viability test of the compound-treated cells using a calorimetric assay (CellTiter 96™ AQ assay, Promega) according to the manufacturer's instructions. Briefly, after removal of 50 µl cell culture supernatant for detection of Aβ42, 20 µl of 1×MTS/PES solution was added to the cells and incubated for 30 min at 37° C., 5% $CO_2$. Optical density was then recorded at 490 nm.

$IC_{50}$ values for inhibition of Aβ42 secretion were calculated by nonlinear regression fit analysis using XLfit 4.0 software (IDBS).

The preferred compounds show a $IC_{50}$<1.0 (µM). In the list below are described the data to the inhibition of Aβ42 secretion:

| Example No. | $IC_{50}$ in vitro (µM) |
|---|---|
| 1 | 0.21 |
| 2 | 0.24 |
| 4 | 0.75 |
| 6 | 0.87 |
| 7 | 0.52 |
| 8 | 0.57 |
| 9 | 0.92 |
| 16 | 0.9 |
| 21 | 0.88 |
| 22 | 0.79 |
| 29 | 0.95 |
| 30 | 0.39 |
| 34 | 0.52 |
| 37 | 0.41 |
| 38 | 0.29 |
| 39 | 0.91 |
| 40 | 0.55 |
| 41 | 0.9 |
| 42 | 0.64 |

-continued

| Example No. | IC$_{50}$ in vitro (μM) |
|---|---|
| 43 | 0.79 |
| 55 | 0.8 |
| 62 | 0.57 |
| 68 | 0.89 |
| 69 | 0.73 |
| 70 | 0.71 |
| 71 | 0.28 |
| 76 | 0.34 |
| 77 | 0.14 |
| 78 | 0.68 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Item | Ingredients | Tablet Formulation (Wet Granulation) mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Item | Ingredients | Capsule Formulation mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

[5-(3-Chloro-benzyl)-4-methyl-thiazol-2-yl]-[3-methoxy-4-(4-methyl-imidazol-1-yl)-phenyl]-amine a) 1-(2-Methoxy-4-nitro-phenyl)-4-methyl-1H-imidazole A solution of 187 mg (1 mmol) 2-chloro-5-nitroanisol, 335 mg (4 mmol) 4-methylimidazol and 99 mg (1.5 mmol) potassium hydroxide in DMSO (0.86 ml) was stirred for 5 hours at 80° under an atmosphere of nitrogen. After cooling to room temperature the reaction was poured onto ice/water. A precipitation was formed and the suspension was stirred for 15 minutes. The solid was filtered off, washed with water, dissolved in methylene chloride, dried over sodium sulphate, filtered and the solvent was evaporated under reduced pressure to yield a yellow solid. The crude product was purified on silica gel with methylene chloride/methanol 19/1 yielding 106 mg (45%) 1-(2-methoxy-4-nitro-phenyl)-4-methyl-1H-imidazole as a light yellow solid. Alternatively the product can be also crystallized from the crude material from diethyl ether. MS ISP (m/e): 234.3 (100) (M+H)$^+$. $^1$H NMR (CDCl$_3$, 250 MHz):δ (ppm)=7.97 (d, 1H), 7.96 (s, 1H), 7.83 (s, 1H), 7.42 (d, 1H), 7.00 (s, 1H), 4.00 (s, 3H), 2.31 (s, 3H).

b) 3-Methoxy-4-(4-methyl-imidazol-1-yl)-phenylamine 2520 mg (10.8 mmol) 1-(2-methoxy-4-nitro-phenyl)-4-methyl-1H-imidazole dissolved in ethanol (110 ml) was hydrated under an atmosphere of hydrogen at room temperature for 3½ hours in the presence of 252 mg of 10% palladium on charcoal. The catalyst was filtered off and washed with ethanol. The solvent of the filtrate was evaporated under reduced pressure. The crude product was purified on silica gel with methylene chloride/methanol 19/1. The fraction containing the product was suspended in diethyl ether, stirred for 15 minutes, filtered and dried to yield 1719 mg (78%) 3-methoxy-4-(4-methyl-imidazol-1-yl)-phenylamine as a yellow solid. MS ISP (m/e): 204.3 (100) (M+H)$^+$. $^1$H NMR (CDCl$_3$, 250 MHz): δ (ppm)=7.48 (s, 1H), 6.91 (d, 1H), 6.88 (s, 1H), 6.35 (s, 1H), 6.17 (d, 1H), 3.68 (s, 3H), 2.11 (s, 3H).

c) 1-(4-Isothiocyanato-2-methoxy-phenyl)-4-methyl-1H-imidazole

A solution of 203 mg (1 mmol) of 3-methoxy-4-(4-methyl-imidazol-1-yl)-phenylamine and of 263 mg (1.1 mmol) of 1,1'-thiocarbonyldi-2(1H)-pyridone in methylene chloride (10 ml) was stirred at room temperature over night to yield an orange solution. The reaction was concentrated under reduced pressure to ¼ of its volume and directly purified on silica gel with methylene chloride/methanol 95/5 yielding 230 mg (94%) 1-(4-isothiocyanato-2-methoxy-phenyl)-4-methyl-1H-imidazole as a yellow oil, which solidifies on standing. MS ISP (m/e): 246.3 (100) (M+H)$^+$. $^1$H NMR (CDCl$_3$, 250 MHz): δ (ppm)=7.67 (s, 1H), 7.21 (d, 1H), 6.91-6.86 (m, 3H), 3.86 (s, 3H), 2.29 (s, 3H).

d) [3-Methoxy-4-(4-methyl-imidazol-1-yl)-phenyl]-thiourea 227 mg (0.93 mmol) 1-(4-isothiocyanato-2-methoxy-phenyl)-4-methyl-1H-imidazole was dissolved in tetrahydrofurane (2.3 ml). At 0° C. under stirring ammonia gas was bubbled through the solution for 5 minutes. A solid precipitated. The suspension was stirred at room temperature over night. The solvent was evaporated under reduced pressure and the residue was stirred with diethyl ether for 30 minutes. The solid was filtered off and dried yielding 170 mg (70%) [3-methoxy-4-(4-methyl-imidazol-1-yl)-phenyl]-thiourea as a light yellow solid. MS ISP (m/e): 263.3 (100) (M+H)$^+$. $^1$H NMR (DMSO-D$_6$, 250 MHz): δ (ppm)=9.84 (s, 1H), 7.90-7.20 (br s, 2H), 7.71 (s, 1H), 7.46 (s, 1H), 7.28 (d, 1H), 7.07 (s, 1H), 7.03 (d, 1H), 3.79 (s, 3H), 2.15 (s, 3H).

e) [5-(3-Chloro-benzyl)-4-methyl-thiazol-2-yl]-[3-methoxy-4-(4-methyl-imidazol-1-yl)-phenyl]-amine A suspension of 78.7 mg (0.3 mmol) [3-methoxy-4-(4-methyl-imidazol-1-yl)-phenyl]-thiourea and of 71.6 mg (0.33 mmol) of 3-chloro-4-(3-chlorophenyl)-2-butanone in ethanol (3 ml) was heated over night to reflux to yield a yellow solution. After cooling to room temperature the solvent was evaporated under reduced pressure and the residue was purified on silica gel with methylene chloride/methanol 19/1 yielding 55 mg (43%) [5-(3-chloro-benzyl)-4-methyl-thiazol-2-yl]-[3-methoxy-4-(4-methyl-imidazol-1-yl)-phenyl]-amine as a yellow solid. MS ISP (m/e): 425.1/427.2 (100/43) (M+H)$^+$. $^1$H NMR (DMSO-D$_6$, 250 MHz): δ (ppm)=10.16 (s, 1H), 7.64 (s, 1H), 7.53 (s, 1H), 7.35-7.19 (m, 6H), 7.01 (s, 1H), 4.01 (s, 2H), 3.78 (s, 3H), 2.24 (s, 3H), 2.14 (s, 3H).

EXAMPLE 2

[5-(4-Chloro-benzyl)-4-methyl-thiazol-2-yl]-[3-methoxy-4-(4-methyl-imidazol-1-yl)-phenyl]-amine The title compound was prepared in analogy to example 1 step e) from 72 mg (0.33 mmol) 3-chloro-4-(4-chlorophenyl)-2-butanone and 79 mg (0.3 mmol) [3-methoxy-4-(4-methyl-imidazol-1-yl)-phenyl]-thiourea. The crude product was purified on silica gel with methylene chloride/methanol 9/1 yielding 78 mg (61%) [5-(4-chloro-benzyl)-4-methyl-thiazol-2-yl]-[3-methoxy-4-(4-methyl-imidazol-1-yl)-phenyl]-amine as a light brown solid. MS ISP (m/e): 425.1/427.1 (100/42) (M+H)$^+$. $^1$H NMR (DMSO-D$_6$, 250 MHz): δ (ppm)=10.15 (s, 1H), 7.64 (s, 1H), 7.52 (s, 1H), 7.37 (d, 2H), 7.26 (d, 2H), 7.23 (s, 2H), 3.98 (s, 2H), 3.77 (s, 3H), 2.23 (s, 3H), 2.14 (s, 3H).

EXAMPLE 3

[5-(3-Chloro-benzyl)-4-ethyl-thiazol-2-yl]-[3-methoxy-4-(4-methyl-imidazol-1-yl)-phenyl]-amine a) 2-Chloro-1-(3-chloro-phenyl)-pentan-3-one To a suspension of 333 mg (2.4 mmol) copper(II) chloride in acetonitrile (2 ml) 1041 mg (12 mmol) ethyl vinylketone and 344 mg (3 mmol) tert.-butylnitrite were added at room temperature. 258 mg (2 mmol) 3-chloroaniline was added slowly. The reaction turned warm and a gas evolved. The reaction was stirred for 30 minutes at room temperature. 25% Aqueous HCl solution was added and the reaction was extracted twice with diethyl ether. The combined organic layers were washed once with 25% aqueous HCl solution and stirred for 10 minutes at room temperature with 314 mg (2 mmol) DBU. A solid precipitated. The reaction was washed once with 25% aqueous HCl solution and once with brine, dried over sodium sulphate, filtered and the solvent was evaporated under reduced pressure. The crude product was subjected to high vacuo to yield 357 mg (77%) 2-chloro-1-(3-chloro-phenyl)-pentan-3-one as an orange oil. The crude product was used without further purification in the next step. $^1$H NMR (DMSO-D$_6$, 250 MHz): δ (ppm)=7.26-7.22 (m, 3H), 7.10 (s, 1H), 4.40 (dd, 1H), 3.33 (dd, 1H), 3.04 (dd, 1H), 2.72 (dq, 1H), 2.53 (dq, 1H), 1.07 (t, 3H).

b) [5-(3-Chloro-benzyl)-4-ethyl-thiazol-2-yl]-[3-methoxy-4-(4-methyl-imidazol-1-yl)-phenyl]-amine The title compound was prepared in analogy to example 1 step e) from 76 mg (0.33 mmol) 2-chloro-1-(3-chloro-phenyl)-pentan-3-one and 79 mg (0.3 mmol) [3-methoxy-4-(4-methyl-imidazol-1-yl)-phenyl]-thiourea. The crude product was purified on silica gel with methylene chloride/methanol 19/1 yielding 62 mg (47%) [5-(4-chloro-benzyl)-4-ethyl-thiazol-2-yl]-[3-methoxy-4-(4-methyl-imidazol-1-yl)-phenyl]-amine as a light brown viscous oil. MS ISP (m/e): 439.2/441.2 (100/40) (M+H)$^+$. $^1$H NMR (DMSO-D$_6$, 250 MHz): δ (ppm)=10.19 (s, 1H), 7.74 (s, 1H), 7.64 (s, 1H), 7.35-7.18 (m, 5H), 7.10 (d, 1H), 7.02 (s, 1H), 4.02 (s, 2H), 3.79 (s, 3H), 2.56 (q, 2H), 2.14 (s, 3H), 1.20 (t, 3H).

EXAMPLE 4

5-[5-(3-Chloro-benzyl)-4-methyl-thiazol-2-ylamino]-2-(4-methyl-imidazol-1-yl)-benzonitrile a) 2-(4-Methyl-imidazol-1-yl)-5-nitro-benzonitrile A suspension of 831 mg (5 mmol) of 3-cyano-4-fluoronitrobenzene, of 821 mg (10 mmol) 4-methylimidazol and of 1382 mg (10 mmol) potassium carbonate in acetonitrile (10 ml) was stirred over the weekend at room temperature. The solvent was evaporated and the residue was partitioned between ethyl acetate and 1N aqueous NaOH solution. The aqueous layer was extracted with ethyl acetate. The combined organic layers were washed with brine, dried over sodium sulphate, filtered and the solvent was evaporated under reduced pressure. The crude product was crystallized from ethanol/water yielding 650 mg (57%) 2-(4-methyl-imidazol-1-yl)-5-nitro-benzonitrile as an off-white solid. $^1$H NMR (DMSO-D$_6$, 250 MHz): δ (ppm)=8.95 (s, 1H), 8.62 (d, 1H), 8.16 (s, 1H), 7.93 (d, 1H), 7.49 (s, 1H), 2.21 (s, 3H).

b) 5-Amino-2-(4-methyl-imidazol-1-yl)-benzonitrile 650 mg (2.84 mmol) 2-(4-methyl-imidazol-1-yl)-5-nitrobenzonitrile dissolved in ethyl acetate (10 ml) were hydrated under an atmosphere of hydrogen at room temperature for 5 hours in the presence of 150 mg of 10% palladium on charcoal. The catalyst was filtered off and washed with ethyl acetate. The solvent of the filtrate was evaporated under reduced pressure and dried to yield 450 mg (80%) 5-amino-2-(4-methyl-imidazol-1-yl)-benzonitrile as a yellow solid. MS ISP (m/e): 199.1 (100) (M+H)$^+$. $^1$H NMR (DMSO-D$_6$, 250 MHz): δ (ppm)=7.72 (s, 1H), 7.23 (d, 1H), 7.10 (s, 1H), 6.96 (s, 1H), 6.91 (d, 1H), 2.15 (s, 3H).

c) [3-Cyano-4-(4-methyl-imidazol-1-yl)-phenyl]-thiourea

To a solution of 450 mg (2.27 mmol) 5-amino-2-(4-methyl-imidazol-1-yl)-benzonitrile in tetrahydrofurane (22 ml) 407 mg (2.5 mmol) benzoylisocyanate was added and the reaction was stirred at room temperature for 2 hours. The solvent was evaporated under reduce pressure and the residue was suspended in methanol (22 ml). A solution of 941 mg (6.8 mmol) potassium carbonate in water (16.5 ml) was added drop wise to the suspension. The reaction was stirred at room temperature over night to yield a solution, which was concentrated under reduced pressure. The residue was suspended in water, filtered, washed with water and diethyl ether. The solid was several times suspended in tetrahydrofurane, the solvent was evaporated under reduced pressure and dried under vacuum to yield 480 mg (82%) [3-cyano-4-(4-methyl-imidazol-1-yl)-phenyl]-thiourea as a light yellow solid. MS ISP (m/e): 241.1 (100) (M+H—NH$_3$)$^+$, 258.0 (85) (M+H)$^+$. $^1$H NMR (DMSO-D$_6$, 250 MHz): δ (ppm)=10.24 (br s, 1H), 8.22 (s, 1H), 7.92 (s, 1H), 7.87 (d, 1H), 7.57 (d, 1H), 7.28 (s, 1H), 2.18 (s, 3H).

d) 5-[5-(3-Chloro-benzyl)-4-methyl-thiazol-2-ylamino]-2-(4-methyl-imidazol-1-yl)-benzonitrile The title compound was prepared in analogy to example 1 step e) from 54 mg (0.25 mmol) 3-chloro-4-(3-chlorophenyl)-2-butanone and 64 mg (0.25 mmol) [3-cyano-4-(4-methyl-imidazol-1-yl)-phenyl]-thiourea. The crude product was purified on silica gel with methylene chloride/methanol 9/1 yielding 50 mg (48%) 5-[5-(3-chloro-benzyl)-4-methyl-thiazol-2-ylamino]-2-(4-methyl-imidazol-1-yl)-benzonitrile as a light yellow solid. MS ISP (m/e): 420.1/422.2 (100/38) (M+H)$^+$. $^1$H NMR (DMSO-D$_6$, 250 MHz): δ (ppm)=10.55 (s, 1H), 8.24 (s, 1H), 7.89 (s, 1H), 7.88 (d, 1H), 7.55 (d, 1H), 7.36-7.20 (m, 5H), 4.03 (s, 2H), 2.27 (s, 3H), 2.18 (s, 3H).

EXAMPLE 5

[5-(3-Chloro-benzyl)-4-methyl-thiazol-2-yl]-(4-[1,2,4]triazol-1-yl-phenyl)-amine A suspension of 55 mg (0.25 mmol) 4-(1,2,4-triazol-1-yl) phenylthiourea, of 60 mg (0.28 mmol) 3-chloro-4-(3-chlorophenyl)-2-butanone and of 65 mg (0.5 mmol) N,N-diisopropyl ethyl amine in ethanol (2.5 ml) was refluxed over night. The same amount of chloro ketone was added and the reaction was heated to reflux over night. Again 1.1 equivalent of chloro ketone was added and the reaction was heated for 10 minutes in a microwave oven to 170° C. The solvent was evaporated and the residue was purified on silica gel with methylene chloride/methanol 19/1 yielding 27 mg (28%) [5-(3-chloro-benzyl)-4-methyl-thiazol-2-yl]-(4-[1,2,4]triazol-1-yl-phenyl)-amine as a yellow solid. MS ISP (m/e): 382.1 (100) (M+H)$^+$. $^1$H NMR (CDCl$_3$, 250 MHz): δ (ppm)=8.48 (s, 1H), 8.09 (s, 1H), 7.60 (d, 2H), 7.46 (d, 2H), 7.25-7.18 (m, 3H), 7.09 (d, 1H), 3.96 (s, 2H), 2.29 (s, 3H).

EXAMPLE 6

4-{2-[3-Methoxy-4-(4-methyl-imidazol-1-yl)-phenylamino]-4-methyl-thiazol-5-ylmethyl}-benzonitrile a) 2-Chloro-1-(4-cyano-phenyl)-pentan-3-one The title compound was prepared in analogy to example 3 step a) from 354 mg (3 mmol) 4-aminophenylnitrile and 1262 mg (18 mmol) methyl vinylketone to yield 640 mg 2-chloro-1-(4-cyano-phenyl)-pentan-3-one as a 1:1 mixture with the Sandmeyer product 4-chlorobenzonitrile. The crude product was used without further purification in the next step.

b) 4-{2-[3-Methoxy-4-(4-methyl-imidazol-1-yl)-phenylamino]-4-methyl-thiazol-5-ylmethyl}-benzonitrile The title compound was prepared in analogy to example 1 step e) from 70 mg (0.2 mmol) 2-chloro-1-(3-chloro-phenyl)-pentan-3-one (60% purity), and 33 mg (0.13 mmol) [3-methoxy-4-(4-methyl-imidazol-1-yl)-phenyl]-thiourea. The crude product was purified on silica gel with methylene chloride/methanol 19/1 yielding 30 mg (58%) 4-{2-[3-methoxy-4-(4-methyl-imidazol-1-yl)-phenylamino]-4-methyl-thiazol-5-ylmethyl}-benzonitrile as a brown solid. MS ISP (m/e): 416.3 (100) (M+H)$^+$. $^1$H NMR (DMSO-D$_6$, 250 MHz): δ (ppm)= 10.20 (s, 1H), 7.79 (d, 2H), 7.65 (s, 1H), 7.52 (s, 1H), 7.43 (d, 2H), 7.01 (s, 1H), 4.10 (s, 2H), 3.78 (s, 3H), 2.23 (s, 3H), 2.14 (s, 3H).

EXAMPLE 7

[5-(2-Chloro-benzyl)-4-methyl-thiazol-2-yl]-[3-methoxy-4-(4-methyl-imidazol-1-yl)-phenyl]-amine The title compound was prepared in analogy to example 6 without purification of the intermediate from 128 mg (1 mmol) 2-chloroaniline and 421 mg (6 mmol) methyl vinylketone. The crude chloroketone was used without further purification in the next step with 53 mg (0.2 mmol) [3-methoxy-4-(4-methyl-imidazol-1-yl)-phenyl]-thiourea. The crude product was purified on silica gel with methylene chloride/methanol 19/1 yielding 40 mg (47%) [5-(2-chloro-benzyl)-4-methyl-thiazol-2-yl]-[3-methoxy-4-(4-methyl-imidazol-1-yl)-phenyl]-amine as a brown solid. MS ISP (m/e): 425.1/427.2 (100/44) (M+H)$^+$. $^1$H NMR (DMSO-D$_6$, 250 MHz): δ (ppm)=10.15 (s, 1H), 7.63 (s, 1H), 7.53 (s, 1H), 7.47-7.22 (m, 6H), 7.01 (s, 1H), 4.07 (s, 2H), 3.77 (s, 3H), 2.25 (s, 3H), 2.14 (s, 3H).

EXAMPLE 8

[5-(4-tert-Butyl-benzyl)-4-methyl-thiazol-2-yl]-[3-methoxy-4-(4-methyl-imidazol-1-yl)-phenyl]-amine The title compound was prepared in analogy to example 7 without purification of the intermediate from 149 mg (1 mmol) 4-tert-butylaniline and 421 mg (6 mmol) methyl vinylketone. The crude chloroketone was used without further purification in the next step with 53 mg (0.2 mmol) [3-methoxy-4-(4-methyl-imidazol-1-yl)-phenyl]-thiourea. The crude product was purified on silica gel with methylene chloride/methanol 19/1 yielding 45 mg (50%) of [5-(4-tert-butyl-benzyl)-4-methyl-thiazol-2-yl]-[3-methoxy-4-(4-methyl-imidazol-1-yl)-phenyl]-amine as a brown solid. MS ISP (m/e): 447.3 (100) (M+H)$^+$. $^1$H NMR (DMSO-D$_6$, 250 MHz): δ (ppm)=10.12 (s, 1H), 7.63 (s, 1H), 7.53 (s, 1H), 7.32

(d, 2H), 7.22 (s, 2H), 7.15 (d, 2H), 7.01 (s, 1H), 3.92 (s, 2H), 3.77 (s, 3H), 2.24 (s, 3H), 2.13 (s, 3H).

EXAMPLE 9

[3-Methoxy-4-(4-methyl-imidazol-1-yl)-phenyl]-[4-methyl-5-(3-trifluoromethyl-benzyl)-thiazol-2-yl]-amine The title compound was prepared in analogy to example 7 without purification of the intermediate from 161 mg (1 mmol) 3-trifluoromethylaniline and 421 mg (6 mmol) methyl vinylketone. The crude chloroketone was used without further purification in the next step with 53 mg (0.2 mmol) [3-methoxy-4-(4-methyl-imidazol-1-yl)-phenyl]-thiourea. The crude product was purified on silica gel with methylene chloride/methanol 19/1 yielding 50 mg (55%) [3-methoxy-4-(4-methyl-imidazol-1-yl)-phenyl]-[4-methyl-5-(3-trifluoromethyl-benzyl)-thiazol-2-yl]-amine as a brown solid. MS ISP (m/e): 459.1 (100) (M+H)$^+$. $^1$H NMR (DMSO-D$_6$, 250 MHz): δ (ppm)=10.18 (s, 1H), 7.66-7.53 (m, 7H), 7.23 (s, 1H), 7.01 (s, 1H), 4.11 (s, 2H), 3.77 (s, 3H), 2.25 (s, 3H), 2.14 (s, 3H).

EXAMPLE 10

[4-(4-Chloro-phenyl)-thiazol-2-yl]-[3-methoxy-4-(4-methyl-imidazol-1-yl)-phenyl]-amine a) 1-(4-Chloro-phenyl)-2-thiocyanato-ethanone A solution of 945 mg (5 mmol) 2,4'-dichloroacetophenone and 583 mg (6 mmol) potassium rhodanide was heated to reflux for 30 minutes. After a few minutes a precipitation was formed. The solvent was evaporated under reduced pressure and the residue was suspended in tetrahydrofurane, stirred for 1 hour at room temperature, filtered and the filtrate was concentrated in vacuo. The residue was stirred with heptane and little ethanol for 15 minutes. The product was filtered off and dried to yield 953 mg (90%) 1-(4-chloro-phenyl)-2-thiocyanato-ethanone as a light yellow solid. $^1$H NMR (CDCl$_3$, 250 MHz): δ (ppm)=7.89 (d, 2H), 7.51 (d, 2H), 4.692 (s, 2H).

b) [4-(4-Chloro-phenyl)-thiazol-2-yl]-[3-methoxy-4-(4-methyl-imidazol-1-yl)-phenyl]-amine A solution of 51 mg (0.25 mmol) 3-methoxy-4-(4-methyl-imidazol-1-yl)-phenylamine and of 53 mg (0.25 mmol) 1-(4-chloro-phenyl)-2-thiocyanato-ethanone in ethanol (1.25 ml) and dioxane (1.25 ml) was refluxed over night. After cooling to room temperature the solvent was evaporated under vacuo and the residue was purified on silica gel with methylene chloride/methanol 19/1 yielding 35 mg (35%) [4-(4-chloro-phenyl)-thiazol-2-yl]-[3-methoxy-4-(4-methyl-imidazol-1-yl)-phenyl]-amine as a yellow solid. MS ISP (m/e): 397.1/399.1 (100/50) (M+H)$^+$. $^1$H NMR (DMSO-D$_6$, 250 MHz): δ (ppm)=10.54 (s, 1H), 7.96 (d, 2H), 7.86 (s, 1H), 7.68 (s, 1H), 7.50 (d, 2H), 7.48 (s, 1H), 7.31 (d, 1H), 7.22 (d, 1H), 7.06 (s, 1H).

EXAMPLE 11

[3-Methoxy-4-(4-methyl-imidazol-1-yl)-phenyl]-[4-(2-methoxy-phenyl)-thiazol-2-yl]-amine The title compound was prepared in analogy to example 1 step e) from 77 mg (0.33 mmol) 2-bromo-2'-methoxyacetophenon and 79 mg (0.3 mmol) [3-methoxy-4-(4-methyl-imidazol-1-yl)-phenyl]-thiourea. The crude product was purified through stirring with methylene chloride at room temperature yielding 104 mg (88%) [3-methoxy-4-(4-methyl-imidazol-1-yl)-phenyl]-[4-(2-methoxy-phenyl)-thiazol-2-yl]-amine as a light yellow solid. MS ISP (m/e): 393.2 (100) (M+H)$^+$. $^1$H NMR (DMSO-D$_6$, 250 MHz): δ (ppm)=10.65 (s, 1H), 9.32 (s, 1H), 8.17 (d, 1H), 8.05 (s, 1H), 7.70 (s, 1H), 7.53 (d, 1H), 7.51 (s, 1H), 7.32-7.29 (m, 2H), 7.15 (d, 1H), 7.07 (t, 1H), 3.94 (s, 3H), 3.93 (s, 3H), 2.35 (s, 3H).

EXAMPLE 12

[4-(2-Fluoro-phenyl)-thiazol-2-yl]-[3-methoxy-4-(4-methyl-imidazol-1-yl)-phenyl]-amine The title compound was prepared in analogy to example 1 step e) from 72 mg (0.33 mmol) 2-fluorophenacylbromide and 79 mg (0.3 mmol) [3-methoxy-4-(4-methyl-imidazol-1-yl)-phenyl]-thiourea. The crude product was purified through stirring with methylene chloride at room temperature yielding 121 mg (99%) [4-(2-fluoro-phenyl)-thiazol-2-yl]-[3-methoxy-4-(4-methyl-imidazol-1-yl)-phenyl]-amine as a light green solid. MS ISP (m/e): 381.3 (100) (M+H)$^+$. $^1$H NMR (DMSO-D$_6$, 250 MHz): δ (ppm)=10.77 (s, 1H), 9.29 (s, 1H), 8.12 (t, 1H), 8.02 (s, 1H), 7.69 (s, 1H), 7.53 (d, 1H), 7.38-7.29 (m, 5H), 3.92 (s, 3H), 2.35 (s, 3H).

EXAMPLE 13

[[4-(2,4-Dichloro-phenyl)-thiazol-2-yl]-[3-methoxy-4-(4-methyl-imidazol-1-yl)-phenyl]-amine The title compound was prepared in analogy to example 1 step e) from 90 mg (0.33 mmol) 2-bromo-2',4'-dichloroacetophenon and 79 mg (0.3 mmol) [3-methoxy-4-(4-methyl-imidazol-1-yl)-phenyl]-thiourea. The crude reaction was diluted with diethyl ether and the precipitate was filtered off and dried to yield 128 mg (99%) [4-(2,4-dichloro-phenyl)-thiazol-2-yl]-[3-methoxy-4-(4-methyl-imidazol-1-yl)-phenyl]-amine as a light yellow solid. MS ISP (m/e): 431.1/433.2 (100/65) (M+H)$^+$. $^1$H NMR (DMSO-D$_6$, 250 MHz): δ (ppm)= 10.78 (s, 1H), 9.28 (s, 1H), 7.99 (s, 1H), 7.97 (d, 1H), 7.74 (s, 1H), 7.67 (s, 1H), 7.55 (d, 1H), 7.53 (s, 1H), 7.50 (d, 1H), 7.25 (d, 1H), 3.88 (s, 3H), 2.34 (s, 3H).

EXAMPLE 14

[4-(2,5-Dichloro-phenyl)-thiazol-2-yl]-[3-methoxy-4-(4-methyl-imidazol-1-yl)-phenyl]-amine The title compound was prepared in analogy to example 1 step e) from 89 mg (0.33 mmol) 2-bromo-1-(2,5-dichlorophenyl)ethanone and 79 mg (0.3 mmol) [3-methoxy-4-(4-methyl-imidazol-1-yl)-phenyl]-thiourea. The crude product was stirred with diethyl ether and little ethanol to yield 130 mg (100%) [4-(2,5-dichloro-phenyl)-thiazol-2-yl]-[3-methoxy-4-(4-methyl-imidazol-1-yl)-phenyl]-amine as a yellow solid. MS ISP (m/e): 431.2/433.0 (100/66) (M+H)$^+$. $^1$H NMR (DMSO-D$_6$, 250 MHz): δ (ppm)=10.80 (s, 1H), 9.29 (s, 1H), 8.15 (s, 1H), 8.08 (s, 1H), 7.69 (s, 1H), 7.67 (s, 1H), 7.61 (d, 1H), 7.51 (d, 1H), 7.45 (d, 1H), 7.15 (d, 1H), 3.93 (s, 3H), 2.34 (s, 3H).

EXAMPLE 15

[4-(2,5-Dimethoxy-phenyl)-thiazol-2-yl]-[3-methoxy-4-(4-methyl-imidazol-1-yl)-phenyl]-amine The title compound was prepared in analogy to example 1 step e) from 88 mg (0.33 mmol) 2-bromo-2',5'-dimethoxyacetophenon and 79 mg (0.3 mmol) [3-methoxy-4-(4-methyl-imidazol-1-yl)-phenyl]-thiourea. The crude reaction was diluted with diethyl ether and stirred for 15 minutes at room temperature. The product was filtered off and dried to yield 124 mg (98%) [4-(2,5-dimethoxy-phenyl)-thiazol-2-yl]-[3-methoxy-4-(4-methyl-imidazol-1-yl)-phenyl]-amine as a light green solid. MS ISP (m/e): 423.2 (100) (M+H)$^+$. $^1$H NMR (DMSO-D$_6$, 250 MHz): δ (ppm)=10.68 (s, 1H), 9.28 (s, 1H), 7.99 (s, 1H), 7.72 (s, 1H), 7.69 (d, 1H), 7.54 (s, 1H), 7.52 (d, 1H), 7.28 (d, 1H), 7.07 (d, 1H), 6.89 (dd, 1H), 3.92 (s, 3H), 3.88 (s, 3H), 3.75 (s, 3H), 2.34 (s, 3H).

EXAMPLE 16

[4-(5-Bromo-2-methoxy-phenyl)-thiazol-2-yl]-[3-methoxy-4-(4-methyl-imidazol-1-yl)-phenyl]-amine The title compound was prepared in analogy to example 1 step e) from 102 mg (0.33 mmol) 2-bromo-1-(5-bromo-2-methoxyphenyl)ethanone and 79 mg (0.3 mmol) [3-methoxy-4-(4-methyl-imidazol-1-yl)-phenyl]-thiourea. The crude reaction was diluted with diethyl ether and stirred for 15 minutes at room temperature. The product was filtered off and dried to yield 147 mg (99%) [4-(5-bromo-2-methoxy-phenyl)-thiazol-2-yl]-[3-methoxy-4-(4-methyl-imidazol-1-yl)-phenyl]-amine as a white solid. MS ISP (m/e): 472.8/470.9 (100/93) (M+H)$^+$. $^1$H NMR (DMSO-D$_6$, 250 MHz): δ (ppm)= 10.74 (s, 1H), 9.30 (s, 1H), 8.34 (dd, 1H), 7.70 (s, 1H), 7.60 (s, 1H), 7.51 (d, 1H), 7.47 (d, 1H), 7.13 (d, 1H), 7.05 (d, 1H), 4.00 (s, 3H), 3.95 (s, 3H), 2.35 (s, 3H).

EXAMPLE 17

[3-Methoxy-4-(4-methyl-imidazol-1-yl)-phenyl]-[4-(3-methoxy-phenyl)-thiazol-2-yl]-amine The title compound was prepared in analogy to example 1 step e) from 77 mg (0.33 mmol) 2-bromo-3'-methoxyacetophenon and 79 mg (0.3 mmol) [3-methoxy-4-(4-methyl-imidazol-1-yl)-phenyl]-thiourea. The solvent was evaporated under reduced pressure and the crude reaction was stirred with diethyl ether and little ethanol for 15 minutes at room temperature. The product was filtered off and dried to yield 118 mg (100%) [3-methoxy-4-(4-methyl-imidazol-1-yl)-phenyl]-[4-(3-methoxy-phenyl)-thiazol-2-yl]-amine as a light green solid. MS ISP (m/e): 393.2 (100) (M+H)$^+$. $^1$H NMR (DMSO-D$_6$, 250 MHz): δ (ppm)=10.72 (s, 1H), 9.31 (s, 1H), 8.06 (s, 1H), 7.69 (s, 1H), 7.54-7.51 (m, 4H), 7.35 (t, 1H), 7.28 (d, 1H), 6.90 (d, 1H), 3.93 (s, 3H), 3.81 (s, 3H), 2.35 (s, 3H).

EXAMPLE 18

[3-Methoxy-4-(4-methyl-imidazol-1-yl)-phenyl]-[4-(4-methoxy-phenyl)-thiazol-2-yl]-amine The title compound was prepared in analogy to example 1 step e) from 78 mg (0.33 mmol) 4-methoxyphenaxylbromide and 79 mg (0.3 mmol) [3-methoxy-4-(4-methyl-imidazol-1-yl)-phenyl]-thiourea. The solvent was evaporated under reduced pressure and the crude reaction was stirred with methylene chloride/diethyl ether for 15 minutes at room temperature. The product was filtered off and dried to yield 118 mg (100%) [3-methoxy-4-(4-methyl-imidazol-1-yl)-phenyl]-[4-(4-methoxy-phenyl)-thiazol-2-yl]-amine as a light green solid. MS ISP (m/e): 393.2 (100) (M+H)$^+$. $^1$H NMR (DMSO-D$_6$, 250 MHz): δ (ppm)=10.69 (s, 1H), 9.31 (s, 1H), 8.05 (s, 1H), 7.89 (d, 2H), 7.69 (s, 1H), 7.51 (d, 1H), 7.30 (s, 1H), 7.28 (d, 1H), 7.00 (d, 2H), 3.93 (s, 3H), 3.80 (s, 3H), 2.35 (s, 3H).

EXAMPLE 19

[4-(3-Chloro-phenyl)-thiazol-2-yl]-[3-methoxy-4-(4-methyl-imidazol-1-yl)-phenyl]-amine The title compound was prepared in analogy to example 1 step e) from 77 mg (0.33 mmol) 3-chlorophenacylbromide and 79 mg (0.3 mmol) [3-methoxy-4-(4-methyl-imidazol-1-yl)-phenyl]-thiourea. The solvent was evaporated under reduced pressure and the crude reaction was stirred with methylene chloride/diethyl ether/ethanol for 15 minutes at room temperature. The product was filtered off and dried to yield 118 mg (100%) [4-(3-chloro-phenyl)-thiazol-2-yl]-[3-methoxy-4-(4-methyl-imidazol-1-yl)-phenyl]-amine as a light yellow solid. MS ISP (m/e): 397.1/399.2 (100/46) (M+H)$^+$. $^1$H NMR (DMSO-D$_6$, 250 MHz): δ (ppm)=10.78 (s, 1H), 9.29 (s, 1H), 8.10 (s, 1H), 8.01 (s, 1H), 7.90 (d, 1H), 7.69 (s, 1H), 7.64 (s, 1H), 7.52 (d, 1H), 7.48 (t, 1H), 7.38 (d, 1H), 7.24 (d, 1H), 3.95 (s, 3H), 2.35 (s, 3H).

EXAMPLE 20

[4-(2-Chloro-phenyl)-thiazol-2-yl]-[3-methoxy-4-(4-methyl-imidazol-1-yl)-phenyl]-amine The title compound was prepared in analogy to example 1 step e) from 77 mg (0.33 mmol) 2-chlorophenacylbromide and 79 mg (0.3 mmol) [3-methoxy-4-(4-methyl-imidazol-1-yl)-phenyl]-thiourea. The solvent was evaporated under reduced pressure and the crude reaction was stirred with methylene chloride/diethyl ether/ethanol for 15 minutes at room temperature. The product was filtered off and dried to yield 118 mg (100%) [4-(2-chloro-phenyl)-thiazol-2-yl]-[3-methoxy-4-(4-methyl-imidazol-1-yl)-phenyl]-amine as a light yellow solid. MS ISP (m/e): 397.1/399.2 (100/44) (M+H)$^+$. $^1$H NMR (DMSO-D$_6$, 250 MHz): δ (ppm)=10.71 (s, 1H), 9.27 (s, 1H), 7.98 (s, 1H), 7.93 (d, 1H), 7.67 (s, 1H), 7.56 (d, 1H), 7.51-7.38 (m, 4H), 7.27 (d, 1H), 3.88 (s, 3H), 2.34 (s, 3H).

EXAMPLE 21

[4-(5-Bromo-2-methoxy-phenyl)-thiazol-2-yl]-[4-(4-methyl-imidazol-1-yl)-phenyl]-amine a) [4-(4-Methyl-imidazol-1-yl)-phenyl]-thiourea
The title compound was prepared in analogy to example 4 step c) from 1000 mg (5.8 mmol) 4-(4-methyl-imidazol-1-yl)-phenylamine and 989 mg (6.1 mmol) benzoylisocyanate to yield 1270 mg (95%) [4-(4-methyl-imidazol-1-yl)-phenyl]-thiourea as a light brown solid. MS ISP (m/e): 216.1 (100) (M-NH$_3$+H)$^+$, 232.7 (70) (M+H)$^+$.
b) [4-(5-Bromo-2-methoxy-phenyl)-thiazol-2-yl]-[4-(4-methyl-imidazol-1-yl)-phenyl]-amine
The title compound was prepared in analogy to example 1 step e) from 219 mg (0.71 mmol) 2-bromo-1-(5-bromo-2-methoxyphenyl)acetone and 150 mg (0.65 mmol) [4-(4-methyl-imidazol-1-yl)-phenyl]-thiourea to yield 196 mg (69%) [4-(5-bromo-2-methoxy-phenyl)-thiazol-2-yl]-[4-(4-methyl-imidazol-1-yl)-phenyl]-amine as a white solid. MS ISP (m/e): 441.2.1/443.2.2 (95/100) (M+H)$^+$.

EXAMPLE 22

[4-(5-Bromo-2-methoxy-phenyl)-thiazol-2-yl]-(4-imidazol-1-yl-3-methoxy-phenyl)-amine a) 1-(2-Methoxy-4-nitro-phenyl)-1H-imidazole The title compound was prepared in analogy to example 4 step a) from 1000 mg (5.3 mmol) 2-chloro-5-nitroanisole and 1751 mg (21.3 mmol) imidazol. The crude product was purified on silica gel with methylene chloride/methanol 95/5 yielding 430 mg (35%) 1-(2-methoxy-4-nitro-phenyl)-1H-imidazole as a brown solid. MS ISP (m/e): 220.1 (100) $(M+H)^+$.

b) 3-Methoxy-4-(imidazol-1-yl)-phenylamine

A solution of 350 mg (1.6 mmol) 1-(2-methoxy-4-nitro-phenyl)-1H-imidazole and 1873 mg (8.3 mmol) stannous dichloride in ethyl acetate (5 ml) and ethanol (2.5 ml) were heated to 70° for 35 minutes. The reaction was poured onto water/ice and neutralized with an aqueous solution of sodium hydrogen carbonate. It was extracted three times with ethyl acetate. The combined organic layers were washed with brine, dried over magnesium sulphate, filtered and the solvent was evaporated under reduced pressure to yield 255 mg (84%) 3-methoxy-4-(imidazol-1-yl)-phenylamine as a brown solid. MS ISP (m/e): 190.0 (100) $(M+H)^+$.

c) (4-Imidazol-1-yl-3-methoxy-phenyl)-thiourea

The title compound was prepared in analogy to example 4 step c) from 250 mg (1.32 mmol) 3-methoxy-4-(imidazol-1-yl)-phenylamine and 226 mg (1.39 mmol) benzoylisocyanate yielding 180 mg (55%) (4-imidazol-1-yl-3-methoxy-phenyl)-thiourea as a light brown solid. MS ISP (m/e): 231.8 (90) $(M-NH_3+H)^+$, 248.8 (100) $(M+H)^+$.

d) [4-(5-Bromo-2-methoxy-phenyl)-thiazol-2-yl]-(4-imidazol-1-yl-3-methoxy-phenyl)-amine The title compound was prepared in analogy to example 1 step e) from 232 mg (0.75 mmol) 2-bromo-1-(5-bromo-2-methoxyphenyl)ethanone and 170 mg (0.68 mmol) (4-imidazol-1-yl-3-methoxy-phenyl)-thiourea yielding 130 mg (41%) [4-(5-bromo-2-methoxy-phenyl)-thiazol-2-yl]-(4-imidazol-1-yl-3-methoxy-phenyl)-amine as a light yellow solid. MS ISP (m/e): 457.1/459.3 (100/90) $(M+H)^+$.

EXAMPLE 23

2-[3-Methoxy-4-(4-methyl-imidazol-1-yl)-phenylamino]-4-methyl-thiazole-5-carboxylic acid ethyl ester A solution of 46 mg (0.25 mmol) ethyl 2-chloroacetoacetate and of 36 mg (0.375 mmol) potassium rhodanide in ethanol (0.75 ml) was stirred at room temperature for 1 hour. 51 mg (0.25 mmol) 3-methoxy-4-(4-methyl-imidazol-1-yl)-phenylamine was added and the reaction was heated to reflux for 3 hours. A solid precipitated. The reaction was diluted with water and extracted twice with ethyl acetate. The insoluble precipitate was filtered off, washed with ethyl acetate and dried to yield the 16.5 mg of the title compound. The organic layer was dried over sodium sulphate, filtered and the solvent was evaporated in vacuo. The residue was purified on silica gel with methylene chloride/methanol 19/1. The fraction with the product was stirred with diethyl ether at room temperature and the solid was filtered off. The product was combined yielding 32 mg (35%) 2-[3-methoxy-4-(4-methyl-imidazol-1-yl)-phenylamino]-4-methyl-thiazole-5-carboxylic acid ethyl ester as a yellow solid. MS ISP (m/e): 373.2 (100) $(M+H)^+$. $^1$H NMR (DMSO-D$_6$, 250 MHz): δ (ppm)=10.93 (s, 1H), 8.49 (s, 1H), 7.61 (s, 1H), 7.43 (d, 1H), 7.37 (s, 1H), 7.31 (s, 1H), 4.22 (q, 2H), 3.84 (s, 3H), 2.55 (s, 3H), 2.24 (s, 3H), 1.27 (t, 3H).

EXAMPLE 24

[3-Methoxy-4-(4-methyl-imidazol-1-yl)-phenyl]-(4,5,6,7-tetrahydro-benzothiazol-2-yl)-amine The title compound was prepared in analogy to example 1 step e) from 46 mg (0.33 mmol) 2-chlorocyclohexanon and 79 mg (0.3 mmol) [3-methoxy-4-(4-methyl-imidazol-1-yl)-phenyl]-thiourea in ethanol (3 ml). The crude product was purified on silica gel with methylene chloride/methanol 19/1 yielding 40 mg (39%) [3-methoxy-4-(4-methyl-imidazol-1-yl)-phenyl]-(4,5,6,7-tetrahydro-benzothiazol-2-yl)-amine as a yellow solid. MS ISP (m/e): 341.4 (100) $(M+H)^+$. $^1$H NMR (DMSO-D$_6$, 250 MHz): δ (ppm)=10.16 (s, 1H), 7.63 (s, 1H), 7.49 (s, 1H), 7.28 (d, 1H), 7.22 (d, 1H), 7.01 (s, 1H), 3.77 (s, 3H), 2.57 (br s, 4H), 2.14 (s, 3H), 1.71 (br s, 4H).

EXAMPLE 25

(5,6-Dihydro-4H-cyclopentathiazol-2-yl)-[3-methoxy-4-(4-methyl-imidazol-1-yl)-phenyl]-amine The title compound was prepared in analogy to example 1 step e) from 40 mg (0.33 mmol) 2-chlorocyclopentanone and 79 mg (0.3 mmol) [3-methoxy-4-(4-methyl-imidazol-1-yl)-phenyl]-thiourea in ethanol (1.5 ml) and dioxane (1.5 ml). The crude product was purified on silica gel with methylene chloride/methanol 19/1 yielding 41 mg (42%) (5,6-dihydro-4H-cyclopentathiazol-2-yl)-[3-methoxy-4-(4-methyl-imidazol-1-yl)-phenyl]-amine as a light yellow solid. MS ISP (m/e): 327.3 (100) $(M+H)^+$. $^1$H NMR (DMSO-D$_6$, 250 MHz): δ (ppm)=10.25 (s, 1H), 7.64 (s, 1H), 7.44 (s, 1H), 7.32 (d, 1H), 7.23 (d, 1H), 7.01 (s, 1H), 3.78 (s, 3H), 2.78 (br t, 2H), 2.67 (br t, 2H), 2.35 (m, 2H), 2.14 (s, 3H).

EXAMPLE 26

{2-[3-Methoxy-4-(4-methyl-imidazol-1-yl)-phenylamino]-thiazol-4-yl}-acetic acid ethyl ester The title compound was prepared in analogy to example 1 step e) from 56 mg (0.33 mmol) ethyl 4-chloroacetoacetate and 79 mg (0.3 mmol) [3-methoxy-4-(4-methyl-imidazol-1-yl)-phenyl]-thiourea. The crude product was purified through stirring with diethyl ether yielding 115 mg (98%) {2-[3-methoxy-4-(4-methyl-imidazol-1-yl)-phenylamino]-thiazol-4-yl}-acetic acid ethyl ester as an off-white solid. MS ISP (m/e): 373.1 (100) $(M+H)^+$. $^1$H NMR (DMSO-D$_6$, 250 MHz): δ (ppm)=10.68 (s, 1H), 9.26 (s, 1H), 7.83 (s, 1H), 7.65 (s, 1H), 7.46 (d, 1H), 7.22 n(d, 1H), 6.79 (s, 1H), 4.09 (q, 2H), 3.83 (s, 3H), 3.67 (s, 2H), 2.33 (s, 3H), 1.19 (t, 3H).

EXAMPLE 27

2-{2-[3-Methoxy-4-(4-methyl-imidazol-1-yl)-phenylamino]-thiazol-4-yl}-1-piperidin-1-yl-ethanone To a solution of 80 mg (0.94 mmol) piperidine in dioxane (1 ml) 2M trimethylaluminium solution in heptane (0.94 mmol, 0.47 ml) was carefully added. The solution was stirred at room temperature for 1 hour. A suspension of 100 mg (0.27 mmol) ({2-[3-methoxy-4-(4-methyl-imidazol-1-yl)-phenylamino]-thiazol-4-yl}-acetic acid ethyl ester in dioxane (3 ml) was added and the reaction was refluxed over night. Water was added carefully and the reaction was extracted twice with ethyl acetate. The organic layer was dried over sodium sulphate, filtered and the solvent was evaporated under reduced pressure to yield 110 mg (99%) 2-{2-[3-methoxy-4-(4-methyl-imidazol-1-yl)-phenylamino]-thiazol-4-yl}-1-piperidin-1-yl-ethanone as a brown foam. MS ISP (m/e): 410.1 (100) (M+H)$^+$. $^1$H NMR (DMSO-D$_6$, 250 MHz): δ (ppm)= 10.35 (s, 1H), 7.70 (s, 1H), 7.65 (s, 1H), 7.23 (d, 1H), 7.17 (d, 1H), 7.03 (s, 1H), 6.64 (s, 1H), 3.79 (s, 3H), 3.67 (s, 2H), 3.49 (br t, 2H), 3.42 (br t, 2H), 2.14 (s, 3H), 1.58-1.32 (m, 6H).

EXAMPLE 28

N-Butyl-2-{2-[3-methoxy-4-(4-methyl-imidazol-1-yl)-phenylamino]-thiazol-4-yl}-acetamide The title compound was prepared in analogy to example 27 from 100 mg (0.27 mmol) ({2-[3-methoxy-4-(4-methyl-imidazol-1-yl)-phenylamino]-thiazol-4-yl}-acetic acid ethyl ester and 70 mg (0.94 mmol) n-butylamine yielding 95 mg (89%) N-butyl-2-{2-[3-methoxy-4-(4-methyl-imidazol-1-yl)-phenylamino]-thiazol-4-yl}-acetamide as a brown foam. MS ISP (m/e): 400.3 (100) (M+H)$^+$. $^1$H NMR (DMSO-D$_6$, 250 MHz): δ (ppm)=10.45 (s, 1H), 7.93 (t, 1H), 7.68 (s, 1H), 7.64 (s, 1H), 7.23 (d, 1H), 7.19 (d, 1H), 7.02 (s, 1H), 6.62 (s, 1H), 3.79 (s, 3H), 3.57 (s, 2H), 3.05 (br q, 2H), 2.14 (s, 3H), 1.39-1.26 (m, 6H), 0.85 (t, 3H).

EXAMPLE 29

N-(4-Fluoro-phenyl)-2-{2-[3-methoxy-4-(4-methyl-imidazol-1-yl)-phenylamino]-thiazol-4-yl}-acetamide The title compound was prepared in analogy to example 27 from 92 mg (0.25 mmol) ({2-[3-methoxy-4-(4-methyl-imidazol-1-yl)-phenylamino]-thiazol-4-yl}-acetic acid ethyl ester and 98 mg (0.87 mmol) 4-fluoroaniline. After the first addition conversion was not complete. Therefore the same amount of the aniline and trimethylaluminium were added and the reaction was heated again over night. Workup as in example 27 and subsequent purification on silica gel with methylene chloride/methanol 19/1 yielded 95 mg (89%) N-(4-fluoro-phenyl)-2-{2-[3-methoxy-4-(4-methyl-imidazol-1-yl)-phenylamino]-thiazol-4-yl}-acetamide as a brown oil. MS ISP (m/e): 438.1 (100) (M+H)$^+$. $^1$H NMR (CDCl$_3$, 250 MHz): δ (ppm)=9.08 (s, 1H), 7.65 (s, 2H), 7.45 (dd, 2H), 7.31 (s, 1H), 7.21 (d, 1H), 7.06-6.88 (m, 3H), 6.51 (s, 1H), 3.80 (s, 3H), 3.73 (s, 2H), 2.30 (s, 3H).

EXAMPLE 30

((S)-1-{2-[3-Methoxy-4-(4-methyl-imidazol-1-yl)-phenylamino]-thiazol-4-yl}-3-methyl-butyl)-carbamic acid tert-butyl ester The title compound was prepared in analogy to example 1 step e) from 102 mg (0.33 mmol) (S)-[1-(2-bromo-acetyl)-3-methyl-butyl]-carbamic acid tert-butyl ester, 42 mg (0.33 mmol) N,N-diisopropyl ethyl amine and 79 mg (0.3 mmol) [3-methoxy-4-(4-methyl-imidazol-1-yl)-phenyl]-thiourea. The crude reaction was poured onto water and extracted twice with ethyl acetate. The organic layer was washed with brine, dried over sodium sulphate, filtered and the solvent was evaporated under vacuo. The crude product was purified on silica gel with methylene chloride/methanol 19/1 yielding 97 mg (69%) ((S)-1-{2-[3-methoxy-4-(4-methyl-imidazol-1-yl)-phenylamino]-thiazol-4-yl}-3-methyl-butyl)-carbamic acid tert-butyl ester as a light yellow solid. MS ISP (m/e): 472.3 (100) (M+H)$^+$. $^1$H NMR (DMSO-D$_6$, 250 MHz): δ (ppm)=10.35 (s, 1H), 7.95 (s, 1H), 7.65 (s, 1H), 7.23 (d, 1H), 7.15 (d, 1H), 7.03 (s, 1H), 6.99 (d, 1H), 6.55 (s, 1H), 4.59 (m, 1H), 3.82 (s, 3H), 2.14 (s, 3H), 1.70-1.55 (m, 3H), 1.39 (s, 9H), 0.90 (s, 6H). α$_{589}$=−43.2; T=20° C.; c=1 g/m100 ml, solvent=MeOH.

EXAMPLE 31

[4-((S)-1-Amino-3-methyl-butyl)-thiazol-2-yl]-[3-methoxy-4-(4-methyl-imidazol-1-yl)-phenyl]-amine trihydrochloride 1162 mg (2.46 mmol) ((S)—1-{2-[3-Methoxy-4-(4-methyl-imidazol-1-yl)-phenylamino]-thiazol-4-yl}-3-methyl-butyl)-carbamic acid tert-butyl ester was dissolved in methylene chloride (24.6 ml) and 2M HCl in diethyl ether (12.3 ml) was added at room temperature. A solid precipitated. The reaction was stirred at room temperature over night. The reaction was diluted with diethyl ether, stirred for 15 minutes and the solid was filtered off, washed with diethyl ether and dried to yield 1195 mg (100%) [4-((S)-1-amino-3-methyl-butyl)-thiazol-2-yl]-[3-methoxy-4-(4-methyl-imidazol-1-yl)-phenyl]-amine trihydrochloride as a light yellow solid. MS ISP (m/e): 372.2 (100) (M+H)$^+$. $^1$H NMR (DMSO-D$_6$, 250 MHz): δ (ppm)=10.98 (s, 1H), 9.31 (s, 1H), 8.46 (br s, 3H), 7.93 (s, 1H), 7.66 (s, 1H), 7.47 (d, 1H), 7.31 (d, 1H), 7.13 (s, 1H), 4.27 (m, 1H), 3.90 (s, 3H), 2.35 (s, 3H), 1.94-1.83 (m, 1H), 1.80-1.69 (m, 1H), 1.52-1.39 (m, 1H), 0.90 (d, 3H), 0.86 (d, 3H).

EXAMPLE 32

{4-[(S)-1-(4-Fluoro-benzylamino)-3-methyl-butyl]-thiazol-2-yl}-[3-methoxy-4-(4-methyl-imidazol-1-yl)-phenyl]-amine 96 mg (0.2 mmol) [4-((S)-1-Amino-3-methyl-butyl)-thiazol-2-yl]-[3-methoxy-4-(4-methyl-imidazol-1-yl)-phenyl]-amine trihydrochloride was suspended in tetrahydrofurane (3 ml). At room temperature under nitrogen 103 mg (0.8 mmol) N,N-diisopropyl ethyl amine was added and the reaction was stirred for 10 minutes. 28 mg (0.22 mmol) 4-fluorobenzaldehyde, 24 mg (0.4 mmol) acetic acid and 127 mg (0.6 mmol) sodium triacetoxyborohydride were added and the reaction was stirred at room temperature over night. 2N aqueous NaOH solution (6 ml) was added and the reaction was extracted twice with diethyl ether. The combined organic layers were washed with brine, dried over sodium sulphate, filtered and the solvent was evaporated under reduced pressure. The crude product was purified on silica gel with methylene chloride/methanol 19/1 yielding 48 mg (50%) of {4-[(S)-1-(4-fluoro-benzylamino)-3-methyl-butyl]-thiazol-2-yl}-[3-methoxy-4-(4-methyl-imidazol-1-yl)-phenyl]-amine as a yellow solid. MS ISP (m/e): 480.1 (100) (M+H)$^+$. $^1$H NMR (DMSO-D$_6$, 250 MHz): δ (ppm)=10.37 (s, 1H), 7.89 (s, 1H), 7.65 (s, 1H), 7.34-7.31 (m, 3H), 7.24 (d, 1H), 7.13-7.02 (m, 4H), 6.67 (s, 1H), 3.77 (m, 4H), 3.69 (d, 1H), 3.53-3.49 (m, 3H), 2.14 (s, 3H), 1.59-1.51 (m, 3H), 0.85 (d, 3H), 0.78 (d, 3H).

EXAMPLE 33

[3-Methoxy-4-(4-methyl-imidazol-1-yl)-phenyl]-[4-((S)-3-methyl-1-phenethylamino-butyl)-thiazol-2-yl]-amine The title compound was prepared in analogy to example 32 from 96 mg (0.2 mmol) [4-((S)-1-amino-3-methyl-butyl)- thiazol-2-yl]-[3-methoxy-4-(4-methyl-imidazol-1-yl)-phenyl]-amine trihydrochloride and 27 mg (0.22 mmol) phenylacetaldehyde yielding 44 mg (46%) [3-methoxy-4-(4-methyl-imidazol-1-yl)-phenyl]-[4-((S)-3-methyl-1-phenethylamino-butyl)-thiazol-2-yl]-amine as a yellow solid. MS ISP (m/e): 476.1 (100) (M+H)$^+$. $^1$H NMR (DMSO-D$_6$, 250 MHz): δ (ppm)=10.34 (s, 1H), 7.87 (s, 1H), 7.65 (s, 1H), 7.24-7.13 (m, 6H), 7.02 (s, 1H), 7.00 (d, 1H), 6.64 (s, 1H), 3.76 (s, 3H), 3.59 (br t, 1H), 2.72-2.59 (m, 4H), 2.14 (s, 3H), 1.59-1.48 (m, 3H), 0.87 (d, 3H), 0.82 (d, 3H).

EXAMPLE 34

2-(4-Fluoro-phenyl)-N—((S)-1-{2-[3-methoxy-4-(4-methyl-imidazol-1-yl)-phenylamino]-thiazol-4-yl}-3-methyl-butyl)-acetamide To a solution of 96 mg (0.2 mmol) [4-((S)-1-amino-3-methyl-butyl)-thiazol-2-yl]-[3-methoxy-4-(4-methyl-imidazol-1-yl)-phenyl]-amine trihydrochloride and of 35 mg (0.22 mmol) 4-fluorophenylacetic acid in DMF (2 ml) 121 mg (1.2 mmol) N-methyl morpholine and 114 mg (0.3 mmol) HBTU (O-(1H-benzotriazol-1-yl)-N,N,N',N'-tetramethyluronium hexafluorophosphate) were added. The reaction was stirred over night at room temperature. The reaction was diluted with 2N aqueous NaOH solution (6 ml) and extracted twice with ethyl acetate. The combined organic layers were dried over sodium sulphate, filtered and the solvent was evaporated under reduced pressure. The crude product was purified on silica gel with methylene chloride/methanol 19/1 yielding 95 mg (94%) of 2-(4-fluoro-phenyl)-N—((S)-1-{2-[3-methoxy-4-(4-methyl-imidazol-1-yl)-phenylamino]-thiazol-4-yl}-3-methyl-butyl)-acetamide as a yellow solid. MS ISP (m/e): 508.0 (100) (M+H)$^+$. $^1$H NMR (DMSO-D$_6$, 250 MHz): δ (ppm) 10.38 (s, 1H), 8.30 (d, 1H), 7.96 (d, 1H), 7.89 (s, 1H), 7.65 (s, 1H), 7.30-7.20 (m, 3H), 7.15-6.97 (m, 4H), 6.54 (s, 1H), 4.60 (m, 1H), 3.80 (s, 3H), 3.45 (m, 2H), 2.14 (s, 3H), 1.69-1.48 (m, 3H), 0.92 (d, 3H), 0.85 (d, 3H).

EXAMPLE 35

2-Methoxy-N—((S)-1-{2-[3-methoxy-4-(4-methyl-imidazol-1-yl)-phenylamino]-thiazol-4-yl}-3-methyl-butyl)-acetamide The title compound was prepared in analogy to example 34 from 96 mg (0.2 mmol) [4-((S)-1-amino-3-methyl-butyl)-thiazol-2-yl]-[3-methoxy-4-(4-methyl-imidazol-1-yl)-phenyl]-amine trihydrochloride and 20 mg (0.22 mmol) methoxyacetic acid yielding 100 mg (100%) 2-methoxy-N—((S)-1-{2-[3-methoxy-4-(4-methyl-imidazol-1-yl)-phenylamino]-thiazol-4-yl}-3-methyl-butyl)-acetamide as a viscous oil. MS ISP (m/e): 444.2 (100) (M+H)$^+$. $^1$H NMR (DMSO-D$_6$, 250 MHz): δ (ppm)=10.38 (s, 1H), 7.82 (d, 1H), 7.64 (s, 1H), 7.23 (d, 1H), 7.02 (s, 1H), 6.98 (d, 1H), 6.62 (s, 1H), 4.98 (q, 1H), 3.85 (s, 2H), 3.82 (s, 3H), 2.73 (s, 3H), 2.14 (s, 3H), 1.71 (t, 2H), 1.55 (m, 1H), 0.90 (t, 6H).

EXAMPLE 36

N—((S)-1-{2-[3-Methoxy-4-(4-methyl-imidazol-1-yl)-phenylamino]-thiazol-4-yl}-3-methyl-butyl)-2,2-dimethyl-propionamide 96 mg (0.2 mmol) [4-((S)-1-amino-3-methyl-butyl)-thiazol-2-yl]-[3-methoxy-4-(4-methyl-imidazol-1-yl)-phenyl]-amine trihydrochloride and 25 mg (0.2 mmol) pivaloylchloride were suspended in methylene chloride (2 ml) and 101 mg (1 mmol) triethyl amine was added at room temperature. The reaction was stirred over night, diluted with methylene chloride, washed once with water, once with brine, dried over sodium sulphate, filtered and the solvent was evaporated under reduced pressure to yield 90 mg (99%) N—((S)-1-{2-[3-methoxy-4-(4-methyl-imidazol-1-yl)-phenylamino]-thiazol-4-yl}-3-methyl-butyl)-2,2-dimethyl-propionamide as a light yellow solid. MS ISP (m/e): 456.3 (100) (M+H)$^+$. $^1$H NMR (DMSO-D$_6$, 250 MHz): δ (ppm)=10.37 (s, 1H), 7.88 (s, 1H), 7.65 (s, 1H), 7.55 (d, 1H), 7.22 (d, 1H), 7.05-6.99 (m, 2H), 6.44 (s, 1H), 4.95 (m, 1H), 3.82 (s, 3H), 2.14 (s, 3H), 1.73 (m, 2H), 1.65 (m, 1H), 1.14 (s, 9H), 0.91 (d, 3H), 0.87 (d, 3H).

EXAMPLE 37

4-Fluoro-N—((S)-1-{2-[3-methoxy-4-(4-methyl-imidazol-1-yl)-phenylamino]-thiazol-4-yl}-3-methyl-butyl)-benzamide The title compound was prepared in analogy to example 36 from 96 mg (0.2 mmol) [4-((S)-1-amino-3-methyl-butyl)-thiazol-2-yl]-[3-methoxy-4-(4-methyl-imidazol-1-yl)-phenyl]-amine trihydrochloride and 33 mg (0.2 mmol) 4-fluororobenzoylchloride. The crude product was purified on silica gel with methylene chloride/methanol 19/1 yielding 81 mg (82%) 4-fluoro-N-((S)-1-{2-[3-methoxy-4-(4-methyl-imidazol-1-yl)-phenylamino]-thiazol-4-yl}-3-methyl-butyl)-benzamide as a yellow solid. MS ISP (m/e): 494.0 (100) (M+H)$^+$. $^1$H NMR (DMSO-D$_6$, 250 MHz): δ (ppm)=10.38 (s, 1H), 8.65 (d, 1H), 8.02-7.88 (m, 3H), 7.65 (s, 1H), 7.30 (t, 2H), 7.23 (d, 1H), 7.02 (s, 1H), 6.99 (d, 1H), 6.64 (s, 1H), 5.17 (q, 1H), 3.77 (s, 3H), 2.14 (s, 3H), 1.83 (m, 2H), 1.68 (m, 1H), 0.94 (d, 3H), 0.92 (d, 3H).

EXAMPLE 38

3,3,3-Trifluoro-N—((S)-1-{2-[3-methoxy-4-(4-methyl-imidazol-1-yl)-phenylamino]-thiazol-4-yl}-3-methyl-butyl)-propionamide The title compound was prepared in analogy to example 36 from 96 mg (0.2 mmol) [4-((S)-1-amino-3-methyl-butyl)-thiazol-2-yl]-[3-methoxy-4-(4-methyl-imidazol-1-yl)-phenyl]-amine trihydrochloride and 30 mg (0.2 mmol) 3,3,3-trifluoropropionylchloride. The crude product was purified on silica gel with methylene chloride/methanol 19/1 yielding 32 mg (33%) 3,3,3-trifluoro-N—((S)-1-{2-[3-methoxy-4-(4-methyl-imidazol-1-yl)-phenylamino]-thiazol-4-yl}-3-methyl-butyl)-propionamide as a yellow solid. MS ISP (m/e): 482.1 (100) (M+H)$^+$. $^1$H NMR (DMSO-D$_6$, 250 MHz): δ (ppm)=10.39 (s, 1H), 8.50 (d, 1H), 7.91 (s, 1H), 7.66 (s, 1H), 7.24 (d, 1H), 7.03 (s, 1H), 7.01 (d, 1H), 6.64 (s, 1H), 4.92 (q, 1H), 3.82 (s, 3H), 2.14 (s, 3H), 1.75 (m, 1H), 1.62 (m, 2H), 0.91 (d, 3H), 0.88 (d, 3H).

EXAMPLE 39

4-Fluoro-N—((S)-1-{2-[3-methoxy-4-(4-methyl-imidazol-1-yl)-phenylamino]-thiazol-4-yl}-3-methyl-butyl)-benzene sulfonamide The title compound was prepared in analogy to example 36 from 96 mg (0.2 mmol) [4-((S)-1-amino-3-methyl-butyl)-thiazol-2-yl]-[3-methoxy-4-(4-methyl-imidazol-1-yl)-phenyl]-amine trihydrochloride and 40 mg (0.2 mmol) 4-fluororobenzenesulfonylchloride. The crude product was purified on silica gel with methylene chloride/methanol 19/1 yielding 85 mg (80%) 4-fluoro-N—((S)-1-{2-[3-methoxy-4-(4-methyl-imidazol-1-yl)-phenylamino]-thiazol-4-yl}-3-methyl-butyl)-benzenesulfonamide as a light yellow solid. MS ISP (m/e): 530.0 (100) (M+H)$^+$. $^1$H NMR (DMSO-D$_6$, 250 MHz): δ (ppm)=10.24 (s, 1H), 8.16 (d, 1H), 7.78-7.65 (m, 3H), 7.23-7.17 (m, 3H), 7.03 (s, 1H), 7.02 (d, 1H), 4.23 (q, 1H), 3.83 (s, 3H), 2.15 (s, 3H), 1.59 (m, 2H), 1.49 (m, 1H), 0.82 (d, 3H), 0.76 (d, 3H).

EXAMPLE 40

N—((S)-1-{2-[3-Methoxy-4-(4-methyl-imidazol-1-yl)-phenylamino]-thiazol-4-yl}-3-methyl-butyl)-C-phenyl-methanesulfonamide The title compound was prepared in analogy to example 36 from 96 mg (0.2 mmol) [4-((S)-1-amino-3-methyl-butyl)-thiazol-2-yl]-[3-methoxy-4-(4-methyl-imidazol-1-yl)-phenyl]-amine trihydrochloride and 39 mg (0.2 mmol) alpha-toluenesulphonylchloride. The crude product was purified on silica gel with methylene chloride/methanol 19/1 yielding 40 mg (38%) N—((S)-1-{2-[3-methoxy-4-(4-methyl-imidazol-1-yl)-phenylamino]-thiazol-4-yl}-3-methyl-butyl)-C-phenyl-methanesulfonamide as a light yellow solid. MS ISP (m/e): 525.9 (100) (M+H)$^+$. $^1$H NMR (DMSO-D$_6$, 250 MHz): δ (ppm)=10.48 (s, 1H), 7.97 (s, 1H), 7.65 (s, 1H), 7.60 (d, 1H), 7.26-7.21 (m, 6H), 7.06 (d, 1H), 7.03 (s, 1H), 4.39 (q, 1H), 4.13 (d, 1H), 4.03 (d, 1H), 3.83 (s, 3H), 2.14 (s, 3H), 1.69 (m, 2H), 1.56 (m, 1H), 0.86 (d, 6H).

EXAMPLE 41

N—((S)-1-{2-[3-Methoxy-4-(4-methyl-imidazol-1-yl)-phenylamino]-thiazol-4-yl}-3-methyl-butyl)-methane sulfonamide The title compound was prepared in analogy to example 36 from 96 mg (0.2 mmol) [4-((S)-1-amino-3-methyl-butyl)-thiazol-2-yl]-[3-methoxy-4-(4-methyl-imidazol-1-yl)-phenyl]-amine trihydrochloride and 23 mg (0.2 mmol) methyl sulfonyl chloride. The crude product was purified on silica gel with methylene chloride/methanol 19/1 yielding 45 mg (50%) N—((S)-1-{2-[3-methoxy-4-(4-methyl-imidazol-1-yl)-phenylamino]-thiazol-4-yl}-3-methyl-butyl)-methanesulfonamide as a light yellow solid. MS ISP (m/e): 450.1 (100) (M+H)$^+$. $^1$H NMR (DMSO-D$_6$, 250 MHz): δ (ppm)= 10.40 (s, 1H), 7.90 (s, 1H), 7.65 (s, 1H), 7.54 (d, 1H), 7.24 (d, 1H), 7.06 (d, 1H), 7.03 (s, 1H), 6.81 (s, 1H), 4.36 (q, 1H), 3.84 (s, 3H), 2.14 (s, 3H), 1.65 (m, 3H), 0.89 (m, 6H).

EXAMPLE 42

2-[3-Methoxy-4-(4-methyl-imidazol-1-yl)-phenylamino]-4-trifluoromethyl-thiazole-5-carboxylic acid ethyl ester The title compound was prepared in analogy to example 1 step e) from 76 mg (0.33 mmol) ethyl 2-chloro-3-keto-4,4,4-trifluorobutyrate and 79 mg (0.3 mmol) [3-methoxy-4-(4-methyl-imidazol-1-yl)-phenyl]-thiourea. The reaction was refluxed for 5 days. The crude product was purified on silica gel with methylene chloride/methanol 9/1. The crude product was stirred with methylene chloride/diethyl ether. The precipitate was filtered off and dried to yield 31 mg (24%) of 2-[3-methoxy-4-(4-methyl-imidazol-1-yl)-phenylamino]-4-trifluoromethyl-thiazole-5-carboxylic acid ethyl ester as a light yellow solid. MS ISP (m/e): 427.1 (100) (M+H)$^+$. $^1$H NMR (DMSO-D$_6$, 250 MHz): δ (ppm)=11.27 (s, 1H), 7.71 (s, 1H), 7.60 (s, 1H), 7.37 (d, 1H), 7.18 (d, 1H), 7.08 (d, 1H), 4.29 (q, 1H), 3.81 (s, 3H), 2.15 (s, 3H), 1.28 (t, 3H).

EXAMPLE 43

2-[3-Methoxy-4-(4-methyl-imidazol-1-yl)-phenylamino]-6,7-dihydro-4H-thiazolo[5,4-c]pyridine-5-carboxylic acid tert-butyl ester a) 3-Bromo-4-oxo-piperidine-1-carboxylic acid tert-butyl ester To a solution of 1295 mg (5 mmol) 3-bromo-4-piperidone hydrobromide and 61 mg (0.5 mmol) 4-dimethyl aminopyridine in tetrahydrofurane (50 ml) was added at room temperature under nitrogen and stirring 646 mg (5 mmol) N,N-diisopropyl ethyl amine. The reaction was stirred at room temperature for 10 minutes. 1200 mg (5.5 mmol) di-tert.-butyl-dicarbonate was added and the reaction was stirred at room temperature over night. The reaction was diluted with water and extracted twice with diethyl ether. The combined organic layers were washed once with cold 1N aqueous HCl solution andonce with brine, dried over sodium sulphate, filtered and the solvent was evaporate under reduced pressure to yield 1240 mg (89%) 3-bromo-4-oxo-piperidine-1-carboxylic acid tert-butyl ester as a colorless oil which solidified to give a white solid. $^1$H NMR (CDCl$_3$, 250 MHz): δ (ppm)= 4.35 (br m, 1H), 3.98 (br m, 2H), 3.62 (br m, 2H), 3.04 (br m, 1H), 2.44 (m, 2H), 1.51 (s, 9H).

b) 2-[3-Methoxy-4-(4-methyl-imidazol-1-yl)-phenylamino]-6,7-dihydro-4H-thiazolo[5,4-c]pyridine-5-carboxylic acid tert-butyl ester The title compound was prepared in analogy to example 1 step e) from 92 mg (0.33 mmol) 3-bromo-4-oxo-piperidine-1-carboxylic acid tert-butyl ester, 79 mg (0.3 mmol) [3-methoxy-4-(4-methyl-imidazol-1-yl)-phenyl]-thiourea and 43 mg (0.33 mmol) N,N-diisopropyl ethyl amine. The reaction was poured onto water and extracted twice with ethyl acetate. The combined organic layers were washed with brine, dried over sodium sulphate, filtered and the solvent was evaporated in vacuo. The crude product was purified on silica gel with methylene chloride/methanol 19/1 yielding 99 mg (75%) 2-[3-methoxy-4-(4-methyl-imidazol-1-yl)-phenylamino]-6, 7-dihydro-4H-thiazolo[5,4-c]pyridine-5-carboxylic acid tert-butyl ester as a light yellow foam. MS ISP (m/e): 442.3 (100) (M+H)$^+$. $^1$H NMR (DMSO-D$_6$, 250 MHz): δ (ppm)= 10.32 (s, 1H), 7.64 (s, 1H), 7.47 (s, 1H), 7.31 (d, 1H), 7.25 (d, 1H), 7.02 (d, 1H), 4.43 (s, 2H), 3.78 (s, 3H), 3.64 (t, 2H), 2.63 (m, 2H), 2.14 (s, 3H), 1.43 (s, 9H).

EXAMPLE 44

[3-Methoxy-4-(4-methyl-imidazol-1-yl)-phenyl]-(4, 5,6,7-tetrahydro-thiazolo[5,4-c]pyridin-2-yl)-amine trihydrochloride 1347 mg (3.05 mmol) 2-[3-Methoxy-4-(4-methyl-imidazol-1-yl)-phenylamino]-6,7-dihydro-4H-thiazolo[5,4-c]pyridine-5-carboxylic acid tert-butyl ester was suspended in methylene chloride (30.5 ml) and 2M HCl in diethyl ether (15.3 ml) was added at room temperature. Initially a clear solution was obtained and then a solid precipitated. The reaction was stirred at room temperature over night. The reaction was diluted with diethyl ether, stirred for 15 minutes and the solid was filtered off, washed with diethyl ether and dried to yield 1370 mg (100%) [3-methoxy-4-(4-methyl-imidazol-1- yl)-phenyl]-(4,5,6,7-tetrahydro-thiazolo[5,4-c]pyridin-2-yl)-amine trihydrochloride as a light yellow solid. MS ISP (m/e): 342.1 (100) (M+H)$^+$. $^1$H NMR (DMSO-D$_6$, 250 MHz): δ (ppm)=10.91 (s, 1H), 9.68 (br, 2H), 9.31 (s, 1H), 7.66 (s, 2H), 7.48 (d, 1H), 7.45 (d, 1H), 4.22 (br s, 2H), 3.84 (s, 3H), 3.38 (m, 2H), 2.88 (m, 2H), 2.35 (s, 3H).

EXAMPLE 45

(4-Fluoro-phenyl)-{2-[3-methoxy-4-(4-methyl-imidazol-1-yl)-phenylamino]-6,7-dihydro-4H-thiazolo [5,4-c]pyridin-5-yl}-methanone 90 mg (0.2 mmol) [3-methoxy-4-(4-methyl-imidazol-1-yl)-phenyl]-(4,5,6,7-tetrahydro-thiazolo[5,4-c]pyridin-2-yl)-amine trihydrochloride and 33 mg (0.2 mmol) 4-fluorobenzoyl chloride were suspended in methylene chloride (2 ml) and 101 mg (1 mmol) triethyl amine was added at room temperature. The reaction was stirred over night, diluted with methylene chloride, washed once with water, once with brine, dried over sodium sulphate, filtered and the solvent was evaporated under reduced pressure. The reaction was purified on silica gel with methylene chloride/methanol 19/1 yielding 52 mg (56%) (4-fluoro-phenyl)-{2-[3-methoxy-4-(4-methyl-imidazol-1-yl)-phenylamino]-6,7-dihydro-4H-thiazolo[5,4-c]pyridin-5-yl}-methanone as a yellow solid. MS ISP (m/e): 464.1 (100) (M+H)$^+$. $^1$H NMR (DMSO-D$_6$, 250 MHz): δ (ppm) 10.34 (s, 1H), 7.57-7.49 (m, 3H), 7.34-7.24 (m, 4H), 7.02 (d, 1H), 4.70-4.45 (br m, 2H), 4.00-3.55 (br m, 2H), 3.78 (s, 3H), 2.73 (m, 2H), 2.14 (s, 3H).

EXAMPLE 46

3,3,3-Trifluoro-1-{2-[3-methoxy-4-(4-methyl-imidazol-1-yl)-phenylamino]-6,7-dihydro-4H-thiazolo[5, 4-c]pyridin-5-yl}-propan-1-one The title compound was prepared in analogy to example 45 from 90 mg (0.2 mmol) [3-methoxy-4-(4-methyl-imidazol-1-yl)-phenyl]-(4,5,6,7-tetrahydro-thiazolo[5,4-c]pyridin-2-yl)-amine trihydrochloride and 30 mg (0.2 mmol) 3,3,3-trifluoropropionylchloride yielding 29 mg (32%) 3,3,3-trifluoro-1-{2-[3-methoxy-4-(4-methyl-imidazol-1-yl)-phenylamino]-6,7-dihydro-4H-thiazolo[5,4-c]pyridin-5-yl}-propan-1-one as a light yellow solid. MS ISP (m/e): 452.0 (100) (M+H)$^+$. $^1$H NMR (DMSO-D$_6$, 250 MHz): δ (ppm)= 10.33 (s, 1H), 7.65 (S, 1 h), 7.47 (S, 1 h), 7.30-7.25 (m, 2H), 7.02 (s, 1H), 4.57 (br s, 2H), 3.85-3.59 (br m, 2H), 3.78 (s, 3H), 2.75 (m, 1H), 2.62 (m, 1H), 2.14 (s, 3H).

EXAMPLE 47

1-{2-[3-Methoxy-4-(4-methyl-imidazol-1-yl)-phenylamino]-6,7-dihydro-4H-thiazolo[5,4-c]pyridin-5-yl}-2,2-dimethyl-propan-1-one The title compound was prepared in analogy to example 45 from 90 mg (0.2 mmol) [3-methoxy-4-(4-methyl-imidazol-1-yl)-phenyl]-(4,5,6,7-tetrahydro-thiazolo[5,4-c]pyridin-2-yl)-amine trihydrochloride and 25 mg (0.2 mmol) pivoloyl-chloride yielding 53 mg (62%) 1-{2-[3-methoxy-4-(4-methyl-imidazol-1-yl)-phenylamino]-6,7-dihydro-4H-thiazolo[5,4-c]pyridin-5-yl}-2,2-dimethyl-propan-1-one as a light yellow solid. MS ISP (m/e): 426.1 (100) (M+H)$^+$. $^1$H NMR (DMSO-D$_6$, 250 MHz): δ (ppm)=10.33 (s, 1H), 7.65 (s, 1H), 7.48 (s, 1H), 7.30 (d, 1H), 7.25 (d, 1H), 7.02 (s, 1H), 4.60 (br s, 2H), 3.83 (br t, 2H), 3.78 (s, 3H), 2.68 (br t, 2H), 2.14 (s, 3H).

EXAMPLE 48

[5-(4-Fluoro-benzenesulfonyl)-4,5,6,7-tetrahydro-thiazolo[5,4-c]pyridin-2-yl]-[3-methoxy-4-(4-methyl-imidazol-1-yl)-phenyl]-amine The title compound was prepared in analogy to example 45 from 90 mg (0.2 mmol) [3-methoxy-4-(4-methyl-imidazol-1-yl)-phenyl]-(4,5,6,7-tetrahydro-thiazolo[5,4-c]pyridin-2-yl)-amine trihydrochloride and 40 mg (0.2 mmol) 4-fluorobenzenesulfonylchloride yielding 74 mg (74%) of [5-(4-fluoro-benzenesulfonyl)-4,5,6,7-tetrahydro-thiazolo[5,4-c]pyridin-2-yl]-[3-methoxy-4-(4-methyl-imidazol-1-yl)-phenyl]-amine as a yellow solid. MS ISP (m/e): 499.9 (100) (M+H)$^+$. $^1$H NMR (DMSO-D$_6$, 250 MHz): δ (ppm)=10.31 (s, 1H), 7.91 (dd, 2H), 7.64 (s, 1H), 7.48 (t, 2H), 7.43 (s, 1H), 7.25 (s, 2H), 7.01 (s, 1H), 4.25 (br s, 2H), 3.77 (s, 3H), 3.43 (t, 2H), 2.64 (br t, 2H), 2.13 (s, 3H).

EXAMPLE 49

(5-Methanesulfonyl-4,5,6,7-tetrahydro-thiazolo[5,4-c]pyridin-2-yl)-[3-methoxy-4-(4-methyl-imidazol-1-yl)-phenyl]-amine The title compound was prepared in analogy to example 45 from 90 mg (0.2 mmol) [3-methoxy-4-(4-methyl-imidazol-1-yl)-phenyl]-(4,5,6,7-tetrahydro-thiazolo[5,4-c]pyridin-2-yl)-amine trihydrochloride and 23 mg (0.2 mmol) methanesulfonyl chloride yielding 39 mg (46%) (5-methanesulfonyl-4,5,6,7-tetrahydro-thiazolo[5,4-c]pyridin-2-yl)-[3-methoxy-4-(4-methyl-imidazol-1-yl)-phenyl]-amine as a yellow solid. MS ISP (m/e): 420.1 (100) (M+H)$^+$. $^1$H NMR (DMSO-D$_6$, 250 MHz): δ (ppm)=10.38 (s, 1H), 7.65 (s, 1H), 7.48 (s, 1H), 7.30 (d, 1H), 7.25 (d, 1H), 7.02 (s, 1H), 4.34 (br s, 2H), 3.79 (s, 3H), 3.52 (t, 2H), 2.96 (s, 3H), 2.76 (br t, 2H), 2.14 (s, 3H).

EXAMPLE 50

[3-Methoxy-4-(4-methyl-imidazol-1-yl)-phenyl]-(5-phenylmethanesulfonyl-4,5,6,7-tetrahydro-thiazolo [5,4-c]pyridin-2-yl)-amine The title compound was prepared in analogy to example 45 from 90 mg (0.2 mmol) [3-methoxy-4-(4-methyl-imidazol-1-yl)-phenyl]-(4,5,6,7-tetrahydro-thiazolo[5,4-c]pyridin-2-yl)-amine trihydrochloride and 39 mg (0.2 mmol) alpha-toluenesulphonylchloride yielding 18 mg (18%) [3-methoxy-4-(4-methyl-imidazol-1-yl)-phenyl]-(5-phenylmethanesulfonyl-4,5,6,7-tetrahydro-thiazolo[5,4-c]pyridin-2-yl)-amine as a yellow solid. MS ISP (m/e): 496.1 (100) (M+H)$^+$. $^1$H NMR (DMSO-D$_6$, 250 MHz): δ (ppm)= 10.36 (s, 1H), 7.64 (s, 1H), 7.47 (s, 1H), 7.38-7.35 (m, 6H), 7.30 (d, 1H), 7.25 (d, 1H), 7.02 (s, 1H), 4.50 (s, 2H), 4.29 (s, 2H), 3.78 (s, 3H), 3.48 (t, 2H), 2.64 (br t, 2H), 2.14 (s, 3H).

EXAMPLE 51

[5-(4-Fluoro-benzyl)-4,5,6,7-tetrahydro-thiazolo[5,4-c]pyridin-2-yl]-[3-methoxy-4-(4-methyl-imidazol-1-yl)-phenyl]-amine 90 mg (0.2 mmol) [3-methoxy-4-(4-methyl-imidazol-1-yl)-phenyl]-(4,5,6,7-tetrahydro-thiazolo[5,4-c]pyridin-2- yl)-amine trihydrochloride was suspended in tetrahydrofurane (3 ml). At room temperature under nitrogen 103 mg (0.8 mmol) N,N-diisopropyl ethyl amine was added and the reaction was stirred for 10 minutes. 28 mg (0.22 mmol) 4-fluorobenzaldehyde, 24 mg (0.4 mmol) acetic acid and 127 mg (0.6 mmol) sodium triacetoxyborohydride were added and the reaction was stirred at room temperature over night. 2N aqueous NaOH solution (6 ml) was added and the reaction was extracted twice with diethyl ether. The combined organic layers were washed with brine, dried over sodium sulphate, filtered and the solvent was evaporated under reduced pressure. The crude product was purified on silica gel with methylene chloride/methanol 19/1 yielding 58 mg (65%) [5-(4-fluoro-benzyl)-4,5,6,7-tetrahydro-thiazolo[5,4-c]pyridin-2-yl]-[3-methoxy-4-(4-methyl-imidazol-1-yl)-phenyl]-amine as a yellow solid. MS ISP (m/e): 450.1 (100) (M+H)$^+$. $^1$H NMR (DMSO-D$_6$, 250 MHz): δ (ppm)=10.25 (s, 1H), 7.64 (s, 1H), 7.47 (s, 1H), 7.39 (dd, 2H), 7.30 (d, 1H), 7.24 (d, 1H), 7.16 (t, 2H), 7.01 (s, 1H), 3.77 (s, 3H), 3.68 (s, 2H), 3.48 (s, 2H), 2.78 (m, 3H), 2.64 (m, 2H), 2.14 (s, 3H).

EXAMPLE 52

[3-Methoxy-4-(4-methyl-imidazol-1-yl)-phenyl]-(5-phenethyl-4,5,6,7-tetrahydro-thiazolo[5,4-c]pyridin-2-yl)-amine The title compound was prepared in analogy to example 51 from 90 mg (0.2 mmol) [3-methoxy-4-(4-methyl-imidazol-1-yl)-phenyl]-(4,5,6,7-tetrahydro-thiazolo[5,4-c]pyridin-2-yl)-amine trihydrochloride and 27 mg (0.22 mmol) phenylacetaldehyde yielding 44 mg (49%) of [3-methoxy-4-(4-methyl-imidazol-1-yl)-phenyl]-(5-phenethyl-4,5,6,7-tetrahydro-thiazolo[5,4-c]pyridin-2-yl)-amine as a yellow solid. MS ISP (m/e): 446.1 (100) (M+H)$^+$. $^1$H NMR (DMSO-D$_6$, 250 MHz): δ (ppm)=10.25 (s, 1H), 7.64 (s, 1H), 7.48 (s, 1H), 7.29-7.18 (m, 7H), 7.01 (s, 1H), 3.78 (s, 3H), 3.58 (s, 2H), 2.88-2.71 (m, 6H), 2.63 (m, 2H), 2.14 (s, 3H).

EXAMPLE 53

2-(4-Fluoro-phenyl)-1-{2-[3-methoxy-4-(4-methyl-imidazol-1-yl)-phenylamino]-6,7-dihydro-4H-thiazolo[5,4-c]pyridin-5-yl}-ethanone To a solution of 90 mg (0.2 mmol) [3-methoxy-4-(4-methyl-imidazol-1-yl)-phenyl]-(4,5,6,7-tetrahydro-thiazolo[5,4-c]pyridin-2-yl)-amine trihydrochloride and 35 mg (0.22 mmol) 4-fluorophenylacetic acid in DMF (2 ml) 121 mg (1.2 mmol) N-methyl morpholine and 114 mg (0.3 mmol) HBTU were added. The reaction was stirred over night at room temperature. The reaction was diluted with 2N aqueous NaOH solution (6 ml) and extracted twice with ethyl acetate. The combined organic layers were dried over sodium sulphate, filtered and the solvent was evaporated under reduced pressure. The crude product was purified on silica gel with methylene chloride/methanol 19/1 yielding 70 mg (73%) 2-(4-fluoro-phenyl)-1-{2-[3-methoxy-4-(4-methyl-imidazol-1-yl)-phenylamino]-6,7-dihydro-4H-thiazolo[5,4-c]pyridin-5-yl}-ethanone as a yellow viscous oil. MS ISP (m/e): 478.0 (100) (M+H)$^+$. $^1$H NMR (DMSO-D$_6$, 250 MHz): δ (ppm)=10.32 (s, 1H), 7.65 (s, 1H), 7.46 (s, 1H), 7.32-7.24 (m, 4H), 7.30 (d, 1H), 7.24 (d, 1H), 7.02 (s, 1H), 4.65 & 4.55 (br s, 2H), 3.84 (m, 2H), 3.78 (s, 3H), 2.89 (s, 2H), 2.62 (m, 2H), 2.14 (s, 3H).

EXAMPLE 54

2-Methoxy-1-{2-[3-methoxy-4-(4-methyl-imidazol-1-yl)-phenylamino]-6,7-dihydro-4H-thiazolo[5,4-c]pyridin-5-yl}-ethanone The title compound was prepared in analogy to example 53 from 90 mg (0.2 mmol) [3-methoxy-4-(4-methyl-imidazol-1-yl)-phenyl]-(4,5,6,7-tetrahydro-thiazolo[5,4-c]pyridin-2-yl)-amine trihydrochloride and 20 mg (0.22 mmol) methoxyacetic acid yielding 46 mg (56%) 2-methoxy-1-{2-[3-methoxy-4-(4-methyl-imidazol-1-yl)-phenylamino]-6,7-dihydro-4H-thiazolo[5,4-c]pyridin-5-yl}-ethanone as a light yellow solid. MS ISP (m/e): 414.2 (100) (M+H)$^+$. $^1$H NMR (DMSO-D$_6$, 250 MHz): δ (ppm)=10.32 (s, 1H), 7.65 (s, 1H), 7.48 (s, 1H), 7.29 (d, 1H), 7.24 (d, 1H), 7.02 (s, 1H), 4.54 (br s, 2H), 4.20 & 4.14 (s, 2H), 3.78 (s, 3H), 3.78 & 3.68 (m, 2H), 3.32 (s, 3H), 2.73-2.60 (m, 2H), 2.14 (s, 3H).

EXAMPLE 55

N—((S)-1-{2-[3-Methoxy-4-(4-methyl-imidazol-1-yl)-phenylamino]-thiazol-4-yl}-2-phenyl-ethyl)-4-methyl-benzenesulfonamide The title compound was prepared in analogy to example 1 step e) from 116 mg (0.33 mmol) (S)-1-tosylamide-2-phenyl-ethyl-chloromethylketone and 79 mg (0.3 mmol) [3-methoxy-4-(4-methyl-imidazol-1-yl)-phenyl]-thiourea. The crude reaction was stirred with methylene chloride/diethyl ether. The precipitate was filtered off and purified on silica gel with methylene chloride/methanol 19/1 yielding 124 mg (74%) N—((S)-1-{2-[3-methoxy-4-(4-methyl-imidazol-1-yl)-phenylamino]-thiazol-4-yl}-2-phenyl-ethyl)-4-methyl-benzenesulfonamide as a light yellow solid. MS ISP (m/e): 559.8 (100) (M+H)$^+$. $^1$H NMR (DMSO-D$_6$, 250 MHz): δ (ppm) 10.25 (s, 1H), 8.17 (d, 1H), 7.81 (s, 1H), 7.67 (s, 1H), 7.42 (d, 2H), 7.23 (d, 1H), 7.24-7.04 (m, 9H), 6.39 (s, 1H), 4.42 (q, 2H), 3.85 (s, 3H), 3.09 (dd, 1H), 2.93 (dd, 1H), 2.26 (s, 3H), 2.15 (s, 3H).

EXAMPLE 56

2-[3-Methoxy-4-(4-methyl-imidazol-1-yl)-phenylamino]-thiazole-5-carbaldehyde

The title compound was prepared in analogy to example 1 step e) from 78 mg (0.5 mmol) bromomalonaldehyde, 82 mg (1 mmol) sodium acetate and 131 mg (0.5 mmol) [3-methoxy-4-(4-methyl-imidazol-1-yl)-phenyl]-thiourea. The solvent was evaporated. The reaction was diluted with water and extracted twice with ethyl acetate and twice with methylene chloride/methanol 9/1. The combined organic layers were washed with brine, dried over sodium sulphate, filtered and the solvent was evaporated under reduced pressure. The crude product was stirred diethyl ether to yield 88 mg (56%) of 2-[3-methoxy-4-(4-methyl-imidazol-1-yl)-phenylamino]-thiazole-5-carbaldehyde as a yellow solid. MS ISP (m/e): 315.1 (100) (M+H)$^+$. $^1$H NMR (DMSO-D$_6$, 250 MHz): δ (ppm)=11.35 (br s, 1H), 9.80 (s, 1H), 8.27 (s, 1H), 7.70 (s, 1H), 7.55 (s, 1H), 7.38 (d, 1H), 7.33 (d, 1H), 7.07 (s, 1H), 3.82 (s, 3H), 2.15 (s, 3H).

EXAMPLE 57

{5-[(4-Fluoro-phenylamino)-methyl]-thiazol-2-yl}-[3-methoxy-4-(4-methyl-imidazol-1-yl)-phenyl]-amine 21 mg (0.19 mmol) 4-Fluoroaniline was dissolved in tetrahydrofurane (1 ml). 65 mg (0.21 mmol) 2-[3-methoxy-4-

(4-methyl-imidazol-1-yl)-phenylamino]-thiazole-5-carbaldehyde was added. The suspension was stirred at room temperature for 10 minutes. 133 mg (0.56 mmol) sodium triacetoxyborohydride and 23 mg (0.38 mmol) acetic acid were added and the reaction was stirred at room temperature over night. Since the reaction was not complete the same amount of 4-fluoroaniline, sodium triacetoxyborohydride and acetic acid were added and the reaction stirred at room temperature over night. 2N aqueous NaOH solution was added and the reaction was extracted once with methylene chloride. The organic layer was washed with brine, dried over sodium sulphate, filtered and the solvent was evaporated under reduced pressure. The crude product was purified on silica gel with ethyl acetate yielding 22 mg (26%) [5-(4-fluoro-benzyl)-4,5,6,7-tetrahydro-thiazolo[5,4-c]pyridin-2-yl]-[3-methoxy-4-(4-methyl-imidazol-1-yl)-phenyl]-amine as a light yellow solid. MS ISP (m/e): 410.1 (100) $(M+H)^+$. $^1$H NMR (CDCl$_3$, 250 MHz): δ (ppm)=7.63 (s, 1H), 7.28-7.16 (m, 4H), 6.95-6.87 (m, 4H), 6.66-6.60 (m, 2H), 4.39 (s, 2H), 3.85 (s, 3H), 2.29 (s, 3H).

EXAMPLE 58

[3-Methoxy-4-(4-methyl-imidazol-1-yl)-phenyl]-(5-piperidin-1-ylmethyl-thiazol-2-yl)-amine The title compound was prepared in analogy to example 57 from 16 mg (0.19 mmol) piperidine and 65 mg (0.21 mmol) 2-[3-methoxy-4-(4-methyl-imidazol-1-yl)-phenylamino]-thiazole-5-carbaldehyde. The reaction was not complete and the same amount of reagent was added like in example 57. The crude product was purified on silica gel with methylene chloride/methanol 9/1 yielding 36 mg (50%) [3-methoxy-4-(4-methyl-imidazol-1-yl)-phenyl]-(5-piperidin-1-ylmethyl-thiazol-2-yl)-amine as a yellow oil. MS ISP (m/e): 384.3 (100) $(M+H)^+$. $^1$H NMR (CDCl$_3$, 250 MHz): δ (ppm)=7.64 (s, 1H), 7.25 (d, 1H), 7.18 (d, 1H), 7.08 (s, 1H), 6.96 (d, 1H), 6.87 (s, 1H), 3.85 (s, 3H), 3.59 (s, 2H), 2.42 (m, 4H), 2.30 (s, 3H), 1.59-1.54 (m, 4H), 1.45-1.43 (m, 2H).

EXAMPLE 59

(5-Cyclohexylaminomethyl-thiazol-2-yl)-[3-methoxy-4-(4-methyl-imidazol-1-yl)-phenyl]-amine The title compound was prepared in analogy to example 57 from 19 mg (0.19 mmol) cyclohexylamine and 65 mg (0.21 mmol) 2-[3-methoxy-4-(4-methyl-imidazol-1-yl)-phenylamino]-thiazole-5-carbaldehyde using a solvent mixture of tetrahydrofurane (1 ml), methanol (1 ml) and methylene chloride (1 ml). The reaction was not complete and the same amount of reagent was added like in example 57. Only the imine was formed. Therefore the crude product was dissolved in methanol (1 ml) and 8.6 mg sodium borohydride was added and the reaction stirred for 4 hours at room temperature. After workup the crude product was purified on silica gel with methylene chloride/methanol 9/1 yielding 16 mg (21%) of (5-cyclohexylaminomethyl-thiazol-2-yl)-[3-methoxy-4-(4-methyl-imidazol-1-yl)-phenyl]-amine as a yellow oil. MS ISP (m/e): 398.3 (100) $(M+H)^+$. $^1$H NMR (CDCl$_3$, 250 MHz): δ (ppm)=7.62 (s, 1H), 7.25 (s, 1H), 7.16 (d, 1H), 7.10 (s, 1H), 6.96 (d, 1H), 6.87 (s, 1H), 3.94 (s, 2H), 3.85 (s, 3H), 2.54 (m, 1H), 2.30 (s, 3H), 1.93 (m, 2H), 1.72 (m, 2H), 1.64 (m, 1H), 1.28-1.09 (m, 5H).

EXAMPLE 60

[3-Methoxy-4-(4-methyl-imidazol-1-yl)-phenyl]-(5-morpholin-4-ylmethyl-thiazol-2-yl)-amine The title compound was prepared in analogy to example 57 from 17 mg (0.19 mmol) morpholine and 65 mg (0.21 mmol) 2-[3-methoxy-4-(4-methyl-imidazol-1-yl)-phenylamino]-thiazole-5-carbaldehyde using a solvent mixture of tetrahydrofurane (1 ml), and methylene chloride (1 ml). The crude product was purified on silica gel with methylene chloride/methanol 9/1 yielding 43 mg (59%) [3-methoxy-4-(4-methyl-imidazol-1-yl)-phenyl]-(5-morpholin-4-ylmethyl-thiazol-2-yl)-amine as a yellow oil. MS ISP (m/e): 386.2 (100) $(M+H)^+$. $^1$H NMR (CDCl$_3$, 250 MHz): δ (ppm)=7.65 (s, 1H), 7.27 (s, 1H), 7.19 (d, 1H), 7.11 (s, 1H), 6.97 (d, 1H), 6.87 (s, 1H), 3.86 (s, 3H), 3.71 (t, 4H), 3.61 (s, 2H), 2.49 (t, 4H), 2.30 (s, 3H).

EXAMPLE 61

{5-[(2-Methoxy-ethylamino)-methyl]-thiazol-2-yl}-[3-methoxy-4-(4-methyl-imidazol-1-yl)-phenyl]-amine The title compound was prepared in analogy to example 57 from 14 mg (0.19 mmol) 2-methoxyethylamine and 65 mg (0.21 mmol) 2-[3-methoxy-4-(4-methyl-imidazol-1-yl)-phenylamino]-thiazole-5-carbaldehyde using a solvent mixture of tetrahydrofurane (2 ml), and methylene chloride (1 ml). The reaction was not complete and the same amount of reagent was added like in example 57. The crude product was purified on silica gel with methylene chloride/methanol 9/1 yielding 47 mg (54%) {5-[(2-methoxy-ethylamino)-methyl]-thiazol-2-yl}-[3-methoxy-4-(4-methyl-imidazol-1-yl)-phenyl]-amine as a yellow oil. MS ISP (m/e): 374.2 (100) $(M+H)^+$. $^1$H NMR (CDCl$_3$, 250 MHz): δ (ppm)=7.64 (s, 1H), 7.26 (s, 1H), 7.18 (d, 1H), 7.12 (s, 1H), 6.95 (d, 1H), 6.87 (s, 1H), 3.93 (s, 2H), 3.85 (s, 3H), 3.51 (t, 2H), 3.36 (s, 3H), 2.83 (t, 2H), 2.30 (s, 3H).

EXAMPLE 62

{2-[3-Methoxy-4-(4-methyl-imidazol-1-yl)-phenylamino]-thiazol-5-yl}-phenyl-methanol To a solution of 100 mg (0.32 mmol) 2-[3-methoxy-4-(4-methyl-imidazol-1-yl)-phenylamino]-thiazole-5-carbaldehyde in DMPU (1 ml) and tetrahydrofurane (2 ml) was added slowly 0.67 ml (1.27 mmol) 1.9 M phenyl lithium solution in diethyl ether at −72° C. under nitrogen. The reaction was warmed to 0° C. over 40 minutes. The solvent was evaporated under reduced pressure. The residue was partitioned between in ethyl acetate and 1N aqueous NaOH solution. The aqueous layer was extracted once with ethyl acetate. The combined organic layers were washed twice with water, dried over sodium sulphate, filtered and the solvent was evaporated under reduced pressure. The residue was purified on silica gel with methylene chloride/methanol 9/1 yielding 39 mg (22%) {2-[3-methoxy-4-(4-methyl-imidazol-1-yl)-phenylamino]-thiazol-5-yl}-phenyl-methanol as a yellow oil. MS ISP (m/e): 393.0 (100) $(M+H)^+$. $^1$H NMR (CDCl$_3$, 250 MHz): δ (ppm)= 7.56 (s, 1H), 7.47-6.84 (m, 11H), 5.99 (s, 1H), 3.79 (s, 3H), 2.28 (s, 3H).

EXAMPLE 63

(5-Benzyl-thiazol-2-yl)-[3-methoxy-4-(4-methyl-imidazol-1-yl)-phenyl]-amine

To a solution of 35 mg (0.09 mmol) {2-[3-methoxy-4-(4-methyl-imidazol-1-yl)-phenylamino]-thiazol-5-yl}-phenyl-methanol in methylene chloride (2 ml) 12 mg (0.1 mmol) triethylsilane was added at room temperature and trifluoro acetate (2 ml) was added. The reaction was stirred at room temperature for 6 hours and the solvent was evaporated under reduced pressure. The residue was suspended in saturated aqueous sodium hydrogen carbonate solution and extracted twice with methylene chloride. The combined organic layers were washed with brine, dried over sodium sulphate, filtered and the solvent was evaporated under reduced pressure to yield 33 mg (98%) (5-benzyl-thiazol-2-yl)-[3-methoxy-4-(4-methyl-imidazol-1-yl)-phenyl]-amine as a brown solid. MS ISP (m/e): 377.4 (100) (M+H)$^+$. $^1$H NMR (CDCl$_3$, 250 MHz): δ (ppm)=7.64 (s, 1H), 7.53 (s, 1H), 7.35-7.22 (m, 7H), 7.07 (s, 1H), 7.01 (s, 1H), 4.03 (s, 2H), 3.77 (s, 3H), 2.13 (s, 3H).

EXAMPLE 64

4-(4-Bromo-imidazol-1-yl)-3-methoxy-phenyl]-[4-(5-bromo-2-methoxy-phenyl)-thiazol-2-yl]-amine a) 4-Bromo-1-(2-methoxy-4-nitro-phenyl)-1H-imidazole A mixture of 2.0 g (10.7 mmol) 2-chloro-5-nitroanisole, 1.65 g (11.2 mmol) 4-bromoimidazole and 5.21 g (16.0 mmol) cesium carbonate in 50 ml acetonitrile was refluxed overnight. The reaction mixture was concentrated, diluted with water and extracted with ethyl acetate. The organic phase was dried, evaporated and the residue purified on silica gel with ethyl acetate/heptane 3/7. After trituration with diethyl ether 707 mg (22%) of 4-bromo-1-(2-methoxy-4-nitro-phenyl)-1H-imidazole was isolated as a slightly brownish solid. MS ISP (m/e): 298.1/300.0 (100/87) (M+H)$^+$. $^1$H NMR (CDCl$_3$, 300 MHz): δ (ppm)=7.96 (d, 2H), 7.77 (s, 1H), 7.44 (d, 1H), 7.26 (s, 1H), 4.02 (s, 3H).

b) 4-(4-Bromo-imidazol-1-yl)-3-methoxy-phenylamine 700 mg (2.35 mmol) 4-bromo-1-(2-methoxy-4-nitro-phenyl)-1H-imidazole and 2.755 g (12.2 mmol) stannous chloride dihydrate were suspended in a mixture of 40 ml ethyl acetate and 10 ml ethanol and stirred for 1 h at 70° C. The resulting mixture was poured into cold water and neutralized by addition of a saturated solution of sodium hydrogen carbonate. The product was extracted with ethyl acetate, dried and evaporated to give 627 mg (100%) of 4-(4-bromo-imidazol-1-yl)-3-methoxy-phenylamine as a yellowish solid. MS ISP (m/e): 268.0/270.1 (100/82) (M+H)$^+$. $^1$H NMR (CDCl$_3$, 300 MHz): δ (ppm)=7.49 (s, 1H), 7.77 (s, 1 H), 7.05 (s, 1H), 6.99 (d, 2H), 6.35-6.25 (m, 2H), 3.86 (s broad, 2H), 3.77 (s, 3H).

c) 4-(4-Bromo-imidazol-1-yl)-3-methoxy-phenyl]-thiourea

Prepared in analogy to example 4b) from 620 mg (2.31 mmol) 4-(4-bromo-imidazol-1-yl)-3-methoxy-phenylamine and 396 mg (2.43 mmol) benzoylisothiocyanate. 624 mg (82%) of the product was isolated as a yellowish solid. MS ISP (m/e): 327.1/329.0 (100/87) (M+H)$^+$. $^1$H NMR (CDCl$_3$, 300 MHz): δ (ppm)=9.90 (s broad, 1H), 7.84 (d, 1 H), 7.53 (d, 2H), 7.35 (d, 1H), 7.07 (dxd, 1H), 3.80 (s, 3H).

d) 4-(4-Bromo-imidazol-1-yl)-3-methoxy-phenyl]-[4-(5-bromo-2-methoxy-phenyl)-thiazol-2-yl]-amine A suspension of 200 mg (0.61 mmol) 4-(4-bromo-imidazol-1-yl)-3-methoxy-phenyl]-thiourea and 198 mg (0.64 mmol) 2-bromo-1-(5-bromo-2-methoxyphenyl)acetone in 10 ml of ethanol was stirred at 70° for 1 hour. The resulting precipitate was filtered and dried to yield 258 mg (79%) of the title compound as a colorless solid. MS ISN (m/e): 535.2/537.2 (100/29) (M−H)$^-$. $^1$H NMR (DMSO-D$_6$, 300 MHz): δ (ppm)=10.62 (s broad, 1H), 8.31 (dd, 2H), 7.92 (d, 1H), 7.57 (dd, 2H), 7.47 (dd, 1H), 7.37 (d, 1H), 7.12 (d, 1H), 6.97 (dd, 1H), 3.97 (s, 3H), 3.95 (s, 3H).

EXAMPLE 65

4-(5-Bromo-2-methoxy-phenyl)-thiazol-2-yl]-[3-isopropoxy-4-(4-methyl-imidazol-1-yl)-phenyl]-amine a) 1-(2-Isopropoxy-4-nitro-phenyl)-4-methyl-1H-imidazole A solution of 2.0 g (11.5 mmol) 2-chloro-5-nitrophenol in 15 ml of acetonitrile was treated with 11.26 g (34.6 mmol) cesium carbonate and 2.06 g (12.1 mmol) 2-iodopropane and heated overnight at reflux temperature. 993 mg (12.1 mmol) of 4-methylimidazole was added and the mixture refluxed again overnight. After evaporation of the solvent, water was added and the crude material extracted with ethyl acetate. The product was purified on silica gel with ethyl acetate to give 337 mg (11%) of 1-(2-isopropoxy-4-nitro-phenyl)-4-methyl-1H-imidazole as a slightly brownish solid. MS ISP (m/e): 262.0 (100) (M+H)$^+$. $^1$H NMR (CDCl$_3$, 300 MHz): δ (ppm)= 7.95-7.85 (m, 3H), 7.40 (d, 1H), 6.99 (s, 1H), 4.73 (sept, 1H), 2.31 (s, 3H), 1.40 (d, 6H).

b) 3-Isopropoxy-4-(4-methyl-imidazol-1-yl)-phenylamine

Prepared in analogy to example 64b) from 330 mg (1.26 mmol) 1-(2-isopropoxy-4-nitro-phenyl)-4-methyl-1H-imidazole and 1.48 g (6.56 mmol) stannous chloride dihydrate. 269 mg (92%) of the product was isolated as a yellowish gum. MS ISP (m/e): 232.1 (100) (M+H)$^+$. $^1$H NMR (CDCl$_3$, 300 MHz): δ (ppm)=7.57 (s, 1H), 7.00 (d, 1 H), 6.80 (s, 1H), 6.33 (d, 1H), 6.28 (dd, 1H), 4.39 (sept, 1H), 3.75 (s broad, 2H), 2.28 (s, 3H), 1.25 (d, 6H).

c) [3-Isopropoxy-4-(4-methyl-imidazol-1-yl)-phenyl]-thiourea

Prepared in analogy to example 64c) from 260 mg (1.12 mg) 3-isopropoxy-4-(4-methyl-imidazol-1-yl)-phenylamine and 193 mg (1.18 mmol) benzoylisothiocyanate. 157 mg (48%) of the product was isolated as a slightly brownish solid. MS ISP (m/e): 291.0 (100) (M+H)$^+$. $^1$H NMR (DMSO-D$_6$, 300 MHz): δ (ppm)=9.82 (s broad, 1H), 7.73 (s, 1 H), 7.54 (s, 1H), 7.27 (d, 1H), 7.08 (s, 1H), 6.97 (d, 1H), 4.53 (sept, 1H), 2.14 (s, 3H), 1.26 (d, 6H).

d) 4-(5-Bromo-2-methoxy-phenyl)-thiazol-2-yl]-[3-isopropoxy-4-(4-methyl-imidazol-1-yl)-phenyl]-amine Prepared in analogy to example 64d) from 150 mg (0.52 mmol) [3-isopropoxy-4-(4-methyl-imidazol-1-yl)-phenyl]-thiourea and 175 mg (0.57 mmol) 2-bromo-1-(5-bromo-2-methoxyphenyl)acetone. 235 mg (91%) of the product was isolated as a slightly brownish solid. MS EI (m/e): 498.2/500.2 (100/84) (M$^+$). $^1$H NMR (CDCl$_3$, 300 MHz): δ (ppm)= 8.32 and 7.99 (s broad, 1H, rotamers), 7.45-6.80 (m, 9H, rotamers), 4.79 (sept, 1H), 3.96 and 3.94 (s, 3H, rotamers), 2.43 and 2.19 (s, 3H, rotamers), 1.44 and 1.40 (d, 6H, rotamers).

EXAMPLE 66

(1-{4-[4-(5-Bromo-2-methoxy-phenyl)-thiazol-2-ylamino]-2-methoxy-phenyl}-1H-imidazol-4-yl)-methanol a) [1-(2-Methoxy-4-nitro-phenyl)-1H-imidazol-4-yl]-methanol Prepared in analogy to example 64a) from 1.0 g (5.8 mmol) 4-fluoro-3-methoxybenzene, 602 mg (6.1 mmol) (1H-imidazol-4-yl)-methanol and 2.86 g (8.8 mmol) cesium carbonate. 517 mg (35%) of the product was isolated as yellowish solid.

MS ISP (m/e): 250.1 (51) (M+H)+. 1H NMR (CDCl3, 300 MHz): δ (ppm)=8.00-7.85 (m, 3H), 7.45 (d, 1 H), 7.26 (d, 1H), 4.70 (s, 2H), 4.01 (s, 3H).

b) [1-(4-Amino-2-methoxy-phenyl)-1H-imidazol-4-yl]-methanol

Prepared in analogy to example 64b) from 500 mg (2.0 mmol) [1-(2-methoxy-4-nitro-phenyl)-1H-imidazol-4-yl]-methanol and 2.35 g (10.4 mmol) stannous chloride dihydrate. 311 mg (71%) of the product was isolated as a yellowish viscous oil. MS ISP (m/e): 220.1 (46) (M+H)+. 1H NMR (CDCl3, 300 MHz): δ (ppm)=7.61 (s, 1H), 7.01 (d, 2 H), 6.35-6.25 (m, 2H), 4.66 (s, 2H), 3.85 (s broad, 2H), 3.77 (s, 3H).

c) (1-{4-[4-(5-Bromo-2-methoxy-phenyl)-thiazol-2-ylamino]-2-methoxy-phenyl}-1H-imidazol-4-yl)-methanol Prepared in analogy to example 64c) and 64d), without isolation of the intermediate thiourea, starting from 300 mg (1.37 mmol) [1-(4-amino-2-methoxy-phenyl)-1H-imidazol-4-yl]-methanol, 234 mg (1.43 mmol) benzoylisothiocyanate and 464 mg (1.51 mmol) 2-bromo-1-(5-bromo-2-methoxyphenyl)acetone. 336 mg (50%) of the product was isolated as a slightly brownish solid. MS ISN (m/e): 487.4/485.4 (100/89) (M−H)−. 1H NMR (DMSO-D6, 300 MHz): δ (ppm)= 10.71 and 10.66 (s broad, 1H, rotamers), 9.43 and 8.65 (s broad, 1H, rotamers), 8.40-7.00 (m, 8H, rotamers), 4.52 and 4.50 (s, 2H, rotamers), 3.98 (s, 3H), 3.95 (s, 3H).

EXAMPLE 67

[4-(5-Bromo-2-methoxy-phenyl)-thiazol-2-yl]-(3-methoxy-4-[1,2,3]triazol-1-yl-phenyl)-amine a) 1-(2-Methoxy-4-nitro-phenyl)-1H-[1,2,3]triazole Prepared in analogy to example 64 a) from 3.0 g (16.0 mmol) 4-chloro-3-methoxybenzene, 2.26 g (32.7 mmol) 1H-1,2,3-triazole and 7.82 g (24.0 mmol) cesium carbonate. 97 mg (3%) of the product was isolated as brownish solid. MS ISP (m/e): 221.1 (100) (M+H)+. 1H NMR (CDCl3, 300 MHz): δ (ppm)=8.33 (s, 1H), 8.17 (d, 1 H), 8.05 (dxd, 1H), 8.00 (d, 1H), 7.87 (s, 1H), 4.07 (s, 3H).

b) 3-Methoxy-4-[1,2,3]triazol-1-yl-phenylamine

Prepared in analogy to example 64b) from 150 mg (0.68 mmol) 1-(2-methoxy-4-nitro-phenyl)-1H-[1,2,3]triazole and 799 mg (3.54 mmol) stannous chloride dihydrate. 311 mg (71%) of the product was isolated as a yellowish viscous oil. MS ISP (m/e): 191.3 (100) (M+H)+. 1H NMR (CDCl3, 300 MHz): δ (ppm)=7.95 (s, 1H), 7.78 (s, 1 H), 7.45 (d, 1H), 6.36 (d, 2H), 3.92 (s broad, 2H), 3.81 (s, 3H).

c) [4-(5-Bromo-2-methoxy-phenyl)-thiazol-2-yl]-(3-methoxy-4-[1,2,3]triazol-1-yl-phenyl)-amine Prepared in analogy to example 64c) and 64d), without isolation of the intermediate thiourea, starting from 120 mg (0.63 mmol) [3-methoxy-4-[1,2,3]triazol-1-yl-phenylamine, 108 mg (0.66 mmol) benzoylisothiocyanate and 214 mg (0.69 mmol) 2-bromo-1-(5-bromo-2-methoxyphenyl)acetone. 22 mg (8%) of the product was isolated as a slightly greyish solid. MS ISN (m/e): 457.9/456.0 (100/98) (M−H)−. 1H NMR (DMSO-D6, 300 MHz): δ (ppm)=10.68 (s broad, 1H), 8.45-8.35 (m, 3H), 7.89 (s, 1H), 7.60-7.45 (m, 3H), 7.12 (d, 1H), 6.98 (d, 1H), 3.99 (s, 3H), 3.95 (s, 3H).

EXAMPLE 68

[5-(4-Chloro-3-trifluoromethyl-benzyl)-4-methyl-thiazol-2-yl]-[3-methoxy-4-(4-methyl-imidazol-1-yl)-phenyl]-amine a) 2-Chloro-1-(4-chloro-3-trifluoromethyl-phenyl)-butan-3-one The title compound was prepared in analogy to example 3 step a) from 195 mg (1 mmol) 4-chloro-3-trifluoromethylaniline, 421 mg (6 mmol) methyl vinylketone, 155 mg (1.5 mmol) tert.-butylnitrite, 161 mg (1.2 mmol) copper(II) chloride and 304 mg (2 mmol) DBU in acetonitrile (5 ml) to yield the crude product, which was used without further purification in the next step.

b) [5-(4-Chloro-3-trifluoromethyl-benzyl)-4-methyl-thiazol-2-yl]-[3-methoxy-4-(4-methyl-imidazol-1-yl)-phenyl]-amine The title compound was prepared in analogy to example 1 step e) from crude 2-chloro-1-(4-chloro-3-trifluoromethyl-phenyl)-butan-3-one and 53 mg (0.2 mmol) [3-methoxy-4-(4-methyl-imidazol-1-yl)-phenyl]-thiourea in ethanol (1 ml). The crude product was purified on silica gel with methylene chloride/methanol 9/1 yielding 87 mg (88%) of the title compound as a brown solid. MS ISP (m/e): 493.2/495.2 (100/35) (M+H)+. 1H NMR (CDCl3, 300 MHz): δ (ppm)=7.63 (s, 1H), 7.51 (s, 1H), 7.43 (d, 1H), 7.30 (d, 1H), 7.23 (s, 1H), 7.15 (d, 1H), 6.90 (d, 1H), 6.85 (s, 1H), 4.00 (s, 2H), 3.82 (s, 3H), 2.31 (s, 6H).

EXAMPLE 69

[3-Methoxy-4-(4-methyl-imidazol-1-yl)-phenyl]-{4-methyl-5-[3-(1,1,2,2-tetrafluoro-ethoxy)-benzyl]-thiazol-2-yl}-amine a) 2-Chloro-1-(3-(1,1,2,2-tetrafluoro-ethoxy)-phenyl)-butan-3-one The title compound was prepared in analogy to example 3 step a) from 209 mg (1 mmol) 3-tetrafluoroethoxy-aniline, 421 mg (6 mmol) methyl vinylketone, 155 mg (1.5 mmol) tert.-butylnitrite, 161 mg (1.2 mmol) copper(II) chloride and 304 mg (2 mmol) DBU in acetonitrile (5 ml) to yield the crude product, which was used without further purification in the next step.

b) [3-Methoxy-4-(4-methyl-imidazol-1-yl)-phenyl]-{4-methyl-5-[3-(1,1,2,2-tetrafluoro-ethoxy)-benzyl]-thiazol-2-yl}-amine The title compound was prepared in analogy to example 1 step e) from crude 2-chloro-1-(3-(1,1,2,2-tetrafluoro-ethoxy)-phenyl)-butan-3-one and 53 mg (0.2 mmol) [3-methoxy-4-(4-methyl-imidazol-1-yl)-phenyl]-thiourea in ethanol (1 ml). The crude product was purified on silica gel with methylene chloride/methanol 9/1 yielding 98 mg (96%) of the title compound as a brown solid. MS ISP (m/e): 507.3 (100) (M+H)+. 1H NMR (CDCl3, 300 MHz): δ (ppm)=7.63 (s, 1H), 7.31 (t, 1H), 7.20 (s, 1H), 7.15-7.04 (m, 4H), 6.88 (d, 1H), 6.85 (s, 1H), 6.08-5.38 (tt, 1H), 3.99 (s, 2H), 3.81 (s, 3H), 2.28 (s, 6H).

EXAMPLE 70

[5-(3-Chloro-4-methyl-benzyl)-4-methyl-thiazol-2-yl]-[3-methoxy-4-(4-methyl-imidazol-1-yl)-phenyl]-amine a) 2-Chloro-1-(3-chloro-4-methyl-phenyl)-butan-3-one The title compound was prepared in analogy to example 3 step a) from 141 mg (1 mmol) 3-chloro-4-methylaniline, 421 mg (6 mmol) methyl vinylketone, 155 mg (1.5 mmol) tert.-butylnitrite, 161 mg (1.2 mmol) copper(II) chloride and 304 mg (2 mmol) DBU in acetonitrile (5 ml) to yield the crude product, which was used without further purification in the next step.

b) [5-(3-Chloro-4-methyl-benzyl)-4-methyl-thiazol-2-yl]-[3-methoxy-4-(4-methyl-imidazol-1-yl)-phenyl]-amine The title compound was prepared in analogy to example 1 step e) from crude 2-chloro-1-(3-chloro-4-methyl-phenyl)-butan-3-one and 53 mg (0.2 mmol) [3-methoxy-4-(4-methyl-imidazol-1-yl)-phenyl]-thiourea in ethanol (1 ml). The crude product was purified on silica gel with methylene chloride/methanol 9/1 yielding 56 mg (64%) of the title compound as a brown solid. MS ISP (m/e): 439.3/440.3/441.2/442.2 (100/69/50/34) (M+H)$^+$. $^1$H NMR (CDCl$_3$, 300 MHz): δ (ppm)= 7.62 (s, 1H), 7.18-7.15 (m, 3H), 7.13 (s, 1H), 6.98 (d, 1H), 6.88 (d, 1H), 6.85 (s, 1H), 3.91 (s, 2H), 3.83 (s, 3H), 2.33 (s, 3H), 2.28 (s, 3H), 2.27 (s, 3H).

EXAMPLE 71

[5-(3,4-Dichloro-benzyl)-4-methyl-thiazol-2-yl]-[3-methoxy-4-(4-methyl-imidazol-1-yl)-phenyl]-amine a) 2-Chloro-1-(3,4-dichloro-phenyl)-butan-3-one The title compound was prepared in analogy to example 3 step a) from 162 mg (1 mmol) 3,4-dichloro-aniline, 421 mg (6 mmol) methyl vinylketone, 155 mg (1.5 mmol) tert.-butylnitrite, 161 mg (1.2 mmol) copper(II) chloride and 304 mg (2 mmol) DBU in acetonitrile (5 ml) to yield the crude product, which was used without further purification in the next step.
b) [5-(4-Chloro-3-trifluoromethyl-benzyl)-4-methyl-thiazol-2-yl]-[3-methoxy-4-(4-methyl-imidazol-1-yl)-phenyl]-amine The title compound was prepared in analogy to example 1 step e) from crude 2-chloro-1-(3,4-dichloro-phenyl)-butan-3-one and 53 mg (0.2 mmol) [3-methoxy-4-(4-methyl-imidazol-1-yl)-phenyl]-thiourea in ethanol (1 ml). The crude product was purified on silica gel with methylene chloride/methanol 9/1 yielding 85 mg (93%) of the title compound as a brown solid. MS ISP (m/e): 4.59.3/461.2/460.3/462.2 (100/74/35/20) (M+H)$^+$. $^1$H NMR (CDCl$_3$, 300 MHz): δ (ppm)= 7.63 (s, 1H), 7.37 (d, 1H), 7.27 (s, 1H), 7.21 (s, 1H), 7.15 (d, 1H), 7.03 (d, 1H), 6.89 (d, 1H), 6.86 (s, 1H), 3.93 (s, 2H), 3.83 (s, 3H), 2.29 (s, 3H), 2.27 (s, 3H).

EXAMPLE 72

[4-(4-Methyl-imidazol-1-yl)-phenyl]-(5-methyl-4-phenyl-thiazol-2-yl)-amine a) 4-Methyl-1-(4-nitro-phenyl)-1H-imidazole Prepared in analogy to example 64 a) from 14.1 g (100 mmol) 4-fluoro-1-nitrobenzene, 8.21 g (100 mmol) 4-methylimidazole and 20.73 g (150 mmol) potassium carbonate. 14.75 g (73%) of the product was isolated as brownish solid. MS ISP (m/e): 204.1 (100) (M+H)$^+$. $^1$H NMR (DMSO-D$_6$, 300 MHz): δ (ppm)=8.38 (d, 2H), 7.93 (s, 1H), 7.78 (d, 2H), 6.89 (s, 1H), 2.24 (s, 3H).
b) 4-(4-Methyl-imidazol-1-yl)-phenylamine A solution of 38.5 g (189 mmol) 4-methyl-1-(4-nitro-phenyl)-1H-imidazole in a mixture of 125 ml methanol and 120 ml hydrochloric acid 37% was cooled in an ice bath and 47.5 g (852 mmol) of iron powder was slowly added, keeping the temperature between 40 to 50° C. 500 ml ethyl acetate was added and the mixture was filtered. The organic phase was washed with diluted sodium carbonate solution, dried and evaporated. Crystallization from dichloromethane/heptane gave 20.9 g (64%) of the product as a slightly brownish solid. MS ISP (m/e): 174.3 (100) (M+H)$^+$. $^1$H NMR (DMSO-D$_6$, 300 MHz): δ (ppm)=7.80 (s, 1H), 7.20-7.14 (m, 3H), 6.62 (d, 2H), 5.23 (s broad, 2H), 2.13 (s, 3H).

c) [4-(4-Methyl-imidazol-1-yl)-phenyl]-thiourea

Prepared in analogy to example 64c) from 1.0 g (5.77 mmol) 4-(4-methyl-imidazol-1-yl)-phenylamine and 989 mg (6.06 mmol) benzoylisothiocyanate. 1.27 g (95%) of the product was isolated as a slightly brownish solid. MS (m/e): 232.7 (77) (M$^+$). $^1$H NMR (DMSO-D$_6$, 300 MHz): δ (ppm)= 9.80 (s very broad, 1H), 8.08 (s, 1 H), 7.60-7.50 (m, 4H), 7.40 (s, 1H), 2.16 (s, 3H).
d) [4-(4-Methyl-imidazol-1-yl)-phenyl]-(5-methyl-4-phenyl-thiazol-2-yl)-amine Prepared in analogy to example 64d) from 100 mg (0.43 mmol) [4-(4-methyl-imidazol-1-yl)-phenyl]-thiourea and 101 mg (0.47 mmol) 2-bromopropiophenone. 140 mg (94%) of the product was isolated as a colorless solid. MS ISP (m/e): 347.1 (100) (M+H)$^+$. $^1$H NMR (DMSO-D$_6$, 300 MHz): δ (ppm)=10.48 (s, 1H), 9.46 (s, 1H), 7.93 (s, 1H), 7.88 (d, 2H), 7.69 (d, 2H), 7.47 (t, 2H), 7.36 (t, 1H), 2.46 (s, 3H), 2.34 (s, 3H).

EXAMPLE 73

(4,5-Diphenyl-thiazol-2-yl)-[4-(4-methyl-imidazol-1-yl)-phenyl]-amine

Prepared in analogy to example 64d) from 100 mg (0.43 mmol) [4-(4-methyl-imidazol-1-yl)-phenyl]-thiourea (example 72c)) and 130 mg (0.47 mmol) desyl bromide. 155 mg (88%) of the product was isolated as a colorless solid. MS ISP (m/e): 409.3 (100) (M+H)$^+$. $^1$H NMR (DMSO-D$_6$, 300 MHz): δ (ppm)=10.74 (s, 1H), 9.50 (s, 1H), 8.00-7.90 (m, 3H), 7.73 (d, 2H), 7.49 (d, 2H), 7.40-7.30 (m, 8H), 2.35 (s, 3H).

EXAMPLE 74

[4-(3-Chloro-4-methyl-phenyl)-5-methyl-thiazol-2-yl]-[4-(4-methyl-imidazol-1-yl)-phenyl]-amine Prepared in analogy to example 64d) from 100 mg (0.43 mmol) [4-(4-methyl-imidazol-1-yl)-phenyl]-thiourea (example 72c)) and 124 mg (0.47 mmol) 2-bromo-3'-chloro-4'-methylpropiophenone. 115 mg (68%) of the product was isolated as a colorless solid. MS ISP (m/e): 395.1 (100) (M+H)$^+$. $^1$H NMR (DMSO-D$_6$, 300 MHz): δ (ppm)=10.50 (s, 1H), 9.47 (s, 1H), 7.95 (s, 1H), 7.87 (d, 2H), 7.70-7.60 (m, 3H), 7.52 (d, 2H), 2.45 (s, 3H), 2.41 (s, 3H), 2.35 (s, 3H).

EXAMPLE 76

(4-Chloro-phenyl)-{2-[3-methoxy-4-(4-methyl-imidazol-1-yl)-phenylamino]-thiazol-5-yl}-methanol a) (5-Formyl-thiazol-2-yl)-[3-methoxy-4-(4-methyl-imidazol-1-yl)-phenyl]-carbamic acid tert-butyl ester To a solution of 100 mg (0.32 mmol) 2-[3-methoxy-4-(4-methyl-imidazol-1-yl)-phenylamino]-thiazole-5-carbaldehyde in methylenechloride (2 ml) was added 77 mg (0.35 mmol) di-tert.butyl-dicarbonate and 4 mg (0.03 mmol) 4-dimethylaminopyridine at 0° C. under nitrogen. The reaction was stirred at room temperature over night. The reaction was diluted with methylene chloride, washed once with water and once with brine. The organic layer was dried over sodium sulfate, filtered and the solvent was evaporated under reduce pressure. The crude product was purified on silica gel with methylene chloride/methanol 19/1 as eluent yielding 100 mg (49%) of the title compound as a yellow oil. $^1$H NMR (DMSO-D$_6$, 300 MHz): δ (ppm)=9.94 (s, 1H), 8.26 (s, 1H), 7.85 (s, 1H), 7.46 (d, 1H), 7.40 (s, 1H), 7.20 (s, 1H), 7.10 (d, 1H), 3.80 (s, 3H), 2.17 (s, 3H), 1.44 (s, 9H).

b) (4-Chloro-phenyl)-{2-[3-methoxy-4-(4-methyl-imidazol-1-yl)-phenylamino]-thiazol-5-yl}-methanol To a solution of 100 mg (0.24 mmol) (5-formyl-thiazol-2-yl)-[3-methoxy-4-(4-methyl-imidazol-1-yl)-phenyl]-carbamic acid tert-butyl ester in tetrahydrofurane (2 ml) was added slowly 0.36 ml (0.36 mmol) 1 M 4-chlorophenylmagnesium bromide solution in diethyl ether at −78° C. under nitrogen. The reaction was stirred at −78° C. for 1 h and at 0° C. for 30 minutes. The reaction was treated with saturated aqueous ammonium chloride solution and extracted twice with methylene chloride. The combined organic layers were washed with brine, dried over sodium sulfate, filtered and the solvent was evaporated under reduced pressure. The residue was purified on silica gel with methylene chloride/methanol/sat. aq. $NH_3$ solution 9/1/0.1 yielding 14 mg (14%) of the title compound as a yellow gum. $^1$H NMR (CDCl$_3$, 300 MHz): δ (ppm)=7.58 (s, 1H), 7.41 (d, 2H), 7.35 (d, 2H), 7.19 (s, 1H), 7.16 (d, 1H), 7.05 (s, 1H), 6.90 (d, 1H), 6.85 (s, 1H), 5.98 (s, 1H), 3.81 (s, 3H), 2.28 (s, 3H).

EXAMPLE 77

{4-[1-(4-Chloro-phenyl)-1-methyl-ethyl]-thiazol-2-yl}-[3-methoxy-4-(4-methyl-imidazol-1-yl)-phenyl]-amine A suspension of 78.7 mg (0.3 mmol) [3-methoxy-4-(4-methyl-imidazol-1-yl)-phenyl]-thiourea and of 76.2 mg (0.33 mmol) 3,4'-dichloro-2,2-dimethyl-propiophenone (CAS: 30127-02-7) in ethanol (3 ml) was heated to reflux over night. The solvent was evaporated under reduced pressure and the residue was purified by column chromatography on silica gel using methylene chloride/methanol 19/1 to 9/1 as eluent to yield 103 mg (78%) of the title compound as colorless foam, which crystallized on standing. MS ISP (m/e): 439.2/441.3 (100/47) (M+H)$^+$. $^1$H NMR (DMSO-D$_6$, 300 MHz): δ (ppm)= 10.32 (s, 1H), 7.84 (s, 1H), 7.61 (s, 1H), 7.32 (dd, 4H), 7.19 (d, 1H), 6.99 (s, 1H), 6.85 (d, 1H), 6.67 (s, 1H), 3.60 (s, 3H), 2.12 (s, 3H), 1.64 (s, 6H).

EXAMPLE 78

[3-Methoxy-4-(4-methyl-imidazol-1-yl)-phenyl]-{4-[1-methyl-1-(3,4,5-trifluoro-phenyl)-ethyl]-thiazol-2-yl}-amine a) 2-Methyl-2-(3,4,5-trifluoro-phenyl)-propionitrile 3.44 g (30 mmol) of potassium tert.-butoxide was dissolved in tetrahydrofuran (100 mL) and stirred under am atmosphere of nitrogen. 2.12 g (12 mmol) of (3,4,5-trifluorophenyl)-acetonitrile dissolved in tetrahydrofuran (10 mL) was added drop wise at 0° C. The solution turned orange and heat was evolved. 1.88 mL (30 mmol) of methyl iodide dissolved in tetrahydrofuran (10 mL) was added drop wise. The solution turned pale brown and was stirred for 4 h at 20° C. The reaction was poured onto water and extracted twice with diethyl ether. The combined organic layers were washed with brine, dried over sodium sulfate, filtered and the solvent was evaporated und reduce pressure to yield 2.30 g (96%) of the title compound as a yellow solid. $^1$H NMR (CDCl$_3$, 300 MHz): δ (ppm)=7.26 (m, 2H), 1.71 (s, 6H).

b) 3-Methyl-3-(3,4,5-trifluoro-phenyl)-butan-2-one

To a solution of 2.3 g (12 mmol) of 2-methyl-2-(3,4,5-trifluoro-phenyl)-propionitrile in benzene (120 mL) was added slowly at 50° C. under an atmosphere of nitrogen with stirring 4.62 ml (14 mmol) of a 2.8 M solution of methylmagnesium chloride in tetrahydrofuran. The reaction mixture was heated to reflux for 2 h, and thereafter, cooled and poured onto 10% aqueous ammonium chloride solution (24 mL). The organic layer was separated and treated with 2 N aqueous hydrochloric acid solution (6 mL). The reaction was heated to reflux for 1 h. After cooling the reaction mixture was diluted with water and extracted twice with benzene. The organic layer was washed with brine, dried over sodium sulfate and evaporated under reduced pressure. The residue was purified by column chromatography on silica gel using heptane/ethyl acetate 9/1 as eluent to give 2.13 g (73%) of the title compound as a yellow oil. $^1$H NMR (DMSO-D$_6$, 300 MHz): δ (ppm)=7.26-7.21 (m, 2H), 1.97 (s, 3H), 1.42 (s, 6H).

c) 1-Chloro-3-methyl-3-(3,4,5-trifluoro-phenyl)-butan-2-one

A solution of 108 mg (0.5 mmol) of 3-methyl-3-(3,4,5-trifluoro-phenyl)-butan-2-one and 359 mg (1.0 mmol) of benzyltrimethylammoniumdichlroiodide in a mixture of dichloroethane (2.5 ml) and methanol (1.3 mmol) was heated to reflux for 2 h. The solvent was evaporated under reduced pressure and the residue was treated with 5% aqueous sodium bisulfite solution (1.25 ml) under ice cooling. The mixture was stirred for 10 minutes and extracted twice with ethyl acetate. The combined organic layers were washed once with brine, dried over sodium sulfate, filtered and the solvent was evaporated under reduce pressure. The residue was purified by column chromatography on silica gel using methylene chloride as eluent to give 129 mg (quant) of the title compound as a brown oil. $^1$H NMR (CDCl$_3$, 300 MHz): δ (ppm)= 6.93-6.87 (m, 4H), 4.05 (s, 2H), 1.53 (s, 6H).

d) [3-Methoxy-4-(4-methyl-imidazol-1-yl)-phenyl]-{4-[1-methyl-1-(3,4,5-trifluoro-phenyl)-ethyl]-thiazol-2-yl}-amine A suspension of 78.7 mg (0.3 mmol) [3-methoxy-4-(4-methyl-imidazol-1-yl)-phenyl]-thiourea and of 90.2 mg (0.36 mmol) 1-chloro-3-methyl-3-(3,4,5-trifluoro-phenyl)-butan-2-one in ethanol (3 ml) was heated to reflux over night. The solvent was evaporated under reduced pressure and the residue was purified by column chromatography on silica gel using methylene chloride/methanol 19/1 to 9/1 as eluent to yield 95 mg (69%) of the title compound as a light yellow solid. MS ISP (m/e): 459.1 (100) [(M+H)$^+$]. $^1$H NMR (DMSO-D$_6$, 300 MHz): δ (ppm)=10.38 (s, 1H), 7.83 (s, 1H), 7.63 (s, 1H), 7.23-7.18 (m, 3H), 7.01 (s, 1H), 6.88 (d, 1H), 6.69 (s, 1H), 3.68 (s, 3H), 2.13 (s, 3H), 1.65 (s, 6H).

The invention claimed is:

1. A compound of formula I

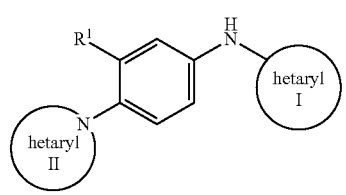

wherein
hetaryl I is

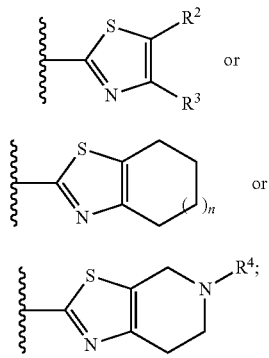

a) b) c)

hetaryl II is

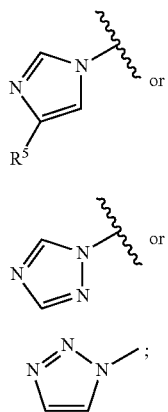

d) e) f)

R¹ is hydrogen, lower alkoxy or cyano;
R² and R³ are each independently
    hydrogen,
    lower alkyl,
    lower alkyl substituted by halogen,
    CHO,
    —CRR'-phenyl, wherein the phenyl rings are unsubstituted or substituted
        by one or more halogen, cyano, lower alkyl, lower alkyl substituted by halogen,
        lower alkoxy substituted by halogen or lower alkoxy,
    —C(O)O-lower alkyl,
    —CH₂—C(O)O-lower alkyl,
    —CH₂—C(O)-piperidin-1-yl,
    —CH₂—C(O)NH-lower alkyl,
    —CH₂—C(O)NH-phenyl optionally substituted by halogen,
    —CHR—NHC(O)O-lower alkyl,
    —CHR—NH₂,
    —CHR—NH—CH₂-phenyl optionally substituted by halogen,
    —CHR—NH—(CH₂)₂-phenyl optionally substituted by halogen,
    —CHR—NH—phenyl optionally substituted by halogen,
    —CHR—NH—cycloalkyl,
    —CHR—NHC(O)—CH₂-phenyl optionally substituted by halogen,
    —CHR—NHC(O)—CH₂O-lower alkyl,
    —CHR—NHC(O)-lower alkyl,
    —CHR—NHC(O)O-lower alkyl substituted by halogen,
    —CHR—NHC(O)-phenyl optionally substituted by halogen,
    —CHR—NHCH₂CH₂O-lower alkyl,
    —CHR—NH—S(O)₂-phenyl optionally substituted by halogen or lower alkyl,
    —CHR—NH—S(O)₂—CH₂-phenyl optionally substituted by halogen,
    —CHR—NH—S(O)₂-lower alkyl,
    —CH₂-piperidin-1-yl,
    —CH₂-morpholinyl or
    -indole-2-carboxylic acid-(3,4-difluoro-phenyl)amide;
R and R' are each independently hydrogen, lower alkyl, benzyl or hydroxy;
R⁴ is hydrogen,
    —C(O)O-lower alkyl,
    —C(O)-phenyl optionally substituted by halogen,
    —C(O)-lower alkyl substituted by halogen,
    —C(O)-lower alkyl,
    —S(O)₂-phenyl optionally substituted by halogen,
    —S(O)₂-lower alkyl,
    —S(O)₂—CH₂- phenyl,
    -benzyl optionally substituted by halogen,
    —CH₂—CH₂-phenyl,
    —C(O)—CH₂-phenyl optionally substituted by halogen or
    —C(O)—CH₂-lower alkoxy;
R⁵ is halogen, lower alkyl substituted by hydroxy, or is lower alkyl; and
n is 0 or 1;
or a pharmaceutically active acid addition salt thereof.

2. A compound of claim 1 having formula I-A-1,

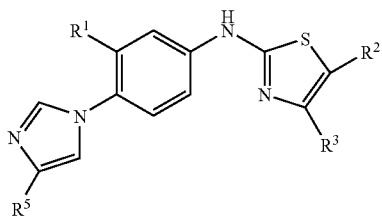

I-A-1 wherein
R¹ is hydrogen, lower alkoxy or cyano;
R² and R³ are each independently hydrogen,
    lower alkyl,
    lower alkyl substituted by halogen,
    CHO,
    —CRR'-phenyl, wherein the phenyl rings are unsubstituted or Substituted
        by one or more halogen, cyano, lower alkyl, lower alkyl substituted by halogen,
        lower alkoxy substituted by halogen or lower alkoxy,
    —C(O)O-lower alkyl,
    —CH₂—C(O)O-lower alkyl,
    —CH₂—C(O)-piperidin-1-yl,
    —CH₂—C(O)NH-lower alkyl,
    —CH₂—C(O)NH-phenyl optionally substituted by halogen, —CHR—NHC(O)O-lower alkyl,
—CHR—NH₂,
—CHR—NH—CH₂-phenyl optionally substituted by halogen,
—CHR—NH—(CH₂)₂-phenyl optionally substituted by halogen,
—CHR—NH-phenyl optionally substituted by halogen,
—CHR—NH-cycloalkyl,
—CHR—NHC(O)—CH₂-phenyl optionally substituted by halogen,
—CHR—NHC(O)—CH₂O-lower alkyl,
—CHR—NHC(O)-lower alkyl,
—CHR—NHC(O)O-lower alkyl substituted by halogen,
—CHR—NHC(O)-phenyl optionally substituted by halogen,
—CHR—NHCH₂CH₂O-lower alkyl,
—CHR—NH—S(O)₂-phenyl optionally substituted by halogen or lower alkyl,
—CHR—NH—S(O)₂—CH₂-phenyl optionally substituted by halogen,
—CHR—NH—S(O)₂-lower alkyl,
—CH₂-piperidin-1-yl,
—CH₂-morpholinyl or
-indole-2-carboxylic acid-(3,4-difluoro-phenyl)amide;
R and R' are each independently hydrogen, lower alkyl, benzyl or hydroxy; and
R⁵ is halogen, lower alkyl substituted by hydroxy, or is lower alkyl;
or a pharmaceutically active acid addition salt thereof.

3. A compound of claim 2 having formula I-A-1, wherein R¹ is hydrogen, lower alkoxy or cyano;
R² and R³ are each independently
  hydrogen,
  lower alkyl,
  lower alkyl substituted by halogen,
  —CRR'-phenyl, wherein the phenyl group is unsubstituted or substituted by one or more halogen lower alkyl, lower alkyl substituted by halogen, lower alkoxy substituted by halogen, or lower alkoxy,
  —CH₂—C(O)NH-phenyl optionally substituted by halogen, or are
  —CHR—NHC(O)O-lower alkyl, CHR—NHC(O)O-lower alkyl substituted by halogen,
  —CHR—NHC(O)—CH₂-phenyl optionally substituted by halogen,
  —CHR—NHC(O)-phenyl optionally substituted by halogen,
  —CHR—NH—S(O)₂-phenyl optionally substituted by halogen or lower alkyl,
  —CHR—NH—S(O)₂—CH₂-phenyl optionally substituted by halogen, or
  —CHR—NH—S(O)₂-lower alkyl;
R and R' are each independently hydrogen, lower alkyl, benzyl or hydroxyl, wherein at least one of R and R' is other than hyydrogen; and
R⁵ is lower alkyl;
or a pharmaceutically active acid addition salt thereof.

4. A compound of claim 1, selected from the group consisting of
[5-(3-chloro-benzyl)-4-methyl-thiazol-2-yl]-[3-methoxy-4-(4-methyl-imidazol-1-yl)-phenyl]-amine,
[5-(4-chloro-benzyl)-4-methyl-thiazol-2-yl]-[3-methoxy-4-(4-methyl-imidazol-1-yl)-phenyl]-amine,
5[5-(3-chloro-benzyl)-4-methyl-thiazol-2-ylamino]-2-(4-methyl-imidazol-1-yl)-benzonitrile,
N-(4-fluoro-phenyl)-2-{2-[3-methoxy-4-(4-methyl-imidazol-1-yl)-phenylamino]-thiazol-4-yl}-acetamide,
((S)-1-{2-[3-methoxy-4-(4-methyl-imidazol-1-yl)-phenylamino]-thiazol-4-yl}-3-methyl-butyl) -carbamic acid tert-butyl ester,
2-(4-fluoro-phenyl)-N-((S)-1-{2-[3-methoxy-4-(4-methyl-imidazol-1-yl)-phenylamino]-thiazol -4-yl}-3-methyl-butyl)- acetamide, 4-fluoro-N-((S)-1-{2-[3-methoxy-4-(4-methyl-imidazol-1-yl)-phenylamino]-thiazol-4-yl}-3-methyl-butyl)-benzamide,
3,3,3-trifluoro-N-((S)-1-{2-[3-methoxy-4-(4-methyl-imidazol-1-yl)-phenylamino]-thiazol-4-yl}-3-methyl-butyl)-propionamide,
4-fluoro-N-((S)-1 -{2-[3-methoxy-4-(4-methyl-imidazol-1 -yl)-phenylamino]-thiazol-4-yl}-3-methyl-butyl)-benzenesulfonamide,
N-((S)-1 -{2-[3-methoxy-4-(4-methyl-imidazol-1 -yl)-phenylamino]-thiazol-4-yl}1-3-methyl-butyl) -C-phenyl-methanesulfonamide,
N-((S)-1 -{2-[3-methoxy-4-(4-methyl-imidazol-1 -yl)-phenylamino]-thiazol-4-yl}-3-methyl-butyl)-methane-sulfonamide,
2-[3-methoxy-4-(4-methyl-imidazol-1 -yl)-phenylamino]-4-trifluoromethyl-thiazole-5-carboxylic acid ethyl ester,
N-((S)-1 -{2-[3-methoxy-4-(4-methyl-imidazol-1 -yl)-phenylamino]-thiazol-4-yl}-2-phenyl-ethyl) -4-methyl-benzenesulfonamide
{2-[3-methoxy-4-(4-methyl-imidazol-1-yl)-phenylamino]-thiazol-5-yl}-phenyl-methanol (4-chloro-phenyl)-{2-[3-methoxy-4-(4-methyl-imidazol-1 -yl)-phenylamino]-thiazol-5-yl}-methanol
{4-[1 -(4-chloro-phenyl)-1 -methyl-ethyl]-thiazol-2-yl} [3-methoxy-4-(4-methyl-imidazol-1 -yl)-phenyl]-amine and
[3-methoxy-4-(4-methyl-imidazol-1-yl)-phenyl]-{4-[1 -methyl-1 -(3,4,5-trifluoro-phenyl) -ethyl]-thiazol-2-yl}-amine.

5. A compound of claim 2, having formula I-A-1, wherein R¹ is hydrogen or lower alkoxy;
R² and R³ are each independently lower alkyl or benzyl which is unsubstituted or substituted by one or more halogen, cyano, lower alkyl, lower alkyl substituted by halogen or lower alkoxy substituted by halogen; and
R⁵ is lower alkyl;
or a pharmaceutically active acid addition salt thereof.

6. A compound of claim 5, selected from the group consisting of
4-{2-[3-methoxy-4-(4-methyl-imidazol-1-yl)-phenylamino]-4-methyl-thiazol-5-ylmethyl}-benzonitrile,
[5-(2-chloro-benzyl)-4-methyl-thiazol-2-yl]-[3-methoxy-4-(4-methyl-imidazol-1-yl) -phenyl]-amine,
[5-(4-tert-butyl-benzyl)-4-methyl-thiazol-2-yl]-[3-methoxy-4-(4-methyl-imidazol-1-yl) -phenyl]-amine
[3-methoxy-4-(4-methyl-imidazol-1-yl)-phenyl]-[4-methyl-5-(3-trifluoromethyl-benzyl) -thiazol-2-yl]-amine
[5-(4-chloro-3-trifluoromethyl-benzyl)-4-methyl-thiazol-2-yl]-[3-methoxy-4-(4-methyl -imidazol-1-yl)-phenyl]-amine
[3-methoxy-4-(4-methyl-imidazol-1-yl)-phenyl]-{4-methyl-5-[3-(1,1,2,2-tetrafluoro -ethoxy)-benzyl]-thiazol-2-yl}-amine
[5-(3-chloro-4-methyl-benzyl)-4-methyl-thiazol-2-yl]-[3-methoxy-4-(4-methyl-imidazol-1-yl)-phenyl]-amine and

[5-(3,4-dichloro-benzyl)-4-methyl-thiazol-2-yl]-[3-methoxy-4-(4-methyl-imidazol-1-yl)-phenyl]-amine.

7. A compound of claim 1 having formula I-A-2

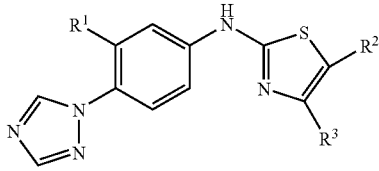

I-A-2 wherein
$R^1$ is hydrogen, lower alkoxy or cyano;
$R^2$ and $R^3$ are each independently
  hydrogen,
  lower alkyl,
  lower alkyl substituted by halogen,
  CHO,
  benzyl which are unsubstituted or substituted by halogen, cyano, lower alkyl, lower alkyl substituted by halogen or lower alkoxy,
  —CHR-phenyl,
  —C(O)O-lower alkyl,
  —CH$_2$—C(O)O-lower alkyl,
  —CH$_2$—C(O)-piperidin-1-yl,
  —CH$_2$—C(O)NH-lower alkyl,
  —CH$_2$—C(O)NH-phenyl optionally substituted by halogen,
  —CHR—NHC(O)O-lower alkyl,
  —CHR—NH$_2$,
  —CHR—NH—CH$_2$-phenyl optionally substituted by halogen,
  —CHR—NH—(CH$_2$)$_2$-phenyl optionally substituted by halogen,
  —CHR—NH-phenyl optionally substituted by halogen,
  —CHR—NH-cycloalkyl,
  —CHR—NHC(O)—CH$_2$-phenyl optionally substituted by halogen,
  —CHR—NHC(O)—CH$_2$O-lower alkyl,
  —CHR—NHC(O)-lower alkyl,
  —CHR—NHC(O)O-lower alkyl substituted by halogen,
  —CHR—NHC(O)-phenyl optionally substituted by halogen,
  —CHR—NHCH$_2$CH$_2$O-lower alkyl,
  —CHR—NH—S(O)$_2$-phenyl optionally substituted by halogen or lower alkyl,
  —CHR—NH—S(O)$_2$—CH$_2$-phenyl optionally substituted by halogen,
  —CHR—NH—S(O)$_2$-lower alkyl,
  —CH$_2$-piperidin-1-yl or
  —CH$_2$-morpholinyl; and
R is hydrogen, lower alkyl, benzyl or hydroxy;
or a pharmaceutically active acid addition salt thereof.

8. A compound of claim 7, wherein
$R^1$ is hydrogen or lower alkoxy and
$R^2$ and $R^3$ are each independently lower alkyl or benzyl substituted by halogen.

9. A compound of claim 8, which compound is
[5-(3-chloro-benzyl)-4-methyl-thiazol-2-yl]-(4-[1,2,4]triazol-1-yl-phenyl)-amine.

10. A compound of claim 1 having formula I-B-1

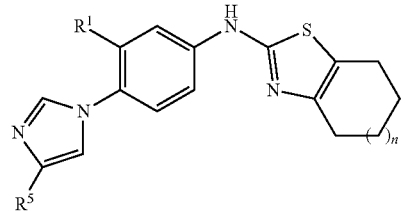

I-B-1 wherein
$R^1$ is hydrogen, lower alkoxy or cyano;
$R^5$ is hydrogen or lower alkyl; and
n is 0 or 1;
or a pharmaceutically active acid addition salt thereof.

11. A compound of claim 10, wherein $R^1$ is lower alkoxy, $R^5$ is lower alkyl, and n is 0 or 1.

12. A compound of claim 11, selected from the group consisting of
  [3-methoxy-4-(4-methyl-imidazol-1-yl)-phenyl]-(4,5,6,7-tetrahydro-benzothiazol-2-yl)-amine and
  (5,6-dihydro-4H-cyclopentathiazol-2-yl)-[3-methoxy-4-(4-methyl-imidazol-1-yl)-phenyl]-amine.

13. A compound of claim 1 having formula I-C-1,

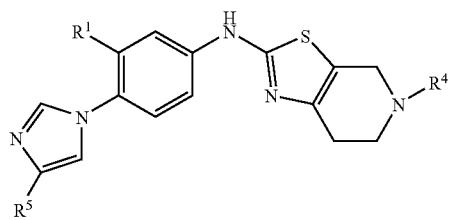

I-C-1 wherein
$R^1$ is lower alkoxy;
$R^4$ is hydrogen,
  —C(O)O-lower alkyl,
  —C(O)-phenyl optionally substituted by halogen,
  —C(O)-lower alkyl substituted by halogen,
  —C(O)-lower alkyl,
  —S(O)$_2$-phenyl optionally substituted by halogen,
  —S(O)$_2$-lower alkyl,
  —S(O)$_2$—CH$_2$-phenyl,
  benzyl optionally substituted by halogen,
  —CH$_2$—CH$_2$-phenyl,
  —C(O)—CH$_2$-phenyl optionally substituted by halogen or —C(O)—CH$_2$-lower alkoxy; and
$R^5$ is hydrogen or lower alkyl;
or a pharmaceutically active acid addition salt thereof.

14. A compound of claim 13, selected from the group consisting of
  2[3-mthoxy-4-(4-methyl-imidazol-1-yl)-phenylamino]-6,7-dihydro-4H-thiazolo[5,4-c]pyridine-5-carboxylic acid tert-butyl ester,
  [3-mthoxy-4-(4-methyl-imidazol-1-yl)-phenyl]-(4,5,6,7-tetrahydro-thiazolo[5,4-c]pyridin-2-yl)-amine trihydrochloride,
  (4-fuoro-phenyl)-{2-[3-methoxy-4-(4-methyl-imidazol-1-yl)-phenylamino]-6,7-dihydro-4H-thiazolo[5,4-c]pyridin-5-yl}-methanone, 3,3,3-trifluoro-1-{2-[3-methoxy-4-(4-methyl-imidazol-1-yl)-phenylamino]-6,7-dihydro-4H-thiazolo[5,4-c]pyridin-5-yl}-propan-1-one, 1-{2-[3-methoxy-4-(4-methyl-imidazol-1-yl)-phenylamino]-6,7-dihydro-4H-thiazolo[5,4-c]pyridin-5-yl}-2,2-dimethyl-propan-1-one,

[5-(4-fluoro-benzenesulfonyl)-4,5,6,7-tetrahydro-thiazolo[5,4-c]pyridin-2-yl]-3-methoxy-4-(4-methyl-imidazol-1-yl)-phenyl]-amine, (5-methanesulfonyl-4,5,6,7-tetrahydro-thiazolo[5,4-c]pyridin-2-yl)-[3-methoxy-4-(4-methyl-imidazol-1-yl)-phenyl]-amine,

[3-methoxy-4-(4-methyl-imidazol-1-yl)-phenyl]-(5-phenylmethanesulfonyl-4,5,6,7-tetrahydro-thiazolo[5,4-c]pyridin-2-yl)-amine,

[5-(4-fluoro-benzyl)-4,5,6,7-tetrahydro-thiazolo[5,4-c]pyridin-2-yl]-[3-methoxy-4-(4-methyl-imidazol-1-yl)-phenyl]-amine,

[3-methoxy-4-(4-methyl-imidazol-1-yl)-phenyl]-(5-phenethyl-4,5,6,7-tetrahydro-thiazolo[5,4-c]pyridin-2-yl)-amine, 2-(4-fluoro-phenyl)-1-{2-[3-methoxy-4-(4-methyl-imidazol-1-yl)-phenylamino]-6,7-dihydro-4H-thiazolo[5,4-c]pyridin-5-yl}-ethanone and 2-methoxy-1-{2-[3-methoxy-4-(4-methyl-imidazol-1-yl)-phenylamino]-6,7-dihydro-4H-thiazolo[5,4-c]pyridin-5-yl}-ethanone.

15. A pharmaceutical composition comprising a therapeutically effective amount of a compound for formula I

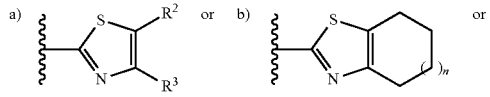

wherein
hetaryl I is

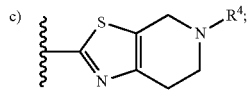

hetaryl II is

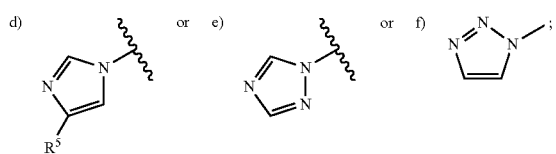

$R^1$ is hydrogen, lower alkoxy or cyano;
$R^2$ and $R^3$ are each independently
  hydrogen,
  lower alkyl,
  lower alkyl substituted by halogen,
  CHO,
  —CRR'-phenyl, wherein the phenyl rings are unsubstituted or substituted
    by one or more halogen, cyano, lower alkyl, lower alkyl substituted by halogen,
    lower alkoxy substituted by halogen or lower alkoxy,
  —C(O)O-lower alkyl,
  —CH$_2$—C(O)O-lower alkyl,
  —CH$_2$—C(O)-piperidin-1-yl,
  —CH$_2$—C(O)NH-lower alkyl,
  —CH$_2$—C(O)NH-phenyl optionally substituted by halogen,
  —CHR—NHC(O)O-lower alkyl,
  —CHR—NH$_2$,
  —CHR—NH—CH$_2$-phenyl optionally substituted by halogen,
  —CHR—NH—(CH$_2$)$_2$-phenyl optionally substituted by halogen,
  —CHR—NH-phenyl optionally substituted by halogen,
  —CHR—NH-cycloalkyl,
  —CHR—NHC(O)—CH$_2$-phenyl optionally substituted by halogen,
  —CHR—NHC(O)—CH$_2$O-lower alkyl,
  —CHR—NHC(O)-lower alkyl,
  —CHR—NHC(O)O-lower alkyl substituted by halogen,
  —CHR—NHC(O)-phenyl optionally substituted by halogen,
  —CHR—NHCH$_2$CH$_2$O-lower alkyl,
  —CHR—NH—S(O)$_2$-phenyl optionally substituted by halogen or lower alkyl,
  —CHR—NH—S(O)$_2$—CH$_2$-phenyl optionally substituted by halogen,
  —CHR—NH—S(O)$_2$-lower alkyl,
  —CH$_2$-piperidin-1-yl,
  —CH$_2$-morpholinyl or
  -indole-2-carboxylic acid-(3,4-difluoro-phenyl)amide;
R and R' are each independently hydrogen, lower alkyl, benzyl or hydroxy;
$R^4$ is hydrogen,
  —C(O)O -lower alkyl,
  —C(O)-phenyl optionally substituted by halogen,
  —C(O)-lower alkyl substituted by halogen,
  —C(O)-lower alkyl,
  —S(O)$_2$-phenyl optionally substituted by halogen,
  —S(O)$_2$-lower alkyl,
  —S(O)$_2$—CH$_2$-phenyl,
  -benzyl optionally substituted by halogen,
  —CH$_2$—CH$_2$-phenyl,
  —C(O)—CH$_2$-phenyl optionally substituted by halogen or
  —C(O)—CH$_2$-lower alkoxy;
$R^5$ is halogen, lower alkyl substituted by hydroxy, or is lower alkyl; and
n is 0 or 1;
or a pharmaceutically active acid addition salt thereof and a pharmaceutically acceptable carrier.

16. The composition of claim 15, wherein the compound of formula I is a compound of formula I-A-1

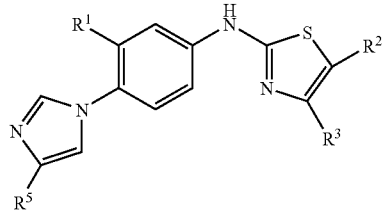

wherein

R¹ is hydrogen, lower alkoxy or cyano;

R² and R³ are each independently hydrogen,
  lower alkyl,
  lower alkyl substituted by halogen,
  CHO,
  —CRR'-phenyl, wherein the phenyl rings are unsubstituted or substituted
    by one or more halogen, cyano, lower alkyl, lower alkyl substituted by halogen,
    lower alkoxy substituted by halogen or lower alkoxy,
  —C(O)O-lower alkyl,
  —CH₂—C(O)O-lower alkyl,
  —CH₂—C(O)-piperidin-1-yl,
  —CH₂—C(O)NH-lower alkyl,
  —CH₂—C(O)NH-phenyl optionally substituted by halogen,
  —CHR—NHC(O)O-lower alkyl,
  —CHR—NH₂,
  —CHR—NH—CH₂-phenyl optionally substituted by halogen,
  —CHR—NH—(CH₂)₂-phenyl optionally substituted by halogen,
  —CHR—NH-phenyl optionally substituted by halogen,
  —CHR—NH-cycloalkyl,
  —CHR—NHC(O)—CH₂-phenyl optionally substituted by halogen,
  —CHR—NHC(O)—CH₂O-lower alkyl,
  —CHR—NHC(O)-lower alkyl,
  —CHR—NHC(O)O-lower alkyl substituted by halogen,
  —CHR—NHC(O)-phenyl optionally substituted by halogen,
  —CHR—NHCH₂CH₂O-lower alkyl,
  —CHR—NH—S(O)₂-phenyl optionally substituted by halogen or lower alkyl,
  —CHR—NH—S(O)₂—CH₂-phenyl optionally substituted by halogen,
  —CHR—NH—S(O)₂-lower alkyl,
  —CH₂-piperidin-1-yl,
  —CH₂-morpholinyl or
  -indole-2-carboxylic acid-(3,4-difluoro-phenyl)amide;

R and R' are each independently hydrogen, lower alkyl, benzyl or hydroxy; and

R⁵ is halogen, lower alkyl substituted by hydroxy, or is lower alkyl;

or a pharmaceutically active acid addition salt thereof.

17. The composition of claim 15, wherein the compound of formula I is a compound of formula I-A -2

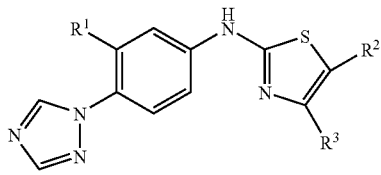

I-A-2 wherein

R¹ is hydrogen, lower alkoxy or cyano;

R² and R³ are each independently
  hydrogen,
  lower alkyl,
  lower alkyl substituted by halogen,
  CHO,
  benzyl which are unsubstituted or substituted by halogen, cyano, lower alkyl, lower alkyl substituted by halogen or lower alkoxy,
  —CHR-phenyl,
  —C(O)O-lower alkyl,
  —CH₂—C(O)O-lower alkyl,
  —CH₂—C(O)-piperidin-1-yl,
  —CH₂—C(O)NH-lower alkyl,
  —CH₂—C(O)NH-phenyl optionally substituted by halogen,
  —CHR—NHC(O)O-lower alkyl,
  —CHR—NH₂,
  —CHR—NH—CH₂-phenyl optionally substituted by halogen,
  —CHR—NH—(CH₂)₂-phenyl optionally substituted by halogen,
  —CHR—NH-phenyl optionally substituted by halogen,
  —CHR—NH-cycloalkyl,
  —CHR—NHC(O)—CH₂-phenyl optionally substituted by halogen,
  —CHR—NHC(O)—CH₂O-lower alkyl,
  —CHR—NHC(O)-lower alkyl,
  —CHR—NHC(O)O-lower alkyl substituted by halogen,
  —CHR—NHC(O)-phenyl optionally substituted by halogen,
  —CHR—NHCH₂CH₂O-lower alkyl,
  —CHR—NH—S(O)₂-phenyl optionally substituted by halogen or lower alkyl,
  —CHR—NH—S(O)₂—CH₂-phenyl optionally substituted by halogen,
  —CHR—NH—S(O)₂-lower alkyl,
  —CH₂-piperidin-1-yl or
  —CH₂-morpholinyl; and R is hydrogen, lower alkyl, benzyl or hydroxy;

or a pharmaceutically active acid addition salt thereof.

18. The composition of claim 15, wherein the compound of formula I is a compound of formula

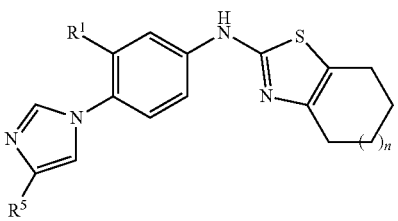

I-B-1 wherein

R¹ is hydrogen, lower alkoxy or cyano;

R⁵ is hydrogen or lower alkyl; and n is 0 or 1;

or a pharmaceutically active acid addition salt thereof.

19. The composition of claim 15, wherein the compound of formula I is a compound of formula

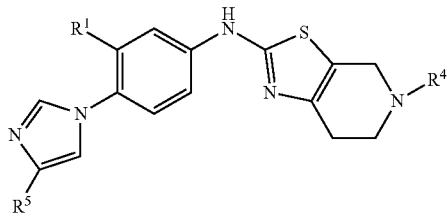

I-C-1 wherein
R¹ is lower alkoxy;
R⁴ is hydrogen,
—C(O)O-lower alkyl,
—C(O)-phenyl optionally substituted by halogen,
—C(O)-lower alkyl substituted by halogen,
—C(O)-lower alkyl,
—S(O)₂-phenyl optionally substituted by halogen,
—S(O)₂-lower alkyl,
—S(O)₂—CH₂-phenyl,
benzyl optionally substituted by halogen,
—CH₂—CH₂-phenyl,
—C(O)—CH₂-phenyl optionally substituted by halogen or
—C(O)—CH₂-lower alkoxy; and
R⁵ is hydrogen or lower alkyl;
or a pharmaceutically active acid addition salt thereof.

* * * * *

UNITED STATES PATENT AND TRADEMARK OFFICE
CERTIFICATE OF CORRECTION

PATENT NO. : 7,910,740 B2  Page 1 of 1
APPLICATION NO. : 12/114852
DATED : March 22, 2011
INVENTOR(S) : Baumann et al.

It is certified that error appears in the above-identified patent and that said Letters Patent is hereby corrected as shown below:

- Claim 18, column 58, line 62 "R5 is hydrogen or lower alkyl; and" should read
-- R5 is lower alkyl --.

- Claim 19, column 60, line 12, "R5 is hydrogen or lower alkyl; and" should read
-- R5 is lower alkyl --.

Signed and Sealed this
Twentieth Day of September, 2011

David J. Kappos
*Director of the United States Patent and Trademark Office*